(12) United States Patent
Stoytchev et al.

(10) Patent No.: US 10,007,662 B2
(45) Date of Patent: Jun. 26, 2018

(54) SYSTEMS AND METHODS FOR RECOGNIZING, CLASSIFYING, RECALLING AND ANALYZING INFORMATION UTILIZING SSM SEQUENCE MODELS

(71) Applicants: Alexander Stoytchev, Ames, IA (US); Volodymyr Sukhoy, Ames, IA (US)

(72) Inventors: Alexander Stoytchev, Ames, IA (US); Volodymyr Sukhoy, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 637 days.

(21) Appl. No.: 14/593,427

(22) Filed: Jan. 9, 2015

(65) Prior Publication Data

US 2015/0193431 A1 Jul. 9, 2015
US 2017/0154036 A9 Jun. 1, 2017
US 2018/0150457 A9 May 31, 2018

Related U.S. Application Data

(63) Continuation of application No. PCT/US2014/025094, filed on Mar. 12, 2014.

(60) Provisional application No. 61/777,032, filed on Mar. 12, 2013.

(51) Int. Cl.
| | |
|---|---|
| *G01N 33/48* | (2006.01) |
| *G01N 33/50* | (2006.01) |
| *G06F 17/28* | (2006.01) |
| *G06F 17/11* | (2006.01) |
| *G06F 17/10* | (2006.01) |

(52) U.S. Cl.
CPC .............. *G06F 17/28* (2013.01); *G06F 17/10* (2013.01); *G06F 17/11* (2013.01)

(58) Field of Classification Search
None
See application file for complete search history.

(56) References Cited

U.S. PATENT DOCUMENTS

| | | |
|---|---|---|
| 4,069,393 A | 1/1978 | Martin et al. |
| 2003/0101449 A1 | 5/2003 | Bentolila et al. |
| 2003/0110035 A1 | 6/2003 | Thong et al. |

(Continued)

OTHER PUBLICATIONS

Khrennikov Ay. On the theory of infifnite-dimensional superspace: reflexive Banach supermodules. vol. 77, No. 2, pp. 331-350. (Year: 1994).*

(Continued)

*Primary Examiner* — Russell S Negin
(74) *Attorney, Agent, or Firm* — Reinhart Boerner Van Deuren P.C.

(57) ABSTRACT

A biologically-inspired model for sequence representation, method of construction and application of such models, and systems incorporating same are provided. The model captures the statistical nature of sequences and uses that for sequence encoding, recognition, and recall. The model can be trained in real time, has few tunable parameters, and is highly parallelizable, which ensures that it can scale up to very large problems. Applications of the model to word and speech recognition, machine leaning, robotics, computational bioinformatics, genetics datasets, and other sequence processing pipelines are provided.

86 Claims, 62 Drawing Sheets

```
RR   RE   RA   RD
     EE   EA   ED
          AA   AD
               DD
```

(56) References Cited

U.S. PATENT DOCUMENTS

2004/0128291 A1    7/2004   Pentkovski et al.
2009/0083020 A1*   3/2009   Benayon ................ G06Q 10/06
                                                                              703/20

OTHER PUBLICATIONS

Ostendorf et al.; Integration of Diverse Recognition Methodologies Through Reevaluation of N-Best Sentence Hypotheses; Publication; Feb. 1991; pp. 83-87.

* cited by examiner

| Sequence | All Open Bigrams | | | | | | | SSM Matrix | | | | |
|---|---|---|---|---|---|---|---|---|---|---|---|---|
| | | | | | | | | | A | D | E | R |
| | RR | RE | RA | RD | | | | A | 1 | 1 | 0 | 0 |
| READ | | EE | EA | ED | | | | D | 0 | 1 | 0 | 0 |
| | | | AA | AD | | | | E | 1 | 1 | 1 | 0 |
| | | | | DD | | | | R | 1 | 1 | 1 | 1 |

| Sequence | All Open Bigrams | | | | | | | SSM Bigram Matrix | | | | | |
|---|---|---|---|---|---|---|---|---|---|---|---|---|---|
| | SS | SC | SI | SE | SN | SC | SE | | C | E | I | N | S |
| | | CC | CI | CE | CN | CC | CE | C | 3 | 3 | 1 | 1 | 0 |
| SCIENCE | | | II | IE | IN | IC | IE | E | 1 | 3 | 0 | 1 | 0 |
| | | | | EE | EN | EC | EE | I | 1 | 2 | 1 | 1 | 0 |
| | | | | | NN | NC | NE | N | 1 | 1 | 0 | 1 | 0 |
| | | | | | | CC | CE | S | 2 | 2 | 1 | 1 | 1 |
| | | | | | | | EE | | | | | | |

|   | A | B | C | D | E | F | G | H | I | J | K | L | M | N | O | P | Q | R | S | T | U | V | W | X | Y | Z |
|---|---|---|---|---|---|---|---|---|---|---|---|---|---|---|---|---|---|---|---|---|---|---|---|---|---|---|
| A | 1 | 0 | 0 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 |
| B | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| C | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| D | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| E | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| F | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| G | 0 | 0 | 0 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 |
| H | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| I | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| J | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| K | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| L | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| M | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| N | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| O | 1 | 0 | 0 | 0 | 1 | 0 | 1 | 0 | 0 | 0 | 0 | 0 | 0 | 0 | 1 | 0 | 0 | 1 | 0 | 0 | 0 | 0 | 0 | 0 | 0 | 0 |
| P | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Q | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| R | 1 | 0 | 0 | 0 | 1 | 0 | 1 | 0 | 0 | 0 | 0 | 0 | 0 | 0 | 0 | 0 | 0 | 1 | 0 | 0 | 0 | 0 | 0 | 0 | 0 | 0 |
| S | 1 | 0 | 0 | 0 | 1 | 0 | 1 | 0 | 0 | 0 | 0 | 0 | 0 | 0 | 1 | 0 | 0 | 1 | 1 | 0 | 0 | 0 | 0 | 0 | 0 | 0 |
| T | 1 | 0 | 0 | 0 | 1 | 0 | 1 | 0 | 0 | 0 | 0 | 0 | 0 | 0 | 1 | 0 | 0 | 1 | 0 | 1 | 0 | 0 | 0 | 0 | 0 | 0 |
| U | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| V | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| W | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| X | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Y | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Z | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

FIG. 4

|   | A | E | G | O | R | S | T |
|---|---|---|---|---|---|---|---|
| A | 1 | 1 | 1 | 0 | 0 | 0 | 0 |
| E | 0 | 1 | 0 | 0 | 0 | 0 | 0 |
| G | 0 | 1 | 1 | 0 | 0 | 0 | 0 |
| O | 1 | 1 | 1 | 1 | 1 | 0 | 0 |
| R | 1 | 1 | 1 | 0 | 1 | 0 | 0 |
| S | 1 | 1 | 1 | 1 | 1 | 1 | 1 |
| T | 1 | 1 | 1 | 1 | 1 | 0 | 1 |

FIG. 5

| Iteration # | Sequence | All Open Bigrams | Character Frequency Vector | SSM Matrix |
|---|---|---|---|---|
| Initialization | | | A [ 0 ]<br>B [ 0 ]<br>C [ 0 ] |    A B C<br>A 0 0 0<br>B 0 0 0<br>C 0 0 0 |
| First | A | AA | A [ 1 ]<br>B [ 0 ]<br>C [ 0 ] |    A B C<br>A 1 0 0<br>B 0 0 0<br>C 0 0 0 |
| Second | AC | AA  AC<br>      CC | A [ 1 ]<br>B [ 0 ]<br>C [ 1 ] |    A B C<br>A 1 0 1<br>B 0 0 0<br>C 0 0 1 |
| Third | ACB | AA  AC  AB<br>      CC  CB<br>           BB | A [ 1 ]<br>B [ 1 ]<br>C [ 1 ] |    A B C<br>A 1 1 1<br>B 0 1 0<br>C 0 1 1 |
| Fourth | ACBB | AA  AC  AB  AB<br>      CC  CB  CB<br>           BB  BB<br>                  BB | A [ 1 ]<br>B [ 2 ]<br>C [ 1 ] |    A B C<br>A 1 2 1<br>B 0 3 0<br>C 0 2 1 |
| Fifth | ACBB▒ | AA  AC  AB  AB  ▒<br>      CC  CB  CB  ▒<br>           BB  BB  ▒<br>                  BB  ▒ | A [ ▒ ]<br>B [ 2 ]<br>C [ 1 ] |    A B C<br>A ▒ 2 1<br>B ▒ 3 0<br>C ▒ 2 1 |

| Sequence | All Open Bigrams | 3 × 3 SSM Matrix | 4 × 4 SSM Matrix |
|---|---|---|---|
| CAT | CC  CA  CT<br>     AA  AT<br>         TT |    A C T<br>A 1 0 1<br>C 1 1 1<br>T 0 0 1 |    A C H T<br>A 1 0 0 1<br>C 1 1 0 1<br>H 0 0 0 0<br>T 0 0 0 1 |
| HAT | HH  HA  HT<br>     AA  AT<br>         TT |    A H T<br>A 1 0 1<br>H 1 1 1<br>T 0 0 1 |    A C H T<br>A 1 0 0 1<br>C 0 0 0 0<br>H 1 0 1 1<br>T 0 0 0 1 |

FIG. 10

| Sequence | All Open Bigrams | SSM Matrix | Unsmoothed | Smoothed |
|---|---|---|---|---|
| $S_1 = \text{THE}$ | $B_1 = \left\{\begin{array}{ccc} TT & TH & TE \\ & HH & HE \\ & & EE \end{array}\right\}$ |    E H T<br>E 1 ▓ 0<br>H 1 1 0 $= X$<br>T 1 1 1 |    E H T<br>E $1/6$ ▓ 0<br>H $1/6$ $1/6$ 0 $= P$<br>T $1/6$ $1/6$ $1/6$ |    E H T<br>E $2/13$ ▓ 0<br>H $2/13$ $2/13$ 0 $= \hat{P}$<br>T $2/13$ $2/13$ $2/13$ |
| $S_2 = \text{TEH}$ | $B_2 = \left\{\begin{array}{ccc} TT & TE & TH \\ & EE & ▓ \\ & & HH \end{array}\right\}$ |    E H T<br>E 1 1 0<br>H ▓ 1 0 $= Y$<br>T 1 1 1 |    E H T<br>E $1/6$ $1/6$ 0<br>H ▓ $1/6$ 0 $= Q$<br>T $1/6$ $1/6$ $1/6$ |    E H T<br>E $2/13$ $2/13$ 0<br>H ▓ $2/13$ 0 $= \hat{Q}$<br>T $2/13$ $2/13$ $2/13$ |

FIG. 11

| Open Bigram | First Sequence: THE | Second Sequence: TEH |
|---|---|---|
| EE | $\hat{P}_{11} = \hat{p}(\text{EE} \mid \text{THE}) = 2/13$ | $\hat{Q}_{11} = \hat{p}(\text{EE} \mid \text{TEH}) = 2/13$ |
| EH | $\hat{P}_{12} = \hat{p}(\text{EH} \mid \text{THE}) = 1/13$ | $\hat{Q}_{12} = \hat{p}(\text{EH} \mid \text{TEH}) = 2/13$ |
| ET | $\hat{P}_{13} = \hat{p}(\text{ET} \mid \text{THE}) = 0$ | $\hat{Q}_{13} = \hat{p}(\text{ET} \mid \text{TEH}) = 0$ |
| HE | $\hat{P}_{21} = \hat{p}(\text{HE} \mid \text{THE}) = 2/13$ | $\hat{Q}_{21} = \hat{p}(\text{HE} \mid \text{TEH}) = 1/13$ |
| HH | $\hat{P}_{22} = \hat{p}(\text{HH} \mid \text{THE}) = 2/13$ | $\hat{Q}_{22} = \hat{p}(\text{HH} \mid \text{TEH}) = 2/13$ |
| HT | $\hat{P}_{23} = \hat{p}(\text{HT} \mid \text{THE}) = 0$ | $\hat{Q}_{23} = \hat{p}(\text{HT} \mid \text{TEH}) = 0$ |
| TE | $\hat{P}_{31} = \hat{p}(\text{TE} \mid \text{THE}) = 2/13$ | $\hat{Q}_{31} = \hat{p}(\text{TE} \mid \text{TEH}) = 2/13$ |
| TH | $\hat{P}_{32} = \hat{p}(\text{TH} \mid \text{THE}) = 2/13$ | $\hat{Q}_{32} = \hat{p}(\text{TH} \mid \text{TEH}) = 2/13$ |
| TT | $\hat{P}_{33} = \hat{p}(\text{TT} \mid \text{THE}) = 2/13$ | $\hat{Q}_{33} = \hat{p}(\text{TT} \mid \text{TEH}) = 2/13$ |
| Sum | $\sum_i \sum_j \hat{p}(c_i c_j \mid \text{THE}) = 1.0$ | $\sum_i \sum_j \hat{p}(c_i c_j \mid \text{TEH}) = 1.0$ |

FIG. 12

| Smoothed open bigram probabilities for $S_1$=THE | Smoothed open bigram probabilities for $S_2$=TEH | Asymmetric distance $d_{KL}(S_1, S_2)$ | Asymmetric distance $d_{KL}(S_2, S_1)$ | Symmetric distance $d_{KL}^{(symm)}$ |
|---|---|---|---|---|
| $\hat{P}_{ij}$ | $\hat{Q}_{ij}$ | $\hat{P}_{ij} \log \frac{\hat{P}_{ij}}{\hat{Q}_{ij}}$ | $+ \quad \hat{Q}_{ij} \log \frac{\hat{Q}_{ij}}{\hat{P}_{ij}}$ | $\sum_i \sum_j$ |
| 2/13  1/13  0<br>2/13  2/13  0<br>2/13  2/13  2/13 | 2/13  2/13  0<br>1/13  2/13  0<br>2/13  2/13  2/13 | 0  −1/13  0<br>2/13  0    0<br>0    0    0 | + | 0  2/13  0<br>−1/13  0  0<br>0    0    0 | $\frac{2}{13}$ |

FIG. 13

|   | A | B | C |
|---|---|---|---|
| A | 1 | 1 | 0 |
| B | 0 | 1 | 0 |
| C | 1 | 1 | 1 |

FIG. 15

|   | A | B | C | row sum |
|---|---|---|---|---|
| A | 1 | 1 | 0 | 2 |
| B | 0 | 1 | 0 | 1 |
| C | 1 | 1 | 1 | 3 |
| column sum | 2 | 3 | 1 | |

FIG. 16

|   | A | B | C | D | E | row sum |
|---|---|---|---|---|---|---|
| A | 1 | 0 | 0 | 1 | 1 | 3 |
| B | 0 | 0 | 0 | 0 | 0 | 0 |
| C | 1 | 0 | 1 | 1 | 1 | 4 |
| D | 1 | 0 | 1 | 3 | 3 | 8 |
| E | 1 | 0 | 1 | 1 | 3 | 6 |
| column sum | 4 | 0 | 3 | 6 | 8 | |

| Iteration number | SSM matrix (before) | Histogram vector | SSM matrix (after) | Unrolled character |
|---|---|---|---|---|
| 1 | A B C<br>A [2 2 1]<br>B [1 3 0]<br>C [1 2 1] | − [2 2 1] = | A B C<br>A [1 1 0]<br>B [1 3 0]<br>C [1 2 1] | A |
| 2 | A B C<br>A [1 1 0]<br>B [1 3 0]<br>C [1 2 1] | − [1 2 1] = | A B C<br>A [1 1 0]<br>B [1 3 0]<br>C [0 0 0] | C |
| 3 | A B C<br>A [1 1 0]<br>B [1 2 0]<br>C [0 0 0] | − [1 2 0] = | A B C<br>A [1 1 0]<br>B [0 1 0]<br>C [0 0 0] | B |
| 4 | A B C<br>A [1 1 0]<br>B [0 1 0]<br>C [0 0 0] | − [1 1 0] = | A B C<br>A [0 0 0]<br>B [0 1 0]<br>C [0 0 0] | A |
| 5 | A B C<br>A [0 0 0]<br>B [0 1 0]<br>C [0 0 0] | − [0 1 0] = | A B C<br>A [0 0 0]<br>B [0 0 0]<br>C [0 0 0] | B |

FIG. 22

| Sequences | All Open Bigrams | Dual SSM Matrix |
|---|---|---|
| First Sequence: S I G M A<br>Second Sequence: δ ε λ τ α | Sδ Sε Sλ Sτ Sα<br>Iε Iλ Iτ Iα<br>Gλ Gτ Gα<br>Mτ Mα<br>Aα |   α δ ε λ τ<br>A 1 0 0 0 0<br>G 1 0 0 1 1<br>I 1 0 1 1 1<br>M 1 0 0 0 1<br>S 1 1 1 1 1 |

FIG. 24

| Sequences | All Open Bigrams | Dual SSM Matrix |
|---|---|---|
| First Sequence: δ ε λ τ α<br>Second Sequence: S I G M A | δS δI δG δM δA<br>εI εG εM εA<br>λG λM λA<br>τM τA<br>αA |   A G I M S<br>α 1 0 0 0 0<br>δ 1 1 1 1 1<br>ε 1 1 1 1 0<br>λ 1 1 0 1 0<br>τ 1 0 0 1 0 |

FIG. 25

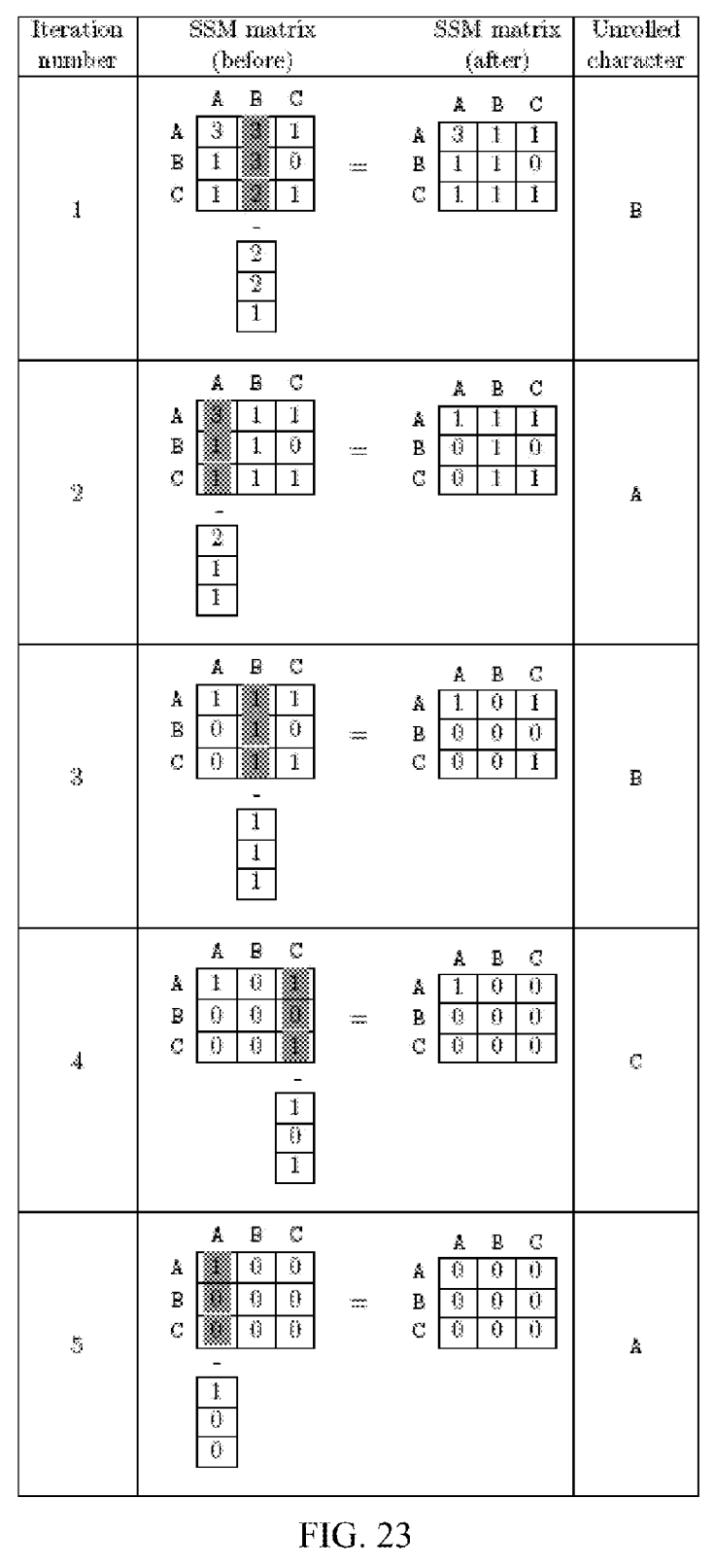

| Iteration number | SSM matrix (before) | SSM matrix (after) | Unrolled character |
|---|---|---|---|
| 1 | A B C<br>A [3, 1, 1]<br>B [1, 1, 0]<br>C [1, 1, 1]<br>-<br>[2, 2, 1] | A B C<br>A [3, 1, 1]<br>B [1, 1, 0]<br>C [1, 1, 1] | B |
| 2 | A B C<br>A [1, 1, 1]<br>B [1, 1, 0]<br>C [1, 1, 1]<br>-<br>[2, 1, 1] | A B C<br>A [1, 1, 1]<br>B [0, 1, 0]<br>C [0, 1, 1] | A |
| 3 | A B C<br>A [1, 1, 1]<br>B [0, 1, 0]<br>C [0, 1, 1]<br>-<br>[1, 1, 1] | A B C<br>A [1, 0, 1]<br>B [0, 0, 0]<br>C [0, 0, 1] | B |
| 4 | A B C<br>A [1, 0, 1]<br>B [0, 0, 0]<br>C [0, 0, 1]<br>-<br>[1, 0, 1] | A B C<br>A [1, 0, 0]<br>B [0, 0, 0]<br>C [0, 0, 0] | C |
| 5 | A B C<br>A [1, 0, 0]<br>B [0, 0, 0]<br>C [0, 0, 0]<br>-<br>[1, 0, 0] | A B C<br>A [0, 0, 0]<br>B [0, 0, 0]<br>C [0, 0, 0] | A |

FIG. 23

|        | SIGMA |    |    |    |    | δελτα |    |    |    |    |
|--------|-------|----|----|----|----|-------|----|----|----|----|
| SIGMA  | SS    | SI | SG | SM | SA | Sδ    | Sε | Sλ | Sτ | Sα |
|        |       | II | IG | IM | IA |       | Iε | Iλ | Iτ | Iα |
|        |       |    | GG | GM | GA |       |    | Gλ | Gτ | Gα |
|        |       |    |    | MM | MA |       |    |    | Mτ | Mα |
|        |       |    |    |    | AA |       |    |    |    | Aα |
| δελτα  | δS    | δI | δG | δM | δA | δδ    | δε | δλ | δτ | δα |
|        |       | εI | εG | εM | εA |       | εε | ελ | ετ | εα |
|        |       |    | λG | λM | λA |       |    | λλ | λτ | λα |
|        |       |    |    | τM | τA |       |    |    | ττ | τα |
|        |       |    |    |    | αA |       |    |    |    | αα |

FIG. 26

SIGMA

|   | A | G | I | M | S |
|---|---|---|---|---|---|
| A | 1 | 0 | 0 | 0 | 0 |
| G | 1 | 1 | 0 | 1 | 0 |
| I | 1 | 1 | 1 | 1 | 0 |
| M | 1 | 0 | 0 | 1 | 0 |
| S | 1 | 1 | 1 | 1 | 1 |

δελτα

|   | α | δ | ε | λ | τ |
|---|---|---|---|---|---|
| A | 1 | 0 | 0 | 0 | 0 |
| G | 1 | 0 | 0 | 1 | 1 |
| I | 1 | 0 | 1 | 1 | 1 |
| M | 1 | 0 | 0 | 0 | 1 |
| S | 1 | 1 | 1 | 1 | 1 |

|   | A | G | I | M | S |
|---|---|---|---|---|---|
| α | 1 | 0 | 0 | 0 | 0 |
| δ | 1 | 1 | 1 | 1 | 1 |
| ε | 1 | 1 | 1 | 1 | 0 |
| λ | 1 | 1 | 0 | 1 | 0 |
| τ | 1 | 0 | 0 | 1 | 0 |

|   | α | δ | ε | λ | τ |
|---|---|---|---|---|---|
| α | 1 | 0 | 0 | 0 | 0 |
| δ | 1 | 1 | 1 | 1 | 1 |
| ε | 1 | 0 | 1 | 1 | 1 |
| λ | 1 | 0 | 0 | 1 | 1 |
| τ | 1 | 0 | 0 | 0 | 1 |

FIG. 27

|  | DELTA | | | | | γαμμα | | | | |
|---|---|---|---|---|---|---|---|---|---|---|
| DELTA | DD | DE | DL | DT | DA | Dγ | Dα | Dμ | Dμ | Dα |
|  | EE | EL | ET | EA |  | Eα | Eμ | Eμ | Eα |  |
|  |  | LL | LT | LA |  |  | Lμ | Lμ | Lα |  |
|  |  |  | TT | TA |  |  |  | Tμ | Tα |  |
|  |  |  |  | AA |  |  |  |  | Aα |  |
| γαμμα | γD | γE | γL | γT | γA | γγ | γα | γμ | γμ | γα |
|  |  | αE | αL | αT | αA |  | αα | αμ | αμ | αα |
|  |  |  | μL | μT | μA |  |  | μμ | μμ | μα |
|  |  |  |  | μT | μA |  |  |  | μμ | μα |
|  |  |  |  |  | αA |  |  |  |  | αα |

FIG. 28

|  |  | DELTA | | | | | γαμμα | | |
|---|---|---|---|---|---|---|---|---|---|
|  |  | A | D | E | L | T | α | γ | μ |
| DELTA | A | 1 | 0 | 0 | 0 | 0 | 1 | 0 | 0 |
|  | D | 1 | 1 | 1 | 1 | 1 | 2 | 1 | 2 |
|  | E | 1 | 0 | 1 | 1 | 1 | 2 | 0 | 2 |
|  | L | 1 | 0 | 0 | 1 | 1 | 1 | 0 | 2 |
|  | T | 1 | 0 | 0 | 0 | 1 | 1 | 0 | 1 |
| γαμμα | α | 2 | 0 | 1 | 1 | 1 | 3 | 0 | 2 |
|  | γ | 1 | 1 | 1 | 1 | 1 | 2 | 1 | 2 |
|  | μ | 2 | 0 | 0 | 1 | 2 | 2 | 0 | 3 |

DELTA / DELTA

|   | A | D | E | L | T |
|---|---|---|---|---|---|
| A | 1 | 0 | 0 | 0 | 0 |
| D | 1 | 1 | 1 | 1 | 1 |
| E | 1 | 0 | 1 | 1 | 1 |
| L | 1 | 0 | 0 | 1 | 1 |
| T | 1 | 0 | 0 | 0 | 1 |

DELTA / 31415

|   | 1 | 3 | 4 | 5 |
|---|---|---|---|---|
| A | 0 | 0 | 0 | 1 |
| D | 2 | 1 | 1 | 1 |
| E | 2 | 0 | 1 | 1 |
| L | 1 | 0 | 1 | 1 |
| T | 1 | 0 | 0 | 1 |

DELTA / γαμμα

|   | α | γ | μ |
|---|---|---|---|
| A | 1 | 0 | 0 |
| D | 2 | 1 | 2 |
| E | 2 | 0 | 2 |
| L | 1 | 0 | 2 |
| T | 1 | 0 | 1 |

31415 / DELTA

|   | A | D | E | L | T |
|---|---|---|---|---|---|
| 1 | 2 | 0 | 1 | 1 | 2 |
| 3 | 1 | 1 | 1 | 1 | 1 |
| 4 | 1 | 0 | 0 | 1 | 1 |
| 5 | 1 | 0 | 0 | 0 | 0 |

31415 / 31415

|   | 1 | 3 | 4 | 5 |
|---|---|---|---|---|
| 1 | 3 | 0 | 1 | 2 |
| 3 | 2 | 1 | 1 | 1 |
| 4 | 1 | 0 | 1 | 1 |
| 5 | 0 | 0 | 0 | 1 |

31415 / γαμμα

|   | α | γ | μ |
|---|---|---|---|
| 1 | 3 | 0 | 3 |
| 3 | 2 | 1 | 2 |
| 4 | 1 | 0 | 2 |
| 5 | 1 | 0 | 0 |

γαμμα / DELTA

|   | A | D | E | L | T |
|---|---|---|---|---|---|
| α | 2 | 0 | 1 | 1 | 1 |
| γ | 1 | 1 | 1 | 1 | 1 |
| μ | 2 | 0 | 0 | 1 | 2 |

γαμμα / 31415

|   | 1 | 3 | 4 | 5 |
|---|---|---|---|---|
| α | 2 | 0 | 1 | 2 |
| γ | 2 | 1 | 1 | 1 |
| μ | 2 | 0 | 1 | 2 |

γαμμα / γαμμα

|   | α | γ | μ |
|---|---|---|---|
| α | 3 | 0 | 2 |
| γ | 2 | 1 | 2 |
| μ | 2 | 0 | 3 |

FIG. 31

$$\boxed{X(S),\ h(S)} \longrightarrow S$$

FIG. 32

$$\boxed{h(S'),\ h(S''),\ X(S'),\ X(S''),\ D(S',\ S''),\ D(S'',\ S')} \longrightarrow S'$$

$$\boxed{h(S'),\ h(S''),\ X(S'),\ X(S''),\ D(S',\ S''),\ D(S'',\ S')} \longrightarrow S''$$

FIG. 33

$$\boxed{h(S'),\ h(S''),\ X(S'),\ X(S''),\ D(S',\ S''),\ D(S'',\ S')} \longrightarrow \frac{S'}{S''}$$

FIG. 34

$$S'' \longrightarrow \boxed{D(S',\ S''),\ h(S'')} \longrightarrow S'$$

FIG. 35

$$S' \longrightarrow \boxed{D(S'',\ S'),\ h(S')} \longrightarrow S''$$

| Iteration # | Sequences | All Open Bigrams | Histogram Vector $h'$ | Dual Matrix $D(S',S'')$ |
|---|---|---|---|---|
| Initialization | | | α 0<br>β 0<br>γ 0 |    A B<br>α 0 0<br>β 0 0<br>γ 0 0 |
| First | $S' = \beta$<br>$S'' = A$ | βA | α 0<br>β 1<br>γ 0 |    A B<br>α 0 0<br>β 1 0<br>γ 0 0 |
| Second | $S' = \beta\alpha$<br>$S'' = AB$ | βA  βB<br>αB | α 1<br>β 1<br>γ 0 |    A B<br>α 0 1<br>β 1 1<br>γ 0 0 |
| Third | $S' = \beta\alpha\gamma$<br>$S'' = ABA$ | βA  βB  βA<br>αB  αA<br>γA | α 1<br>β 1<br>γ 1 |    A B<br>α 1 1<br>β 2 1<br>γ 1 0 |
| Fourth | $S' = \beta\alpha\gamma\blacksquare$<br>$S'' = ABA\blacksquare$ | βA  βB  βA  ▒<br>αB  αA  ▒<br>γA  ▒<br>▒ | α 1<br>β ▒<br>γ 1 |    A B<br>α 1 ▒<br>β 2 ▒<br>γ 1 ▒ |

FIG. 36

| Dual Matrix $D(S',S'')$ | Histogram Vector $h'$ | Histogram Vector $h''$ |
|---|---|---|
|    A B<br>α 1 2<br>β 2 3<br>γ 1 1 | α 1<br>β 2<br>γ 1 | A B<br>2 2 |

FIG. 37

| Iteration # | Sequences | All Open Bigrams | Histogram Vector $h'$ | Dual Matrix $D(S', S'')$ |
|---|---|---|---|---|
| Initialization | | | α [0]<br>β [0]<br>γ [0] |    A  B<br>α [0][0]<br>β [0][0]<br>γ [0][0] |
| First | $S' = \beta$<br>$S'' = \text{B}$ | βB | α [0]<br>β [1]<br>γ [0] |    A  B<br>α [0][0]<br>β [0][1]<br>γ [0][0] |
| Second | $S' = \beta\alpha$<br>$S'' = \text{BB}$ | βB   βB<br>αB | α [1]<br>β [1]<br>γ [0] |    A  B<br>α [0][1]<br>β [0][2]<br>γ [0][0] |
| Third | $S' = \beta\alpha\gamma$<br>$S'' = \text{BBB}$ | βB   βB   βB<br>αB   αB<br>γB | α [1]<br>β [1]<br>γ [1] |    A  B<br>α [0][2]<br>β [0][3]<br>γ [0][1] |
| Fourth | $S' = \beta\alpha\gamma$▨<br>$S'' = \text{BBB}$▨ | βB   βB   βB   ▨<br>αB   αB   ▨<br>γB   ▨ | α [1]<br>β ▨<br>γ [1] |    A  B<br>α ▨[2]<br>β ▨[3]<br>γ ▨[1] |

FIG. 38

| Dual Matrix $D(S', S'')$ | Histogram Vector $h'$ | Histogram Vector $h''$ |
|---|---|---|
|    A  B<br>α [1][2]<br>β [2][3]<br>γ [1][1] | α [1]<br>β [2]<br>γ [1] | A  B<br>[1][3] |

FIG. 39

| Dual Matrix $D(S', S'')$ | Histogram Vector $h''$ |
|---|---|
|    A  B<br>α [1][2]<br>β [2][3]<br>γ [1][1] | A  B<br>[2][2] |

| Iteration number | Input Sequence $S''$ | Dual matrix (before) | Histogram vector $h''$ | Dual matrix (after) | Output Sequence $S'$ |
|---|---|---|---|---|---|
| 1 | B | A B<br>α 1 2<br>β 2 3<br>γ 1 1 | A B<br>1 3 | A B<br>α 1 2<br>β 1 0<br>γ 1 1 | β |
| 2 | BB | A B<br>α 1 2<br>β 1 0<br>γ 1 1 | A B<br>1 2 | A B<br>α 0 0<br>β 1 0<br>γ 1 1 | βα |
| 3 | BBB | A B<br>α 0 0<br>β 1 0<br>γ 1 1 | A B<br>1 1 | A B<br>α 0 0<br>β 1 0<br>γ 0 0 | βαγ |
| 4 | BBB▓ | A B<br>α 0 0<br>▓▓▓▓▓<br>γ 0 0 | ▓ B<br>0 | A B<br>α 0 0<br>β 0 0<br>γ 0 0 | βαγ▓ |

FIG. 44

$S'' = BBBA$ ⟹

| Dual SSM Model | |
|---|---|
| Dual Matrix $D(S', S'')$ | Histogram Vector $h''$ |
| A B<br>α 1 2<br>β 2 3<br>γ 1 1 | A B<br>1 3 |

| Iteration number | Input Sequence $S''$ | Dual matrix (before) | Histogram vector $h''$ | Dual matrix (after) | Output Sequence $S'$ |
|---|---|---|---|---|---|
| 1 | D | α: A=2, D=0, E=1, L=1, T=1<br>γ: A=1, D=1, E=1, L=1, T=1<br>μ: A=2, D=0, E=0, L=1, T=2 | − A=1, D=1, E=1, L=1, T=1 = | α: A=2, D=0, E=1, L=1, T=1<br>γ: A=0, D=0, E=0, L=0, T=0<br>μ: A=2, D=0, E=0, L=1, T=2 | γ |
| 2 | DE | α: A=2, D=0, E=1, L=1, T=1<br>γ: A=0, D=0, E=0, L=0, T=0<br>μ: A=2, D=0, E=0, L=1, T=2 | − A=1, D=0, E=1, L=1, T=1 = | α: A=1, D=0, E=0, L=0, T=0<br>γ: A=0, D=0, E=0, L=0, T=0<br>μ: A=2, D=0, E=0, L=1, T=2 | γα |
| 3 | DEL | α: A=1, D=0, E=0, L=0, T=0<br>γ: A=0, D=0, E=0, L=0, T=0<br>μ: A=2, D=0, E=0, L=1, T=2 | − A=1, D=0, E=0, L=1, T=1 = | α: A=1, D=0, E=0, L=0, T=0<br>γ: A=0, D=0, E=0, L=0, T=0<br>μ: A=1, D=0, E=0, L=0, T=1 | γαμ |
| 4 | DELT | α: A=1, D=0, E=0, L=0, T=0<br>γ: A=0, D=0, E=0, L=0, T=0<br>μ: A=1, D=0, E=0, L=0, T=1 | − A=1, D=0, E=0, L=0, T=1 = | α: A=0, D=0, E=0, L=0, T=0<br>γ: A=0, D=0, E=0, L=0, T=0<br>μ: A=0, D=0, E=0, L=0, T=0 | γαμ |
| 5 | DELT▒ | α: ▒▒▒▒▒<br>γ: A=0, D=0, E=0, L=0, T=0<br>μ: A=0, D=0, E=0, L=0, T=0 | − ▒ D=0, E=0, L=0, T=0 = | α: A=0, D=0, E=0, L=0, T=0<br>γ: A=0, D=0, E=0, L=0, T=0<br>μ: A=0, D=0, E=0, L=0, T=0 | γαμ▒ |

FIG. 46

| Iteration number | Input Sequence $(S^c)^R$ | Dual matrix (before) | | Dual matrix (after) | Output Sequence $(S^d)^B$ |
|---|---|---|---|---|---|
| 1 | α | A D E L T<br>α [2 0 1 1 1]<br>γ [1 1 1 1 1]<br>μ [2 0 0 1 2]<br>-<br>α [2]<br>γ [1]<br>μ [2] | = | A D E L T<br>α [0 0 1 1 1]<br>γ [0 1 1 1 1]<br>μ [0 0 0 1 2] | A |
| 2 | αμ | A D E L T<br>α [0 0 1 1 1]<br>γ [0 1 1 1 1]<br>μ [0 0 0 1 2]<br>-<br>α [1]<br>γ [1]<br>μ [2] | = | A D E L T<br>α [0 0 1 1 0]<br>γ [0 1 1 1 0]<br>μ [0 0 0 1 0] | AT |
| 3 | αμμ | A D E L T<br>α [0 0 1 1 0]<br>γ [0 1 1 1 0]<br>μ [0 0 0 1 0]<br>-<br>α [1]<br>γ [1]<br>μ [1] | = | A D E L T<br>α [0 0 1 0 0]<br>γ [0 1 1 0 0]<br>μ [0 0 0 0 0] | ATL |
| 4 | αμμα | A D E L T<br>α [0 0 1 0 0]<br>γ [0 1 1 0 0]<br>μ [0 0 0 0 0]<br>-<br>α [1]<br>γ [1]<br>μ [0] | = | A D E L T<br>α [0 0 0 0 0]<br>γ [0 1 0 0 0]<br>μ [0 0 0 0 0] | ATLE |
| 5 | αμμα▓ | A ▓ E L T<br>α [0 ▓ 0 0 0]<br>γ [0 ▓ 0 0 0]<br>μ [0 ▓ 0 0 0]<br>-<br>α [0]<br>▓<br>μ [0] | = | A D E L T<br>α [0 0 0 0 0]<br>γ [0 0 0 0 0]<br>μ [0 0 0 0 0] | ATLE▓ |

FIG. 47

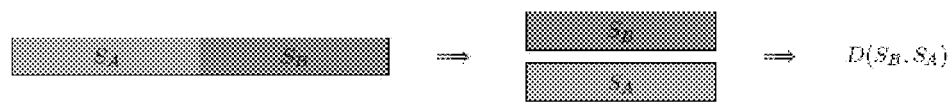

FIG. 48

$$S_A \longrightarrow \boxed{D(S_B, S_A), h(S_A)} \longrightarrow S_B$$

FIG. 49

First sequence $S'$: | $S'_A$ | $S'_B$ |

Second sequence $S''$: | $S''_A$ | $S''_B$ |

FIG. 50

$$S'_A \longrightarrow \boxed{D(S''_A, S'_A), h(S'_A)} \longrightarrow S''_A \longrightarrow \boxed{D(S'_B, S''_A), h(S''_A)} \longrightarrow S'_B$$

FIG. 51

First Sequence: | α | β | γ |
Second Sequence: | A | B | C | D | E | F |

FIG. 52

| αA  αB  αC  αD  αE  αF<br>βC  βD  βE  βF<br>γE  γF | αB  αC  αD  αE  αF<br>βD  βE  βF<br>γF | αC  αD  αE  αF<br>βE  βF |

FIG. 53

| Sequence | All Open Trigrams | All Regular Trigrams |
|---|---|---|
| ABCD | AAA  AAB  AAC  AAD<br>ABB  ABC  ABD<br>BBB  BBC  BBD<br>ACC  ACD<br>BCC  BCD<br>CCC  CCD<br>ADD<br>BDD<br>CDD<br>DDD | ABC  BCD |

FIG. 54

| Sequence length | Number of regular bigrams | Number of regular trigrams | Number of open bigrams | Number of open trigrams |
|---|---|---|---|---|
| 1 | N/A | N/A | 1 | 1 |
| 2 | 1 | N/A | 3 | 4 |
| 3 | 2 | 1 | 6 | 10 |
| 4 | 3 | 2 | 10 | 20 |
| 5 | 4 | 3 | 15 | 35 |
| 10 | 9 | 8 | 55 | 220 |
| 100 | 99 | 98 | 5,050 | 171,700 |
| $T$ | $T-1$ | $T-2$ | $\dfrac{T(T+1)}{2}$ | $\dfrac{T(T+1)(T+2)}{3!}$ |

| Iteration # | Sequence | All Open Bigrams | All Open Trigrams | Character Histogram | # Of Open Bigrams | # Of Open Trigrams |
|---|---|---|---|---|---|---|
| Initialization | | | | $A\begin{bmatrix}0\\0\end{bmatrix}$ B | A B<br>A [0 0]<br>B [0 0] | A B<br>A [0 0] A<br>B [0 0]<br>A [0 0] B<br>B [0 0] |
| First | A | AA | AAA | $A\begin{bmatrix}1\\0\end{bmatrix}$ B | A B<br>A [1 0]<br>B [0 0] | A B<br>A [1 0] A<br>B [0 0]<br>A [0 0] B<br>B [0 0] |
| Second | AB | AA AB<br>BB | AAA AAB<br>ABB<br>BBB | $A\begin{bmatrix}1\\1\end{bmatrix}$ B | A B<br>A [1 1]<br>B [0 1] | A B<br>A [1 0] A<br>B [0 0]<br>A [1 1] B<br>B [0 1] |
| Third | ABB | AA AB AB<br>BB BB<br>BB | AAA AAB AAB<br>ABB ABB<br>BBB BBB<br>ABB<br>BBB<br>BBB | $A\begin{bmatrix}1\\2\end{bmatrix}$ B | A B<br>A [1 2]<br>B [0 3] | A B<br>A [1 0] A<br>B [0 0]<br>A [2 3] B<br>B [0 4] |
| Fourth | ABB▓ | AA AB AB ▓<br>BB BB ▓<br>BB ▓ | AAA AAB AAB ▓<br>ABB ABB ▓<br>BBB BBB ▓<br>ABB ▓<br>BBB ▓<br>BBB ▓<br>▓<br>▓<br>▓ | $A\begin{bmatrix}▓\\2\end{bmatrix}$ B | A B<br>A [▓ 2]<br>B [▓ 3] | A B<br>A [▓ ▓] A<br>B<br>A [2 3] B<br>B [0 4] |

FIG. 57

| Sequence | Open Bigrams in ABBA | | | | SSM Matrix | | | Open Bigrams in BAAB | | | | Sequence |
|---|---|---|---|---|---|---|---|---|---|---|---|---|
| ABBA | AA | AB | AB | AA | | A | B | BB | BA | BA | BB | BAAB |
| | | BB | BB | BA | A | 2 | 2 | | AA | AA | AB | |
| | | | BB | BA | B | 2 | 3 | | | AA | AB | |
| | | | | AA | | | | | | | BB | |

FIG. 58

| Sequence | All Open Trigrams | | | SSM Representation |
|---|---|---|---|---|
| ABBA | AAA AAB AAB AAA<br>ABB ABB ABA<br>BBB BBB BBA<br>ABB ABA<br>BBB BBA<br>BBB BBA<br>AAA<br>BAA<br>BAA<br>AAA | | | A B<br>A [4] [2] A<br>B [2] [3]<br>A [2] [3] B<br>B [0] [4] |
| BAAB | BBB BBA BBA BBB<br>BAA BAA BAB<br>AAA AAA AAB<br>BAA BAB<br>AAA AAB<br>AAA AAB<br>BBB<br>ABB<br>ABB<br>BBB | | | A B<br>A [4] [0] A<br>B [3] [2]<br>A [3] [2] B<br>B [2] [4] |

FIG. 59

| Sequences | All Open Trigrams | | | | SSM Representation |
|---|---|---|---|---|---|
| $S_1 =$ ABCA $S_2 =$ 1234 $S_3 =$ αβαβ | A1α A2β B2β | A1β A2α B2α A3α B3α C3α | A1α A2β B2β A3β B3β C3β A4β B4β C4β A4β | | <table><tr><td></td><td>1</td><td>2</td><td>3</td><td>4</td><td></td></tr><tr><td>A</td><td>2</td><td>1</td><td>1</td><td>0</td><td rowspan="3">α</td></tr><tr><td>B</td><td>0</td><td>1</td><td>1</td><td>0</td></tr><tr><td>C</td><td>0</td><td>0</td><td>1</td><td>0</td></tr><tr><td>A</td><td>2</td><td>2</td><td>1</td><td>2</td><td rowspan="3">β</td></tr><tr><td>B</td><td>0</td><td>2</td><td>1</td><td>1</td></tr><tr><td>C</td><td>0</td><td>0</td><td>1</td><td>1</td></tr></table> |

FIG. 60

| Sequences | All Open Trigrams | | | | SSM Representation |
|---|---|---|---|---|---|
| $S_1 =$ 1234 $S_2 =$ ABCA $S_3 =$ αβαβ | 1Aα 1Bβ 2Bβ | 1Aβ 1Bα 2Bα 1Cα 2Cα 3Cα | 1Aα 1Bβ 2Bβ 1Cβ 2Cβ 3Cβ 1Aβ 2Aβ 3Aβ 4Aβ | | <table><tr><td></td><td>A</td><td>B</td><td>C</td><td></td></tr><tr><td>1</td><td>2</td><td>1</td><td>1</td><td rowspan="4">α</td></tr><tr><td>2</td><td>0</td><td>1</td><td>1</td></tr><tr><td>3</td><td>0</td><td>0</td><td>1</td></tr><tr><td>4</td><td>0</td><td>0</td><td>0</td></tr><tr><td>1</td><td>3</td><td>2</td><td>1</td><td rowspan="4">β</td></tr><tr><td>2</td><td>1</td><td>2</td><td>1</td></tr><tr><td>3</td><td>1</td><td>0</td><td>1</td></tr><tr><td>4</td><td>1</td><td>0</td><td>0</td></tr></table> |

FIG. 61

| Iteration # | Sequence | All Open Bigrams | Histogram Vector | SSM Matrix |
|---|---|---|---|---|
| Initialization | | | A 0.000<br>B 0.000 |     A     B<br>A 0.000 0.000<br>B 0.000 0.000 |
| First | A | AA | A 1.000<br>B 0.000 |     A     B<br>A 1.000 0.000<br>B 0.000 0.000 |
| Second | AB | AA AB<br>BB | A 0.500<br>B 1.000 |     A     B<br>A 1.000 0.500<br>B 0.000 1.000 |
| Third | ABA | AA AB AA<br>BB BA<br>AA | A 1.250<br>B 0.500 |     A     B<br>A 2.250 0.500<br>B 0.500 1.000 |
| Fourth | ABAB | AA AB AA AB<br>BB BA BB<br>AA AB<br>BB | A 0.625<br>B 1.250 |     A     B<br>A 2.250 1.125<br>B 0.500 2.250 |

FIG. 62

| | ABBA | BAAB |
|---|---|---|
| Linear |     A  B<br>A 3  2<br>B 2  3 |     A  B<br>A 3  2<br>B 2  3 |
| Exponential |     A     B<br>A 2.125 0.750<br>B 0.750 2.500 |     A     B<br>A 2.500 0.750<br>B 0.750 2.125 |

FIG. 63

| Iteration # | Sequence | All Open Bigrams | Histogram Vector | SSM Matrix |
|---|---|---|---|---|
| Initialization | | | A 0.000<br>B 0.000<br>C 0.000 |    A     B     C<br>A 0.000 0.000 0.000<br>B 0.000 0.000 0.000<br>C 0.000 0.000 0.000 |
| First | A | AA | A 1.000<br>B 0.000<br>C 0.000 |    A     B     C<br>A 1.000 0.000 0.000<br>B 0.000 0.000 0.000<br>C 0.000 0.000 0.000 |
| Second | AC | AA  AC<br>     CC | A 0.500<br>B 0.000<br>C 1.000 |    A     B     C<br>A 1.000 0.000 0.500<br>B 0.000 0.000 0.000<br>C 0.000 0.000 1.000 |
| Third | ACB | AA  AC  AB<br>     CC  CB<br>          BB | A 0.250<br>B 1.000<br>C 0.500 |    A     B     C<br>A 1.000 0.250 0.500<br>B 0.000 1.000 0.000<br>C 0.000 0.500 1.000 |
| Fourth | ACBA | AA  AC  AB  AA<br>     CC  CB  CA<br>          BB  BA<br>               AA | A 1.125<br>B 0.500<br>C 0.250 |    A     B     C<br>A 2.125 0.250 0.500<br>B 0.500 1.000 0.000<br>C 0.250 0.500 1.000 |
| Fifth | ACBA▒ | AA  AC  AB  AA  ▒<br>     CC  CB  CA  ▒<br>          BB  BA  ▒<br>               AA  ▒<br>                     ▒ | A ▒<br>B ▒<br>C ▒ |    A     B     C<br>A 2.125 ▒ 0.500<br>B 0.500 ▒ 0.000<br>C 0.250 ▒ 1.000 |

FIG. 64

| Iteration number | SSM matrix (before) | SSM matrix (after) | Unrolled character |
|---|---|---|---|
| 1 | A B<br>A [2.250] [░░░]<br>B [0.500] [░░░]<br>-<br>[0.625]<br>[1.250] | A B<br>A [2.250] [0.500]<br>B [0.500] [1.000] | B |
| 2 | A B<br>A [░░░] [0.500]<br>B [░░░] [1.000]<br>-<br>[1.250]<br>[0.500] | A B<br>A [1.000] [0.500]<br>B [0.000] [1.000] | A |
| 3 | A B<br>A [1.000] [░░░]<br>B [0.000] [░░░]<br>-<br>[0.500]<br>[1.000] | A B<br>A [1.000] [0.000]<br>B [0.000] [0.000] | B |
| 4 | A B<br>A [░░░] [0.000]<br>B [░░░] [0.000]<br>-<br>[1.000]<br>[0.000] | A B<br>A [0.000] [0.000]<br>B [0.000] [0.000] | A |

FIG. 65

| Iteration number | SSM matrix (before) | Histogram vector h | SSM matrix (after) | Unrolled character |
|---|---|---|---|---|
| 1 | A B<br>A [░░░] [░░░]<br>B [0.500] [2.250] | A B<br>[0.625] [1.250] | The histogram vector can't be subtracted from any row of the matrix | ? |

FIG. 66

| Iteration number | SSM matrix (before) | | | Histogram vector h* | | | SSM matrix (after) | | | Unrolled character |
|---|---|---|---|---|---|---|---|---|---|---|
| | | A | B | | A | B | | A | B | |
| 1 | A | ▓▓▓ | ▓▓▓ | − | 1.250 | 0.625 | = | A 1.000 | 0.500 | A |
| | B | 0.500 | 2.250 | | | | | B 0.500 | 2.250 | |
| 2 | A | 1.000 | 0.500 | − | 0.500 | 1.250 | = | A 1.000 | 0.500 | B |
| | B | ▓▓▓ | ▓▓▓ | | | | | B 0.000 | 1.000 | |
| 3 | A | ▓▓▓ | ▓▓▓ | − | 1.000 | 0.500 | = | A 0.000 | 0.000 | A |
| | B | 0.000 | 1.000 | | | | | B 0.000 | 1.000 | |
| 4 | A | 0.000 | 0.000 | − | 0.000 | 1.000 | = | A 0.000 | 0.000 | B |
| | B | ▓▓▓ | ▓▓▓ | | | | | B 0.000 | 0.000 | |

FIG. 67

| Iteration number | SSM matrix (before) | | | | Histogram vector h* | | | | SSM matrix (after) | | | | Unrolled character |
|---|---|---|---|---|---|---|---|---|---|---|---|---|---|
| | | A | B | C | | A | B | C | | A | B | C | |
| 1 | A | ▓▓▓ | ▓▓▓ | ▓▓▓ | − | 1.125 | 0.3125 | 0.500 | = | A 1.000 | 0.500 | 0.000 | A |
| | B | 0.500 | 2.250 | 0.000 | | | | | | B 0.500 | 2.250 | 0.000 | |
| | C | 0.250 | 0.6250 | 1.000 | | | | | | C 0.250 | 0.625 | 1.000 | |
| 2 | A | 1.000 | 0.500 | 0.000 | − | 0.250 | 0.625 | 1.000 | = | A 1.000 | 0.500 | 0.000 | C |
| | B | 0.500 | 2.250 | 0.000 | | | | | | B 0.500 | 2.250 | 0.000 | |
| | C | ▓▓▓ | ▓▓▓ | ▓▓▓ | | | | | | C 0.000 | 0.000 | 0.000 | |
| 3 | A | 1.000 | 0.500 | 0.000 | − | 0.500 | 1.250 | 0.000 | = | A 1.000 | 0.500 | 0.000 | B |
| | B | ▓▓▓ | ▓▓▓ | ▓▓▓ | | | | | | B 0.000 | 1.000 | 0.000 | |
| | C | 0.000 | 0.000 | 0.000 | | | | | | C 0.000 | 0.000 | 0.000 | |
| 4 | A | ▓▓▓ | ▓▓▓ | ▓▓▓ | − | 1.000 | 0.500 | 0.000 | = | A 0.000 | 0.000 | 0.000 | A |
| | B | 0.000 | 1.000 | 0.000 | | | | | | B 0.000 | 1.000 | 0.000 | |
| | C | 0.000 | 0.000 | 0.000 | | | | | | C 0.000 | 0.000 | 0.000 | |
| 5 | A | 0.000 | 0.000 | 0.000 | − | 0.000 | 1.000 | 0.000 | = | A 0.000 | 0.000 | 0.000 | B |
| | B | ▓▓▓ | ▓▓▓ | ▓▓▓ | | | | | | B 0.000 | 0.000 | 0.000 | |
| | C | 0.000 | 0.000 | 0.000 | | | | | | C 0.000 | 0.000 | 0.000 | |

FIG. 68

| Iteration number | SSM matrix (before) | | | Histogram vector $h$ | | | SSM matrix (after) | Unrolled character |
|---|---|---|---|---|---|---|---|---|
| | | A | B | C | | | | | |
| 1 | A | | | | ? A B C | | | The histogram vector can't be subtracted from any row of the matrix | ? |
| | B | 0.500 | 2.2500 | 0.000 | - 0.5625 | 1.2500 | 0.1250 | | |
| | C | 0.250 | 0.6250 | 1.000 | | | | | |

FIG. 69

| Iteration number | SSM matrix (before) | | SSM matrix (after) | Unrolled character |
|---|---|---|---|---|
| 1 | A B C<br>A 2.125 0.8125 0.500<br>B 0.500 2.2500 0.000<br>C 0.250 0.6250 1.000<br>-<br>0.5625<br>1.2500<br>0.1250 | = | A B C<br>A 2.125 0.250 0.500<br>B 0.500 1.000 0.000<br>C 0.250 0.500 1.000 | B |
| 2 | A B C<br>A 2.125 0.250 0.500<br>B 0.500 1.000 0.000<br>C 0.250 0.500 1.000<br>-<br>1.125<br>0.500<br>0.250 | = | A B C<br>A 1.000 0.250 0.500<br>B 0.000 1.000 0.000<br>C 0.000 0.500 1.000 | A |
| 3 | A B C<br>A 1.000 0.250 0.500<br>B 0.000 1.000 0.000<br>C 0.000 0.500 1.000<br>-<br>0.250<br>1.000<br>0.500 | = | A B C<br>A 1.000 0.000 0.500<br>B 0.000 0.000 0.000<br>C 0.000 0.000 1.000 | B |
| 4 | A B C<br>A 1.000 0.000 0.500<br>B 0.000 0.000 0.000<br>C 0.000 0.000 1.000<br>-<br>0.500<br>0.000<br>1.000 | = | A B C<br>A 1.000 0.000 0.000<br>B 0.000 0.000 0.000<br>C 0.000 0.000 0.000 | C |
| 5 | A B C<br>A 1.000 0.000 0.000<br>B 0.000 0.000 0.000<br>C 0.000 0.000 0.000<br>-<br>1.000<br>0.000<br>0.000 | = | A B C<br>A 0.000 0.000 0.000<br>B 0.000 0.000 0.000<br>C 0.000 0.000 0.000 | A |

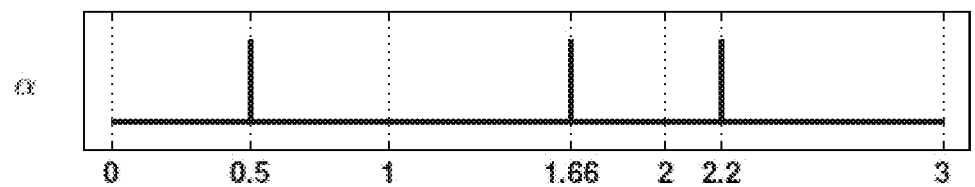
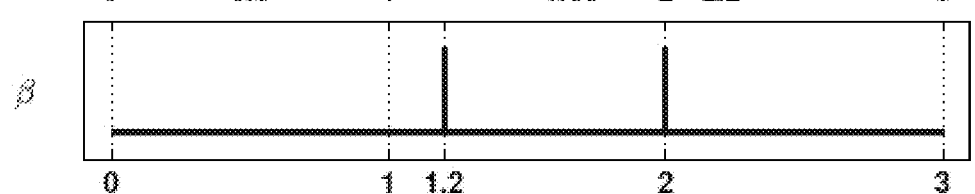
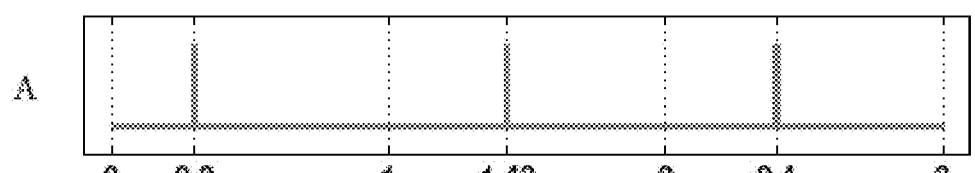
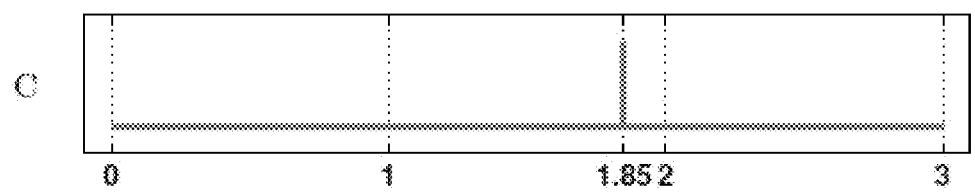
FIG. 75

FIG. 87

| Word\Feature | Speaker 1 | | | Speaker 2 | | | Speaker 3 | | Speaker 4 | |
|---|---|---|---|---|---|---|---|---|---|---|
| | water | wash | year | water | year | wash | water | curry | water | greasy |
| 0 | 0.00 | 3.84 | 3.47 | 4.18 | 3.85 | 6.24 | 1.85 | 5.24 | 1.47 | 4.11 |
| 1 | 0.00 | 3.41 | 3.75 | 4.10 | 4.42 | 5.66 | 0.97 | 5.92 | 1.41 | 6.20 |
| 2 | 0.00 | 1.94 | 3.59 | 4.51 | 8.53 | 7.67 | 0.51 | 9.30 | 5.57 | 4.53 |
| 3 | 0.00 | 4.54 | 9.83 | 0.29 | 9.37 | 5.17 | 0.19 | 8.59 | 0.65 | 8.03 |
| 4 | 0.00 | 1.30 | 9.27 | 2.28 | 12.82 | 2.98 | 0.88 | 4.34 | 3.62 | 8.73 |
| 5 | 0.00 | 2.02 | 4.78 | 1.41 | 2.99 | 2.60 | 3.89 | 3.50 | 3.16 | 4.81 |
| 6 | 0.00 | 2.67 | 5.88 | 1.52 | 4.44 | 2.22 | 4.67 | 6.43 | 1.59 | 1.58 |
| 7 | 0.00 | 5.10 | 3.36 | 0.85 | 2.50 | 2.36 | 2.03 | 2.55 | 3.30 | 2.64 |
| 8 | 0.00 | 1.76 | 5.59 | 0.43 | 11.39 | 1.25 | 2.27 | 3.01 | 3.04 | 5.57 |
| 9 | 0.00 | 2.05 | 7.70 | 4.45 | 10.01 | 2.88 | 0.46 | 4.08 | 3.39 | 8.97 |
| 10 | 0.00 | 0.93 | 6.00 | 4.41 | 5.14 | 1.75 | 1.75 | 1.02 | 0.79 | 2.82 |
| 11 | 0.00 | 2.27 | 2.53 | 0.44 | 0.97 | 1.14 | 3.14 | 1.22 | 1.37 | 2.62 |
| 12 | 0.00 | 2.33 | 9.57 | 4.51 | 8.20 | 7.26 | 3.39 | 3.54 | 1.22 | 6.28 |
| Sum | 0.00 | 34.15 | 75.33 | 33.37 | 84.64 | 49.15 | 25.99 | 49.73 | 30.57 | 66.87 |
| Closest | | | | X | | | X | | X | |

FIG. 88

| Word \ Feature | Speaker 1 | | | Speaker 2 | | | Speaker 3 | | Speaker 4 | |
|---|---|---|---|---|---|---|---|---|---|---|
| | water | wash | year | water | year | wash | water | carry | water | greasy |
| 1 | 0.00 | | | | | | | | | |
| 2 | 0.00 | | | | | | | | | |
| 3 | 0.00 | | | | | | | | | |
| ... | ... | ... | ... | ... | ... | ... | ... | ... | ... | ... |
| 168 | 0.00 | | | | | | | | | |
| 169 | 0.00 | | | | | | | | | |
| Sum | 0.00 | 456.42 | 1044.30 | 458.16 | 1241.11 | 691.95 | 345.06 | 707.93 | 427.34 | 934.09 |
| Closest | | X | | | | | X | | X | |

FIG. 93

| Sequence | All Open Bigrams | SSM Matrix |
|---|---|---|
| GATTACA | GG GA GT GT GA GC GA<br>AA AT AT AA AC AA<br>TT TT TA TC TA<br>TT TA TC TA<br>AA AC AA<br>CC CA<br>AA |   A T G C<br>A 6 2 0 2<br>T 4 3 0 2<br>G 3 2 1 1<br>C 1 0 0 1 |

FIG. 94

MQVRAVLVLAVVALVAVATSRAQLNFTP
WWGKRALGAPAAGDCVSASPQALLSI
LNAAQAEVQKLIDCSRFTSEANS

ADIPOKINETIC HORMONE III PRECURSOR

Class: secretory pathway/signal peptide (SP)

FIG. 95

A = Alanine           N = Asparagine
C = Cysteine          P = Proline
D = Aspartic Acid     Q = Glutamine
E = Glutamic Acid     R = Arginine
F = Phenylalanine     S = Serine
G = Glycine           T = Threonine
H = Histidine         V = Valine
I = Isoleucine        W = Tryptophan
K = Lysine            X = Unspecified
L = Leucine           Y = Tyrosine
M = Methionine        Z = Glutamine
FIG. 96
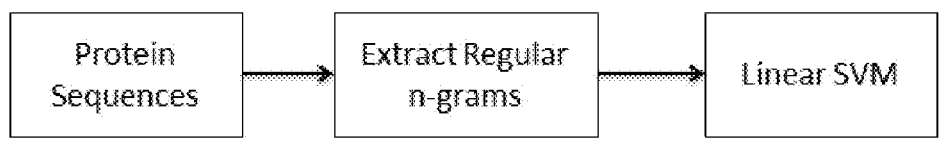
FIG. 97
FIG. 98

|   | A | C | D | E | F | G | H | I | K | L | M | N | P | Q | R | S | T | V | W | X | Y | Z |
|---|---|---|---|---|---|---|---|---|---|---|---|---|---|---|---|---|---|---|---|---|---|---|
| A | 127 | 21 | 22 | 23 | 16 | 23 | 0 | 24 | 19 | 66 | 0 | 28 | 25 | 43 | 21 | 69 | 21 | 36 | 12 | 0 | 0 | 0 |
| C | 7 | 3 | 1 | 3 | 2 | 0 | 0 | 2 | 1 | 4 | 0 | 3 | 1 | 3 | 2 | 9 | 2 | 2 | 0 | 0 | 0 | 0 |
| D | 7 | 3 | 3 | 3 | 2 | 0 | 0 | 2 | 1 | 4 | 0 | 3 | 1 | 3 | 2 | 9 | 2 | 2 | 0 | 0 | 0 | 0 |
| E | 2 | 1 | 1 | 3 | 1 | 0 | 0 | 1 | 1 | 1 | 0 | 2 | 0 | 1 | 1 | 4 | 1 | 1 | 0 | 0 | 0 | 0 |
| F | 11 | 2 | 2 | 3 | 3 | 3 | 0 | 2 | 2 | 5 | 0 | 3 | 3 | 3 | 2 | 8 | 3 | 2 | 2 | 0 | 0 | 0 |
| G | 25 | 6 | 6 | 6 | 3 | 6 | 0 | 6 | 4 | 13 | 0 | 6 | 5 | 9 | 4 | 18 | 3 | 6 | 0 | 0 | 0 | 0 |
| H | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| I | 5 | 2 | 2 | 3 | 2 | 0 | 0 | 3 | 1 | 2 | 0 | 3 | 0 | 2 | 2 | 6 | 2 | 1 | 0 | 0 | 0 | 0 |
| K | 11 | 3 | 3 | 3 | 2 | 2 | 0 | 3 | 3 | 6 | 0 | 3 | 2 | 3 | 3 | 9 | 2 | 2 | 0 | 0 | 0 | 0 |
| L | 71 | 11 | 11 | 12 | 10 | 14 | 0 | 13 | 10 | 43 | 0 | 17 | 14 | 21 | 13 | 37 | 13 | 22 | 8 | 0 | 0 | 0 |
| M | 12 | 1 | 1 | 0 | 1 | 3 | 0 | 0 | 1 | 7 | 1 | 1 | 3 | 3 | 3 | 3 | 2 | 8 | 2 | 0 | 0 | 0 |
| N | 14 | 3 | 3 | 4 | 3 | 3 | 0 | 3 | 3 | 6 | 0 | 3 | 5 | 3 | 3 | 9 | 3 | 3 | 2 | 0 | 0 | 0 |
| P | 23 | 5 | 5 | 6 | 3 | 4 | 0 | 6 | 4 | 13 | 0 | 6 | 6 | 9 | 4 | 16 | 3 | 5 | 2 | 0 | 0 | 0 |
| Q | 29 | 6 | 6 | 7 | 6 | 6 | 0 | 6 | 6 | 19 | 0 | 7 | 6 | 13 | 8 | 19 | 7 | 12 | 4 | 0 | 0 | 0 |
| R | 33 | 5 | 5 | 4 | 5 | 8 | 0 | 5 | 4 | 19 | 0 | 6 | 8 | 9 | 9 | 16 | 6 | 11 | 4 | 0 | 0 | 0 |
| S | 27 | 5 | 5 | 9 | 6 | 3 | 0 | 8 | 5 | 16 | 0 | 10 | 5 | 12 | 7 | 26 | 5 | 5 | 2 | 0 | 0 | 0 |
| T | 21 | 4 | 4 | 4 | 2 | 6 | 0 | 4 | 4 | 11 | 0 | 5 | 6 | 7 | 5 | 13 | 5 | 4 | 4 | 0 | 0 | 0 |
| V | 93 | 10 | 10 | 7 | 9 | 21 | 0 | 12 | 11 | 51 | 0 | 16 | 22 | 26 | 17 | 37 | 16 | 42 | 14 | 0 | 0 | 0 |
| W | 20 | 4 | 4 | 4 | 2 | 6 | 0 | 4 | 4 | 10 | 0 | 4 | 4 | 6 | 4 | 12 | 2 | 4 | 3 | 0 | 0 | 0 |
| X | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Y | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Z | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

(a) SSM Matrix

| A | 16 |
|---|---|
| C | 2 |
| D | 2 |
| E | 2 |
| F | 2 |
| G | 3 |
| H | 0 |
| I | 2 |
| K | 2 |
| L | 9 |
| M | 1 |
| N | 3 |
| P | 3 |
| Q | 5 |
| R | 4 |
| S | 7 |
| T | 3 |
| V | 9 |
| W | 2 |
| X | 0 |
| Y | 0 |
| Z | 0 |

(b) Histogram

FIG. 99

|   | A | C | D | E | F | G | H | I | K | L | M | N | P | Q | R | S | T | V | W | X | Y | Z |
|---|---|---|---|---|---|---|---|---|---|---|---|---|---|---|---|---|---|---|---|---|---|---|
| A | 2 | 0 | 0 | 1 | 0 | 1 | 0 | 0 | 3 | 0 | 1 | 1 | 2 | 0 | 1 | 1 | 3 | 0 | 0 | 0 | 0 | 0 |
| C | 0 | 0 | 0 | 0 | 0 | 0 | 0 | 0 | 0 | 0 | 0 | 0 | 0 | 0 | 1 | 0 | 1 | 0 | 0 | 0 | 0 | 0 |
| D | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| E | 1 | 0 | 0 | 0 | 0 | 0 | 0 | 0 | 0 | 0 | 0 | 0 | 0 | 0 | 0 | 1 | 0 | 0 | 0 | 0 | 0 | 0 |
| F | 0 | 0 | 0 | 0 | 0 | 0 | 0 | 0 | 0 | 0 | 0 | 0 | 0 | 0 | 0 | 2 | 0 | 0 | 0 | 0 | 0 | 0 |
| G | 1 | 0 | 1 | 0 | 0 | 0 | 0 | 0 | 1 | 0 | 0 | 0 | 0 | 0 | 0 | 0 | 0 | 0 | 0 | 0 | 0 | 0 |
| H | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| I | 0 | 0 | 1 | 0 | 0 | 0 | 0 | 0 | 0 | 1 | 0 | 0 | 0 | 0 | 0 | 0 | 0 | 0 | 0 | 0 | 0 | 0 |
| K | 0 | 0 | 0 | 0 | 0 | 0 | 0 | 0 | 0 | 1 | 0 | 0 | 0 | 0 | 1 | 0 | 0 | 0 | 0 | 0 | 0 | 0 |
| L | 1 | 0 | 0 | 0 | 0 | 1 | 0 | 1 | 0 | 1 | 0 | 2 | 0 | 0 | 0 | 1 | 0 | 2 | 0 | 0 | 0 | 0 |
| M | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| N | 1 | 0 | 0 | 0 | 1 | 0 | 0 | 0 | 0 | 0 | 0 | 0 | 0 | 0 | 1 | 0 | 0 | 0 | 0 | 0 | 0 | 0 |
| P | 1 | 0 | 0 | 0 | 0 | 0 | 0 | 0 | 0 | 0 | 0 | 0 | 0 | 1 | 0 | 0 | 0 | 1 | 0 | 0 | 0 | 0 |
| Q | 2 | 0 | 0 | 0 | 0 | 0 | 0 | 1 | 1 | 0 | 0 | 0 | 0 | 0 | 0 | 0 | 1 | 0 | 0 | 0 | 0 | 0 |
| R | 3 | 0 | 0 | 0 | 1 | 0 | 0 | 0 | 0 | 0 | 0 | 0 | 0 | 0 | 0 | 0 | 0 | 0 | 0 | 0 | 0 | 0 |
| S | 1 | 0 | 0 | 1 | 0 | 0 | 0 | 1 | 0 | 0 | 0 | 0 | 1 | 0 | 2 | 0 | 0 | 0 | 0 | 0 | 0 | 0 |
| T | 0 | 0 | 0 | 0 | 0 | 0 | 0 | 0 | 0 | 0 | 0 | 0 | 1 | 0 | 0 | 2 | 0 | 0 | 0 | 0 | 0 | 0 |
| V | 3 | 0 | 0 | 0 | 0 | 0 | 0 | 0 | 0 | 2 | 0 | 0 | 0 | 1 | 1 | 1 | 0 | 1 | 0 | 0 | 0 | 0 |
| W | 0 | 0 | 0 | 0 | 0 | 1 | 0 | 0 | 0 | 0 | 0 | 0 | 0 | 0 | 0 | 0 | 0 | 0 | 1 | 0 | 0 | 0 |
| X | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Y | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Z | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Behavior | Audio | Proprioception | Combined |
|---|---|---|---|
| Lift | 29.0 (+11.6) | 95.2 (+30.4) | 95.2 (+28.8) |
| Shake | 57.2 (+30.0) | 88.4 (+73.2) | 92.0 (+62.6) |
| Drop | 86.2 (+9.8) | 93.6 (+48.0) | 97.8 (+17.0) |
| Crush | 72.8 (-0.6) | 88.2 (+3.6) | 92.0 (+3.4) |
| Push | 87.2 (+23.4) | 77.2 (+61.8) | 94.2 (+29.2) |
| Average | 66.32 (+14.72) | 88.52 (+43.42) | 94.24 (+28.24) |

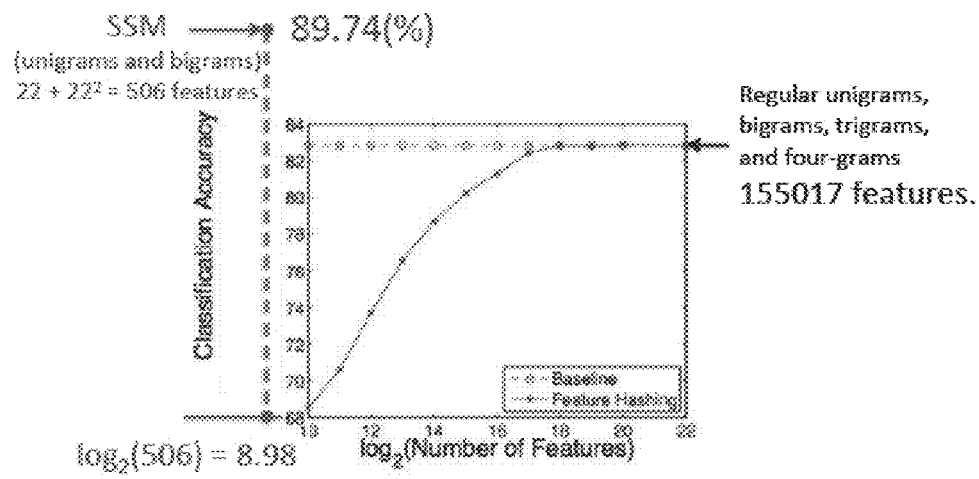
FIG. 101
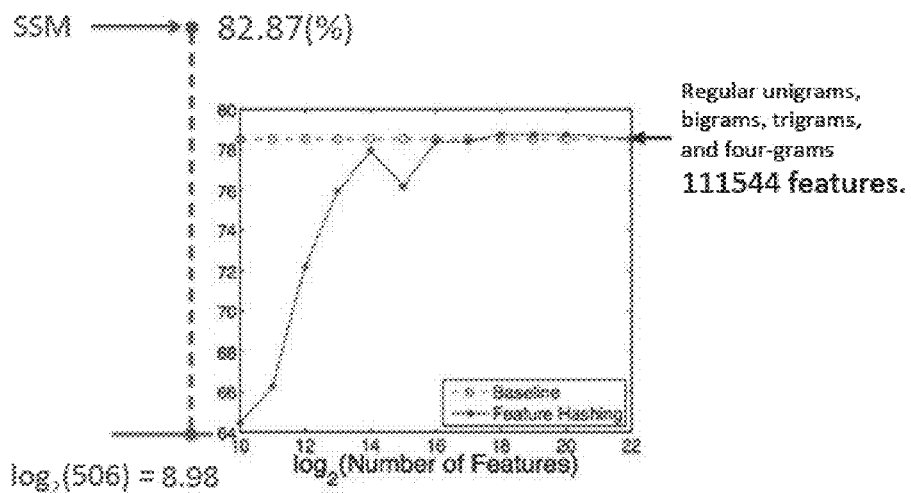
FIG. 102
|  | 1 Behavior | 2 Behaviors | 3 Behaviors | 4 Behaviors | 5 Behaviors |
|---|---|---|---|---|---|
| Audio | 66.32 (+14.72) | 86.64 (+14.44) | 94.62 (+11.32) | 97.64 (+8.48) | 98.4 (+6.00) |
| Proprioception | 88.52 (+43.40) | 96.56 (+30.44) | 98.18 (+18.38) | 98.56 (+10.88) | 98.60 (+5.60) |
| Combined | 94.24 (+28.20) | 98.56 (+13.43) | 99.20 (+5.98) | 99.52 (+2.64) | 99.60 (+1.40) |
FIG. 105

| Distributed Dual Matrix $D(S', S'')$ | Distributed and Replicated Histogram $h'$ | Distributed and Replicated Histogram $h''$ |
|---|---|---|
|     A  B<br>$\alpha$  [1][2]<br><br>$\beta$  [2][3]<br><br>$\gamma$  [1][1] |     <br>$\alpha$  [1][1]<br><br>$\beta$  [2][2]<br><br>$\gamma$  [1][1] |     A  B<br>[2][2]<br><br>[2][2]<br><br>[2][2] |

FIG. 113

| | Distributed Dual Matrix $D(S', S'')$ | Distributed and Replicated Histogram $h'$ | Distributed and Replicated Histogram $h''$ |
|---|---|---|---|
| Node 1: | A  B<br>$\alpha$  [1][2] | $\alpha$  [1][1] | A  B<br>[2][2] |
| Node 2: | A  B<br>$\beta$  [2][3] | $\beta$  [2][2] | A  B<br>[2][2] |
| Node 3: | A  B<br>$\gamma$  [1][1] | $\gamma$  [1][1] | A  B<br>[2][2] |

FIG. 114

| Iteration Number | Sequences | All Open Bigrams | Distributed and Replicated Histogram $h'$ | Distributed Dual Matrix $D(S', S'')$ |
|---|---|---|---|---|
| Initialization | | | $\alpha$ [0] [0]<br>$\beta$ [0] [0]<br>$\gamma$ [0] [0] |     A  B<br>$\alpha$ [0] [0]<br>$\beta$ [0] [0]<br>$\gamma$ [0] [0] |
| First | $S' = \beta$<br>$S'' = A$ | $\beta A$ | $\alpha$ [0] [0]<br>$\beta$ [1] [1]<br>$\gamma$ [0] [0] |     A  B<br>$\alpha$ [0] [0]<br>$\beta$ [1] [0]<br>$\gamma$ [0] [0] |
| Second | $S' = \beta\alpha$<br>$S'' = AB$ | $\beta A$   $\beta B$<br>      $\alpha B$ | $\alpha$ [1] [1]<br>$\beta$ [1] [1]<br>$\gamma$ [0] [0] |     A  B<br>$\alpha$ [0] [1]<br>$\beta$ [1] [1]<br>$\gamma$ [0] [0] |
| Third | $S' = \beta\alpha\gamma$<br>$S'' = ABA$ | $\beta A$   $\beta B$   $\beta A$<br>      $\alpha B$   $\alpha A$<br>            $\gamma A$ | $\alpha$ [1] [1]<br>$\beta$ [1] [1]<br>$\gamma$ [1] [1] |     A  B<br>$\alpha$ [1] [1]<br>$\beta$ [2] [1]<br>$\gamma$ [1] [0] |
| Fourth | $S' = \beta\alpha\gamma\blacksquare$<br>$S'' = ABA\blacksquare$ | $\beta A$   $\beta B$   $\beta A$   ▓<br>      $\alpha B$   $\alpha A$   ▓<br>            $\gamma A$   ▓ | $\alpha$ [1] [1]<br>$\beta$ [▓] [▓]<br>$\gamma$ [1] [1] |     A  B<br>$\alpha$ [1] [▓]<br>$\beta$ [2] [▓]<br>$\gamma$ [1] [▓] |

| Dual Matrix $D(S', S'')$ | Histogram Vector $h'$ | Histogram Vector $h''$ |
|---|---|---|
| $\begin{array}{c c c} & A & B \\ \alpha & 1 & 2 \\ \beta & 2 & 3 \\ \gamma & 1 & 1 \end{array}$ | $\begin{array}{c c} \alpha & 1 \\ \beta & 2 \\ \gamma & 1 \end{array}$ | $\begin{array}{c c} A & B \\ 1 & 3 \end{array}$ |

FIG. 119

| Distributed Dual Matrix $D(S', S'')$ | Distributed and Replicated Histogram $h'$ | Distributed and Replicated Histogram $h''$ |
|---|---|---|
| $\begin{array}{c c c} & A & B \\ \alpha & 1 & 2 \\ \beta & 2 & 3 \\ \gamma & 1 & 1 \end{array}$ | $\begin{array}{c c c} & A & B \\ \alpha & 1 & 1 \\ \beta & 2 & 2 \\ \gamma & 1 & 1 \end{array}$ | $\begin{array}{c c} A & B \\ 1 & 3 \\ 1 & 3 \\ 1 & 3 \end{array}$ |

FIG. 120

| Dual Matrix $D(S''',S'''')$ | Histogram Vector $h'''$ | Histogram Vector $h''''$ |
|---|---|---|
|    X  Y  Z<br>α  [0][2][1]<br>γ  [1][3][1]<br>δ  [0][1][1] | α [1]<br>γ [2]<br>δ [1] | X  Y  Z<br>[1][2][1] |

FIG. 122

| Distributed Dual Matrix $D(S''',S'''')$ | Distributed and Replicated Histogram $h'''$ | Distributed and Replicated Histogram $h''''$ |
|---|---|---|
|    X  Y  Z<br>α [0][2][1]<br>γ [1][3][1]<br>δ [0][1][1] | α [1][1][1]<br>γ [2][2][2]<br>δ [1][1][1] | X  Y  Z<br>[1][2][1]<br>[1][2][1]<br>[1][2][1] |

SYSTEMS AND METHODS FOR RECOGNIZING, CLASSIFYING, RECALLING AND ANALYZING INFORMATION UTILIZING SSM SEQUENCE MODELS

CROSS-REFERENCE TO RELATED PATENT APPLICATIONS

This patent application is a continuation of PCT/US2014/025094, filed Mar. 12, 2014, which claims the benefit of U.S. Provisional Patent Application No. 61/777,032, filed Mar. 12, 2013, the teachings and disclosure of which are hereby incorporated in their entireties by reference thereto.

FIELD OF THE INVENTION

This invention generally relates to recognizing, classifying, and analyzing information, and more particularly, to systems and methods for recognizing, classifying, and analyzing information using SSM sequence models via sequence encoding, recognition, and recall.

BACKGROUND OF THE INVENTION

As asked in the title of a paper in *Trends in Cognitive Sciences*, "Does the huamn mnid raed wrods as a wlohe?" Many people find it easy to read words even if their letters are shuffled. Some do not even notice anything wrong with the words. Indeed, as discussed by S. Dehaene in *Reading in the Brain*, "these abstract similarity effects are so powerful that we experience little difficulty in raednig etnrie sneetnecs in wihch the ltteers of eervy wrod hvae been miexd up, ecxpet for the frsit and the lsat ltteers."

These effects are not just mere curiosities. They tell of something fundamental about how the human brain works. For example, they tell that the representation used by the brain is invariant to transpositions of letters when it comes to reading tasks. There is probably a good reason why such a representation would be useful, namely, it will be invariant to noise, reshuffling, and even dropping of certain letters in words. If one could find a representation with similar properties, then it is quite plausible that it would work for other sensory modalities as well.

Currently, Hidden Markov Models, or HMMs, are the predominant method for performing recognition tasks, e.g. speech recognition. They are also used in Computational Bioinformatics to do gene prediction in large genomic databases. They have been used successfully for human activity recognition, including American Sign Language recognition, recognizing defensive an offensive maneuvers in football plays with potential military applications when players are mapped to friendly and enemy forces.

It was hoped that by divulging the hidden Markov model approach in all its details in a clear and precise manner, the speech research community at large would adopt what would become known as the "invincible approach" to the automatic recognition of speech. Unfortunately, despite promising work aimed at merging statistical and linguistic knowledge and at generalizing the concept of hidden Markov models to develop still more powerful models, it has been noted that there have not been any alternative that outperforms the HMM approach.

The present application provides one such representation that has much broader applications than HMMs, indeed that can be applied to almost any task that has to deal with sequences, representing sequences, encoding sequences, reproducing sequences, and matching potentially noisy sequences, and that can be applied to a variety of practical tasks in various embodiments of the present invention. These and other advantages of the invention, as well as additional inventive features, will be apparent from the description of the invention provided herein.

BRIEF SUMMARY OF THE INVENTION

Embodiments of the present the invention provide biologically-inspired models for sequence representation. The models are capable of capturing the statistical nature of sequences and can be used for sequence encoding, recognition, and recall. The models can be trained in real time, which makes them a direct competitor to HMMs. They also have fewer tunable parameters than HMMs. They are highly parallelizable, which ensures that they can scale up to very large problems; HMMs rely on dynamic programming techniques, which limits their ability to benefit from parallelization.

Indeed, HMMs require a large number of parameters to be completely specified, including (1) the number of distinct states in the model, N; (2) the number of distinct observation symbols, i.e., the discrete alphabet size, M; (3) a matrix A of size N×N that specifies the transition probabilities between the states; (4) a matrix B of size N×M that stores the probability of observing each symbol in each state; and (5) a vector π of size N that specifies the initial state distribution. In other words, in order to specify an HMM, one needs $1+1+N^2+NM+N$ parameters. In a conservative example with N=4 and M=5 this corresponds to 42 parameters.

In contrast, an SSM Sequence Model constructed in accordance with embodiments of the present invention is completely specified with the following parameter: the number of distinct observation symbols, i.e., the discrete alphabet size, M. In other words, an SSM in accordance with embodiments of the present invention is completely specified with only one parameter. This parameter corresponds to the size of the alphabet that was used to construct the observation sequences that the model is required to match.

Unlike embodiments of the present invention that utilize the SSM Sequence Model, HMMs have three basic problems that must be solved for HMMs to be useful. First, given an observation sequence O, and a model λ, how does one efficiently compute $P(O|\lambda)$, the probability of the observation sequence, given the model? Second, given an observation sequence O, and a model λ, how does one choose a corresponding state sequence Q, which is optimal in some meaningful sense (i.e., best "explains" the observations)? Third, How does one adjust the model parameters λ=(A, B, π) to maximize $P(O|\lambda)$?

In plain English, the meaning of the three problems is the following. Problem 1 must be solved when HMMs are used for recognition. It boils down to calculating the probability that a given sequence of symbols was produced by a given HMM (called the model). Typically one HMM is trained for each sequence that one wants to recognize. For example, one HMM can be trained for each word in the English dictionary. Given a new word/sequence the recognition system calculates the probability with which the word could have been produced by each HMM. The test word is then matched/recognized as the word associated with the most likely HMM.

Problem 2 attempts to estimate the most likely state sequence (the order in which the states of the HMM are visited as the sequence is consumed). In other words, it tries to calculate the most likely path through the states of the HMM for the given observation sequence. The solution is only "optimal" in a probabilistic sense. Problem 2 is typically solved with the Viterbi algorithm.

Problem 3 deals with the training of the HMM. Solving it requires an iterative tuning of the parameters (i.e., the transition matrix A and the observation matrix B, a total of N×N plus N×M parameters). The Baum-Welch algorithm is typically used to solve this problem.

However, these three problems are solved much more simply with embodiments of the SSMs of the present invention. With regard to Problem 1, with SSMs, the recognition problem boils down to calculating the symmetrized KL divergence between two SSM matrices. Somewhat interestingly, with SSMs it is possible to compare any two trained models and not just the novel sequence and the model. This is not possible with HMMs. With regard to Problem 2, this problem is specific only to HMMs. SSMs do not have states so they do not have to estimate the most likely state sequence. With regard to Problem 3, training an SSM model is trivial. Essentially, training is equivalent to constructing the SSM matrix by counting the number of open bigrams in the sequence. That is it. There is no need to iteratively train the model and wait for it to converge.

The Table 1 below lists the algorithmic complexity for the two models for each of the three problems. All three HMM algorithms run in $O(TN^2)$ time, where T is the length of the sequence and N is the number of states in the HMM. Because the complexity depends on the length of the sequence these algorithms are not suited for long sequences. Training an HMM can take a long time as the convergence of the Baum-Welch algorithm can be excruciatingly slow. The algorithm requires multiple iterations and may get stuck in local minima. This is the reason why HMMs are typically trained off-line.

TABLE 1

| TASK | HMM Complexity | SSM Complexity |
|---|---|---|
| Problem 1: Recognition | $O(TN^2)$ | $O(M^2)$ |
| Problem 2: Most Likely State Sequence | $O(TN^2)$ | N/A |
| Problem 3: Training | Iterations × $O(TN^2)$ | $O(TM)$ |

An embodiment of an SSM, on the other hand, can be trained in $O(TM)$ time in a single pass through the training sequence. The result is always the same and there are no issues with convergence or local minima. SSMs don't have states like HMMs so the problem of estimating the most likely state sequence is not relevant for them. The SSM representation (i.e., the SSM matrix) does not depend on the length of the sequence. It depends only on the size of the alphabet, M. Recognition can be performed in $O(M^2)$ time by comparing two SSM matrices. Thus, SSMs are clearly faster than HMMs.

Further, all SSM algorithms can be parallelized quite easily. In other words, they can be implemented to run simultaneously on multiple computers, or multiple CPUs, or multiple CPUs with multiple cores, which would speed them up even further. The HMM algorithms, on the other hand, rely on dynamic programming techniques in which the current state of the computation depends on multiple partial results that were calculated in the previous time step(s). Because of the extensive sharing of partial results that is required by dynamic programming, it is not easy, or even feasible, to parallelize the HMM algorithms.

Embodiments of the present invention using the SSM matrices have numerous applications including, but not limited to methods utilizing SSMs in place of HMMs in applications in which HMMs are currently used or are usable, methods utilizing SSMs and/or open n-grams in place of regular bigrams, trigrams, or n-grams in applications in which such are currently used or are usable, methods of encoding an SSM representation that uses open bigrams, open trigrams, or open n-grams, methods of encoding with multiple channels of information (dual, tri-band, n-band) where the channels could originate from different modalities, methods of using the encoded representation for classification, recognition, and ranking tasks with off-the-shelf machine learning algorithms, methods of speech recognition and auditory pattern recognition, methods of speech synthesis and speech production using artificial vocal tracts, e.g., robotic speech, methods of recognizing, classifying, and analyzing biological sequences, e.g., protein sequences, DNA sequences, etc., methods of recognizing, classifying, and analyzing text, e.g., classifying news articles into topics, methods of similarity/distance/rank calculation for sequences/documents/etc., methods of improving the search performance of multimedia search engines, methods of improving the search performance of Internet search engines, methods of automated spellchecking, e.g., improved handling of letter and/or word transpositions errors, methods of computing the SSM representation for a long sequence from the matrices for its subsequences (concatenation theorem), methods of extracting the sequence from the encoded SSM representation, methods of extracting sequence(s) from dual SSMs, e.g., unrolling one sequence given the other sequence that was used to build the dual representation, methods of encoding, unrolling, and recognizing designed for parallel architectures, e.g., GPUs, methods of SSM distance metric calculations for parallel architectures, e.g., GPU, methods of incremental matching, e.g., match as the sequence is read instead of calculating distances between matrices after the encoding is done, methods of encoding, matching, and unrolling using exponential SSMs that use exponentially decaying coupling functions or any other coupling functions that can be used to characterize the relationships between the elements of the sequences, methods of encoding probabilistic sequences using SSMs (e.g., each element has an associated probability measure), methods of inferring the missing values in SSM matrices using the constraints and relationships imposed by the SSM representation, e.g., inferring the diagonal elements of a single SSM matrix from the remaining values, methods of using an SSM representation in which the matrix elements and the histogram elements can be replicated and/or distributed across multiple functional units, e.g., the elements of each row of the matrix can be processed by a separate unit and/or individual units can be shared by multiple SSMs, methods of inferring missing values in a distributed SSM representation, e.g., inferring the values of missing histogram and matrix elements, methods of predicting a subsequent segment of a sequence given a previous segment, methods of predicting subsequent segments of multiple sequences unfolding in parallel given some previous segments of these sequences, methods of multiplexing and demultiplexing multiple channels of information using SSM cascades, methods of implementing an analog of a Turing machine using SSM cascades, methods of implementing an analog of digital logic elements using SSM cascades, e.g., AND, NOT, OR.

Embodiments of the present invention also have applications of SSMs in Robotics, e.g., interactive object recognition, that couple the actions and the perceptions of the robot, e.g., using SSM representations and SSM cascades that couple video, audio, and proprioceptive data, that organize the sensorimotor experiences of the robot, e.g., associative and autoassociative memory that is built using SSMs and SSM cascades, for detecting and using the affordances of objects by a robot, etc.

Embodiments of the present invention also may perform methods of using SSMs and SSM cascades for building an associative and autoassociative memory, e.g., building, maintaining and querying a hierarchical associative and autoassociative memory. Embodiments also have application in computer vision, e.g., image recognition, face recognition, recognition of partially occluded objects, activity recognition, predicting future activities. Other embodiments have applications of SSMs for processing, searching, indexing, and retrieval of multimedia streams of information, applications of SSMs for approximate pattern matching in multimedia streams of information. A further embodiment provides an SSM implementation on a chip, e.g., hardware implementation of encoding, unrolling, and matching algorithms.

An embodiment of a system of the present invention includes an input device for receiving an input sequence, a processor coupled to the input device, the processor converting the input sequence to an input sequence SSM Matrix, and a memory device configured to store the known SSM Matrices representing known sequences. Preferably, the processor compares the input sequence SSM Matrix to the known SSM Matrices in order to match the input sequence to the known sequence.

In one embodiment configured for spell checking, the input device is one of a keyboard, touchscreen text entry device, text file, etc. The input sequence is a misspelled word, and the known SSM Matrices representing the known sequences are derived from correctly spelled words. In such an embodiment the processor suggests one of the correctly spelled words to replace the misspelled word either in an output text file or on a display screen for the user.

In an embodiment configured for voice recognition, the input device is a microphone or audio file, and the system also includes a signal analyzer coupled to the input device to convert an input audio signal into input Mel Frequency Cepstrum Coefficients. An analog to digital converter is coupled to the signal analyzer to discretize each of the input Mel Frequency Cepstrum Coefficients to form an input Mel Frequency Cepstrum Coefficient sequence. The processor encodes each input Mel Frequency Cepstrum Coefficient sequence into an input Mel Frequency Cepstrum Coefficient SSM Matrix. Stored in the memory are the known sequence SSM Matrices formed by known Mel Frequency Cepstrum Coefficient SSM Matrices for known words. In this embodiment, the processor outputs a known word corresponding to the input audio signal in a text file transcription, on a screen, etc.

In an embodiment configured for speech synthesis, the system also includes an output speaker, and the input device is one of a keyboard, touchscreen text entry device, or text file such that the input sequence is a textual word The known SSM Matrices representing known sequences are derived from audio files of spoken words. In this embodiment, the processor drives the speaker with one of the audio files of the spoken words corresponding to the textual word of the input.

In an embodiment configured for computer vision, the input device is one of a visual scanner or visual image file. The processor extracts visual features from an image of an object scanned by the scanner or contained in the image file and assigns sequence elements to each visual feature to form the input sequence. The SSM Matrices representing known sequences are derived from visual files of scanned images of known objects. In this embodiment the processor identifies the object that was scanned or contained in the image file as one of the known objects.

In one embodiment the processor and the memory are configured on a single chip. In another embodiment the processor comprises a number of parallel processors. In yet another embodiment the processor is a GPU.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 1 is a mapping illustrating the generation of all open bigrams for a sample sequence "READ;"

FIG. 4 illustrates an embodiment of a 26×26 SSM matrix utilizing all letters of the relevant alphabet for the sample sequence "STORAGE;"

FIG. 5 illustrates an embodiment of an SSM matrix utilizing only relevant letters from the relevant alphabet for the sample sequence "STORAGE;"

FIG. 6 is tabular flow diagram illustrating the encoding of the sample sequence "ACBBA" into an embodiment of an SSM matrix of the present invention;

FIG. 7 is a mapping illustrating the open bigrams and SSM matrices for three sample sequences corresponding to three English language words;

FIG. 8 is a mapping illustrating the open bigrams and an SSM matrix for a sample sequence corresponding to a misspelled English language word;

FIG. 9 is tabular flow diagram illustrating sequence recognition and selection of a correct sequence based on matching to a closest familiar sequence in accordance with an embodiment of the present invention;

FIG. 10 is a mapping illustration showing two sample sequences that do not share identical characters, and construction of an SSM matrix that allows comparison of the sequences in accordance with an embodiment of the present invention;

FIG. 11 is a mapping flow diagram illustrating smoothing of the open bigram probabilities in order to compute the symmetric distance measure between two sequences in accordance with an embodiment of the present invention;

FIG. 12 is a tabular illustration of the values of the smoothed probabilities for all open bigrams for each of the two sequences illustrated in FIG. 11;

FIG. 13 is a tabular flow diagram illustrating the calculation of the distance measure between the two sequences of FIG. 11 in accordance with an embodiment of the present invention;

FIG. 14 is a tabular flow diagram illustrating the calculation of the distance measure between the sequences of FIGS. 7 and 8 utilizing smoothed probabilities in accordance with an embodiment of the present invention;

FIG. 15 is an illustration of a 3×3 SSM matrix for a sample sequence;

FIG. 16 is an illustration of the SSM matrix of FIG. 15, including its row and column sums;

FIG. 17 is an illustration of the SSM matrix of a sample sequence, including its row and column sums;

FIG. 18 is a tabular flow diagram illustrating an effect of insertion of a character at the end of a sequence on the open bigrams and on an SSM matrix in accordance with an embodiment of the present invention;

FIG. 19 is a tabular flow diagram illustrating an effect of deletion of a character at the end of a sequence on the open bigrams and on an SSM matrix in accordance with an embodiment of the present invention;

FIG. 22 is a tabular flow diagram illustrating a method of unrolling an entire encoded sequence from an SSM matrix in accordance with an embodiment of the present invention;

FIG. 23 is a tabular flow diagram illustrating a method of unrolling in reverse an entire encoded sequence from an SSM matrix in accordance with an embodiment of the present invention;

FIG. 24 is a tabular illustration of two discrete sequences that unfold in parallel over time encoded into a dual SSM matrix in accordance with an embodiment of the present invention;

FIG. 25 is a tabular illustration of the two discrete sequences that unfold in parallel over time of FIG. 24, but taken in the reverse order, encoded into a dual SSM matrix in accordance with an embodiment of the present invention;

FIG. 26 is a tabular illustration of the four sets of open bigrams formed from two sequences S' and S" in accordance with an embodiment of the present invention;

FIG. 27 is a tabular illustration of the four SSM matrices formed from the two sequences S' and S" of FIG. 26 in accordance with an embodiment of the present invention;

FIG. 28 is a tabular illustration of the four sets of open bigrams formed from two sequences in accordance with an embodiment of the present invention;

FIG. 29 is a tabular illustration of the four SSM matrices formed from the two sequences of FIG. 28 in accordance with an embodiment of the present invention;

FIG. 30 is a tabular illustration of the nine SSM matrices formed from three sequences in accordance with an embodiment of the present invention;

FIG. 31 is a model notation of a single SSM model illustrating the decoding of the sequence S from a single SSM matrix and histogram for the encoded sequence in accordance with an embodiment of the present invention;

FIG. 32 is a model notation illustrating the decoding of the two sequences S' and S" separately in accordance with an embodiment of the present invention;

FIG. 33 is a model notation illustrating the decoding of the two sequences S' and S" at the same time in parallel in accordance with an embodiment of the present invention;

FIG. 34 is a model notation illustrating the decoding of the sequence S" when the sequence S' is provided at run time in accordance with an embodiment of the present invention;

FIG. 35 is a model notation illustrating the decoding of the sequence S' when the sequence S" is provided at run time in accordance with an embodiment of the present invention;

FIG. 36 is a tabular flow diagram illustrating the encoding of two sequences into a dual SSM matrix in accordance with an embodiment of the present invention;

FIG. 37 is a tabular illustration of the dual SSM matrix D(S', S"), the histogram vector h', and the histogram vector h' produced by the encoding illustrated in FIG. 36 in accordance with an embodiment of the present invention;

FIG. 38 is a tabular flow diagram illustrating the encoding of two sequences into a dual SSM matrix in accordance with an embodiment of the present invention;

FIG. 39 is a tabular illustration of the dual SSM matrix D(S', S"), the histogram vector h', and the histogram vector h' produced by the encoding illustrated in FIG. 38 in accordance with an embodiment of the present invention;

FIG. 40 is a tabular illustration showing the minimal dual model for the two sequences of FIG. 36 that can be unrolled for the sequence S' if the sequence S" is provided at run time in accordance with an embodiment of the present invention;

FIG. 41 is a tabular illustration showing the minimal dual model for the two sequences of FIG. 38 that can be unrolled for the sequence S' provided the sequence S" is provided at run time in accordance with an embodiment of the present invention;

FIG. 42 is a tabular flow diagram illustrating the decoding of the sequence S' of FIG. 36 using the minimal dual model of FIG. 40 in accordance with an embodiment of the present invention;

FIG. 43 is a diagrammatic view of a dual unrolling problem for the sequence S' of FIG. 36 wherein the dual SSM matrix D(S', S"), the histogram vector h", and the sequence S" are provided and the sequence S' is to be decoded in accordance with an embodiment of the present invention;

FIG. 44 is a tabular flow diagram illustrating the decoding of the sequence S' of FIG. 38 using the minimal dual model of FIG. 41 in accordance with an embodiment of the present invention;

FIG. 45 is a diagrammatic view of a dual unrolling problem for the sequence S' of FIG. 38 wherein the dual SSM matrix D(S', S"), the histogram vector h", and the sequence S" are provided and the sequence S' is to be decoded in accordance with an embodiment of the present invention;

FIG. 46 is a diagrammatic view of a dual unrolling problem for the sequence S' wherein the dual SSM matrix D(S', S"), the histogram vector h", and the sequence S" are provided and the sequence S' is to be decoded in accordance with an embodiment of the present invention;

FIG. 47 is a tabular flow diagram illustrating a dual unrolling in reverse example for the sequence $(S'')^R$ wherein the reverse of the first sequence $(S')^R$ is provided in accordance with an embodiment of the present invention;

FIG. 48 is a processing flow diagram illustrating that a sequence S can be split into two sequences $S_A$, $S_B$, which are then used to encode a dual SSM Matrix $D(S_B, S_A)$ in accordance with an embodiment of the present invention;

FIG. 49 is a model notation illustrating the prediction of $S_B$ given $S_A$ using the sequence segments illustrated in FIG. 48;

FIG. 50 illustrates that multiple sequences can each be split into fragments for the generation of dual SSM matrices to enable complex cascades to be constructed in accordance with an embodiment of the present invention;

FIG. 51 is model notation illustrating an unrolling cascade in accordance with an embodiment of the present invention;

FIG. 52 illustrates two sequences sampled at different rates in accordance with an embodiment of the present invention;

FIG. 53 is tabular illustration of the open bigrams formed from the two sequences of FIG. 52 depending on the sampling and rescaling rules in accordance with an embodiment of the present invention;

FIG. 54 is a tabular illustration of the open trigrams formed from a single sequence in accordance with an embodiment of the present invention versus the regular trigrams for the same sequence;

FIG. 57 is a tabular flow diagram illustrating calculation of the open trigram counters for an exemplary sequence in accordance with an embodiment of the present invention;

FIG. 58 is a tabular illustration of the open bigrams of two symmetric sequences that encode to the same SSM matrix;

FIG. 59 is a tabular illustration of the open trigrams and SSM representations of the two symmetric sequences of FIG. 58;

FIG. 60 is a tabular illustration of the tri-band SSM representation for three exemplary sequences in accordance with an embodiment of the present invention;

FIG. 61 is a tabular illustration of the tri-band SSM representation for three exemplary sequences in accordance with an embodiment of the present invention;

FIG. 62 is a tabular flow diagram illustrating an exponential SSM encoding of an exemplary sequence in accordance with an embodiment of the present invention;

FIG. 63 is a tabular illustration of the linear SSM matrices and exponential matrices for the two symmetric sequences of FIG. 58 in accordance with an embodiment of the present invention;

FIG. 64 is a tabular flow diagram illustrating the encoding of a sequence using exponential decay in accordance with an embodiment of the present invention;

FIG. 65 is a tabular flow diagram illustrating the decoding of a sequence in reverse from the SSM matrix of FIG. 62 encoded using exponential decay in accordance with an embodiment of the present invention;

FIG. 66 is a tabular illustration of an attempted forward unrolling of an SSM matrix encoded using exponential decay using the encoding histogram vector h;

FIG. 67 is a tabular flow diagram illustrating the forward unrolling of an SSM matrix encoded using exponential decay using the encoding histogram vector h* in accordance with an embodiment of the present invention;

FIG. 68 is a tabular flow diagram illustrating the forward unrolling of an SSM matrix encoded using exponential decay using the encoding histogram vector h* in accordance with an embodiment of the present invention;

FIG. 69 is a is a tabular illustration of an attempted forward unrolling of an SSM matrix encoded using exponential decay using the encoding histogram vector h;

FIG. 70 is a tabular flow diagram illustrating the unrolling of an SSM matrix in reverse encoded using exponential decay using the encoding histogram vector h in accordance with an embodiment of the present invention;

FIG. 71 is a tabular flow diagram illustrating the dual encoding of an SSM matrix exponential decay in accordance with an embodiment of the present invention;

FIG. 72 is a tabular flow diagram illustrating the forward unrolling of a dual exponential SSM matrix in accordance with an embodiment of the present invention;

FIG. 73 is a schematic flow diagram illustrating the conversion of a discrete sequence into a spike-based representation in accordance with an embodiment of the present invention;

FIG. 75 is a graphical illustration of spike-based sequences for demonstrating dual SSM encoding with exponential decay in accordance with an embodiment of the present invention;

FIG. 87 is a graphical illustration of computed distance measurements between two utterances of the same word spoken by different speakers in accordance with an embodiment of the present invention;

FIG. 88 is a tabular illustration of computed distance measurements between an utterance of a word spoken by a speakers compared to the closest words in a database of words spoken by different speakers to illustrate matching in accordance with an embodiment of the present invention;

FIG. 93 is a tabular illustration of word recognition through distance measurements in accordance with an embodiment of the present invention;

FIG. 94 is a tabular illustration of the open bigrams and SSM matrix for the DNA sequence GATTACA in accordance with an embodiment of the present invention;

FIG. 95 illustrates an amino acid sequence of a protein in FASTA format along with its name and class that was encoded in an SSM matrix in accordance with an embodiment of the present invention;

FIG. 96 is a mapping key from letter codes to amino acids used in the FASTA format for representing nucleotide and protein sequences in plain text;

FIG. 97 is a schematic illustration of an existing pipeline for subcellular protein localization;

FIG. 98 is a schematic illustration of an SSM pipeline for subcellular protein localization in accordance with an embodiment of the present invention;

FIG. 99 is tabular illustration of a SSM representation for the example protein shown in FIG. 95 in accordance with an embodiment of the present invention;

FIG. 101 is a graphical illustration of the results of the pipeline of FIG. 97 compared to the SSM pipeline of FIG. 98 for a non-plant dataset of protein sequences;

FIG. 102 is a graphical illustration of the results of the pipeline of FIG. 97 compared to the SSM pipeline of FIG. 98 for a plant dataset of protein sequences;

FIG. 105 is a tabular illustration of the performance of the learning pipeline for interactive object recognition of FIG. 103, measured in percentage of correctly recognized objects for combinations of multiple different behaviors;

FIG. 113 is a graphical illustration of a distributed dual SSM matrix produced by the distributed dual encoding algorithm for the sequences are $S'=\beta\alpha\gamma\beta$ and $S''=ABAB$ in accordance with an embodiment of the present invention;

FIG. 114 is a graphical illustration of a distributed dual SSM matrix produced by the distributed dual encoding algorithm for the sequences are $S'=\beta\alpha\gamma\beta$ and $S''=ABAB$ having the rows of the dual matrix $D(S', S'')$ distributed across three different computational nodes in accordance with an embodiment of the present invention;

FIG. 115 is a graphical flow diagram illustrating distributed dual encoding in accordance with an embodiment of the present invention;

FIG. 116 is a graphical flow diagram illustrating distributed dual unrolling in accordance with an embodiment of the present invention;

FIG. 118 is a graphical flow diagram illustrating distributed dual unrolling with exponential decay in accordance with an embodiment of the present invention;

FIG. 119 is a graphical illustration of a regular dual SSM matrix produced by the dual encoding algorithm for the sequences are $S'=\beta\alpha\gamma\beta$ and $S''=BBBA$ in accordance with an embodiment of the present invention;

FIG. 120 is a graphical illustration of a distributed dual SSM matrix produced by the distributed dual encoding algorithm for the sequences are $S'=\beta\alpha\gamma\beta$ and $S''=BBBA$ in accordance with an embodiment of the present invention;

FIG. 121 is a graphical illustration of a distributed dual SSM matrix produced by the distributed dual encoding algorithm for the sequences are $S'=\beta\alpha\gamma\beta$ and $S''=BBBA$ having the rows of the dual matrix $D(S', S'')$ distributed across three different computational nodes in accordance with an embodiment of the present invention;

FIG. 122 is a graphical illustration of a regular dual SSM matrix produced by the dual encoding algorithm for the sequences are $S'''=\gamma\alpha\delta\gamma$ and $S''''=XYZY$ in accordance with an embodiment of the present invention;

FIG. 123 is a graphical illustration of a distributed dual SSM matrix produced by the distributed dual encoding algorithm for the sequences are $S'''=\gamma\alpha\delta\gamma$ and $S''''=XYZY$ in accordance with an embodiment of the present invention;

Figure 124:
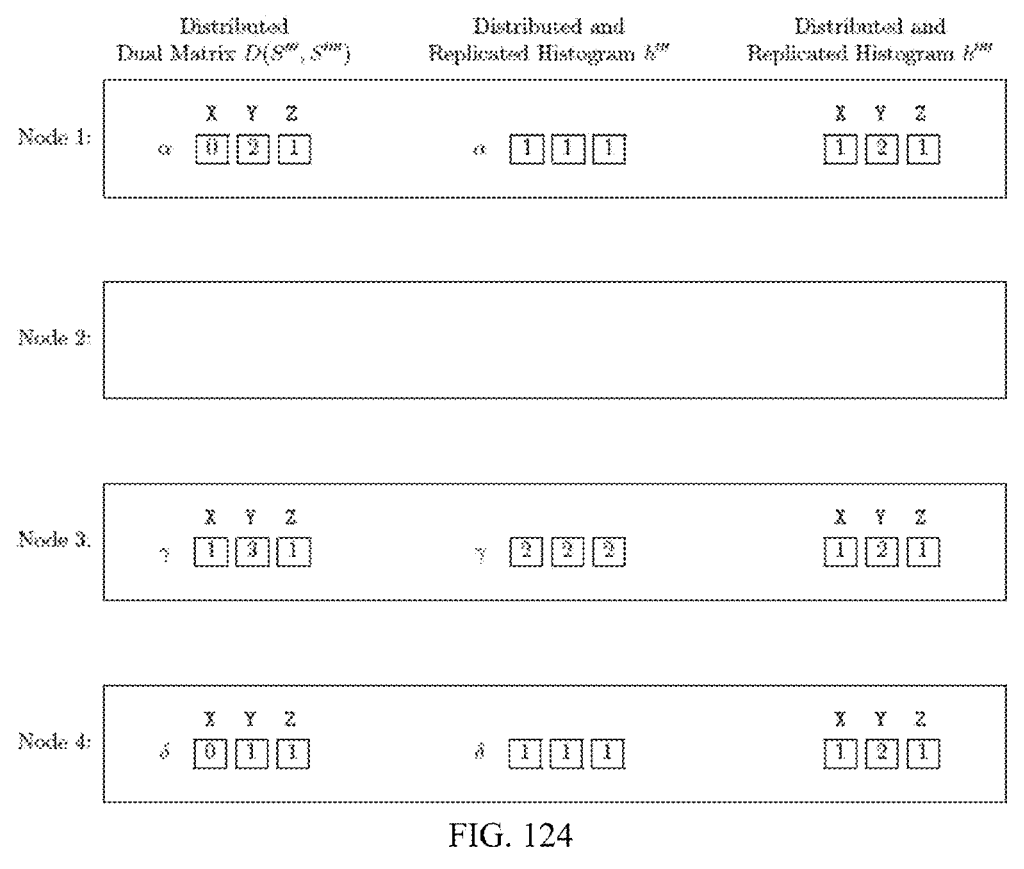
Figure 125:
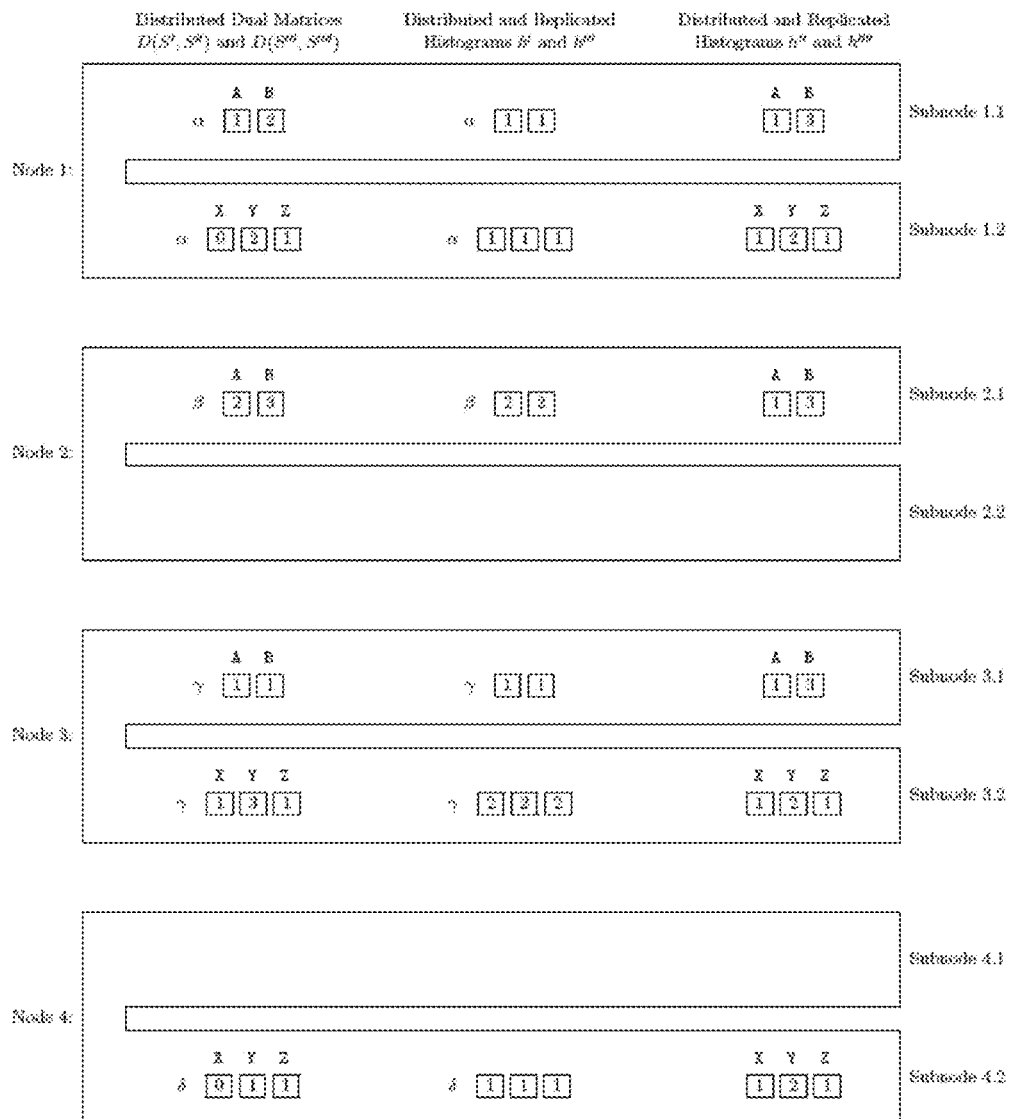

FIG. 124 is a graphical illustration of a distributed dual SSM matrix produced by the distributed dual encoding algorithm for the sequences are S'''=γαδγ and S''''=XYZY having the rows of the dual matrix D(S''', S'''') distributed across four different computational nodes in accordance with an embodiment of the present invention; ad FIG. 125 is a graphical illustration of a distributed dual SSM matrix produced by the distributed dual encoding algorithm for the sequences are S'''=γαδγ and S''''=XYZY having the rows of the dual matrix D(S''', S'''') distributed across four different computational nodes with subnodes in accordance with an embodiment of the present invention.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

The following describes biologically-inspired systems and models for sequence representation and various embodiments for the implementation thereof. However, as will be recognized by those skilled in the art from the foregoing and following description, the applications for such models are vast, and therefore the descriptions of the various embodiments contained herein should be taken by way of example and not by way of limitation. Indeed, in those applications wherein other models are used to perform the analysis, e.g. in systems where HMMs are utilized, the various elements of the system are not described in detail as they are readily apparent from such existing systems. Instead, the details of the calculations utilizing the SSM matrices will consume the majority of the description. However, this is not to say that such systems do not include such hardware, e.g. input devices such as keyboards, touch screens, microphones, image capture devices, etc., or front end devices that process the input and prepare it for analysis, e.g. digitizers, discretizers, signal or spectrum analyzers, etc., or output devices, e.g. computer displays, speakers, robotic motor drivers, etc.

As will be made clear from the following, the model captures the statistical nature of sequences and can be used for sequence encoding, recognition, and recall. Embodiments of the model can be trained in real time, which makes them direct competitors to HMMs. Embodiments of the present invention also have fewer tunable parameters than HMMs. Preferred embodiments are parallelizable, preferably highly parallelizable, which ensures that they can scale up to very large problems; HMMs rely on dynamic programming techniques, which limits their ability to benefit from parallelization. Embodiments of the present invention are biologically plausible and can explain several psychological phenomena.

It is instructive to review the building and definition of a discrete sequence with which embodiments of the present invention will work. A discrete sequence $S=S_1 S_2 S_3 \ldots S_T$ of length T is constructed using characters $S_i$ drawn from a finite alphabet $\Gamma = \{c_1, c_2, \ldots, c_M\}$ of size M. Without loss of generality, it can be assumed that the alphabet characters can be uniquely mapped to the set of integers from 1 to M. This mapping can be accomplished easily with the help of a lookup table. The ASCII table is one such example. It is noted that, as used herein, the sequence can be as small as a single character, i.e. M=1.

Given a discrete sequence, e.g., the word READ, all pairs of characters that occur one after another can easily be identified as follows: RE, EA, and AD. These are called bigrams. All triples of characters that occur together in the sequence can also be identified as follows: REA and EAD. These are called trigrams. This concept generalizes quite naturally to n-grams. N-gram models have been used extensively by others to capture the statistical properties of sequences, e.g., sequences of words, syllables, or characters. In one embodiment of the system and method of the present invention, bigrams, trigrams, or n-grams are not used. Instead, open bigrams are used as will be discussed below.

Open bigrams are also pairs of characters, but the two characters no longer have to occur immediately one after another in the sequence. For example, the word READ has the following six open bigrams: RE, RA, RD, EA, ED, and AD. In other words, the left and the right character in the open bigram may be separated by either one or more characters. The only restriction is that the left character must occur temporally before the right one as the sequence is scanned from left to right.

Open bigrams have been used to model the ability of humans to read words with transposed letters. For reasons that will become clear later, this model is extended for embodiments of the present invention by allowing characters to form open bigrams with themselves. In this case the left and the right character in the open bigram are one and the same and the temporal separation between them in the sequence is zero. For the word READ this adds the following four open bigrams to the list: RR, EE, AA, and DD. This representation is illustrated in FIG. 1, which shows that each letter of the word READ is "mapped" to each letter of the word READ to form the 10 open bigrams used in embodiments of the present invention. The orientation of the open bigrams, i.e. right justified, provides helpful properties that will be discussed more fully below.

Given two words, say READ and RAED, their similarity can be estimated based on the number of open bigrams that they have in common. As can be seen from the Table 2 below, these two words share 90% of their open bigrams. Transposing the two middle letters affects only 1 of the 10 open bigrams: EA, which is unique to READ, and AE, which is unique to RAED.

TABLE 2

| Sequence | All Open Bigrams | | | | | | | | | |
| --- | --- | --- | --- | --- | --- | --- | --- | --- | --- | --- |
| READ | RR | RE | RA | RD | EE | EA | ED | AA | AD | DD |
| RAED | RR | RA | RE | RD | AA | AE | AD | EE | ED | DD |

Figures 2, 3:
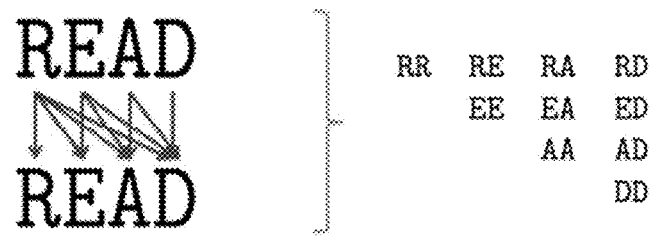
FIG. 2 is a further mapping of the sequence of FIG. 1, further illustrating the generation of an SSM matrix in accordance with an embodiment of the present invention.
FIG. 3 is a mapping of a different sequence from that of FIG. 1, also illustrating the generation of an SSM matrix in accordance with an embodiment of the present invention.

Given a sequence it is beneficial to have a representation that can rapidly tell how many open bigrams of a certain type occur in the sequence. For short sequences, one way to do this is to store the open bigrams in a list as it was shown in the previous example. As the sequence length increases, however, searching through this list is no longer computationally efficient. There is a more natural representation that organizes the open bigrams into a matrix. This representation will be referred to herein as the SSM Open Bigram Matrix, or SSM Matrix for short. The rows of the matrix represent the left letters in the open bigrams. The columns represent the right letters. FIG. 2 shows all open bigrams and the resulting SSM matrix for the word READ. A more complex example for the word SCIENCE in which the letters C and E repeat twice is illustrated in FIG. 3.

Each element of the SSM matrix can be interpreted as an integer counter that reflects the number of open bigrams of a given type that are present in the sequence for which the matrix was constructed. For example, SC occurs twice in SCIENCE, which is why there is a 2 in the fifth row and the first column of the matrix shown in FIG. 3 (i.e., the row corresponding to S and the column corresponding to C). The diagonal elements of the matrix represent the number of open bigrams that a character forms with itself. For example, there are two C's in SCIENCE, but there are three open bigrams of type CC as reflected by the 3 in the upper left corner of the matrix. To see why this is the case, the first character will be noted as $C_1$ and the second one as $C_2$. The three open bigrams that they form between themselves are: $C_1C_1$, $C_1C_2$, and $C_2C_2$. The properties of the diagonal elements and the matrix as a whole will be discussed later.

Previous approaches that have used open bigrams have not organized them in a matrix. Also, they have not considered counting the number of instances of each open bigram as their counters have always been binary: a bigram is either present in the sequence or not. Even if it occurs twice it is still counted only once. One exception in which a matrix is constructed, the counter values are overwritten when the matrix is added together with other unrelated matrices. As will be described shortly, in one embodiment, keeping the counts allows the matrix to be treated as a probability distribution over the set of open bigrams. This allows classic statistical techniques to be performed on the matrices and also to compare two sequences given their matrices.

When working with SSM matrices it is often desired to store them to an external device or to load them into the computer's memory. It is worth mentioning at this point that in one embodiment the system of the present invention only stores the smallest possible footprint for any SSM matrix, as that representation can be rather sparse. The examples shown in FIGS. 4 and 5 show two possible ways to encode the word STORAGE. The first one shown in FIG. 4 uses all 26 letters in the English alphabet and requires a 26×26 matrix. The second one shown in FIG. 5 stores only the relevant letters for this sequence and the resulting 7×7 matrix, which is much smaller.

In this example even the smaller matrix of FIG. 5 is sparse as almost half of its entries are zeroes. This sparsity can be exploited even further. For example, the matrix can be represented with a hash table where the key is the open bigram itself and the value is the counter. If a counter is 0, then its corresponding open bigram is not stored in the hash table.

In one computer implemented embodiment, an elegant algorithm for encoding a discrete sequence into an SSM matrix runs in O(TM) time, where T is the length of the sequence and M is the size of the alphabet. The algorithm traverses the sequence from left to right. At each iteration the system reads one character and updates a histogram vector, h, that counts how many times each of the M possible characters has been observed up to the current position in the sequence. The contents of the entire histogram vector are then added to the column of the SSM matrix that corresponds to the last read character. This process is repeated until there are no more characters left. The algorithm returns the SSM matrix, X, after the last iteration.

A property of the algorithm is that it does not require access to the entire sequence. In other words, the whole sequence does not have to be loaded into memory before the encoding can start. In fact, no part of the sequence needs to be stored in memory except for the current character. This makes it suitable for time-critical applications as the matrix can be constructed while the sequence is unfolding in real time.

The algorithm completes in T iterations and at every iteration it updates only M entries of the matrix (a single column). Thus, its complexity is O(TM). If the length of the sequence is not known in advance, then the algorithm can be modified in another embodiment to keep reading one character at a time until no more characters are available or until a terminating character is reached. The run time would remain the same in this case.

To demonstrate how this embodiment of the system of the present invention operates, assume that the sequence ACBBA is to be encoded into an SSM matrix. This sequence has three unique characters, so it may be assumed that the alphabet size is also 3, i.e., M=3. The algorithm will finish in five iterations because the length of the sequence is 5, i.e., T=5. The partial results for each of these five iterations are shown in FIG. 6.

The algorithm maintains two internal data structures: a character histogram vector of size M and an SSM matrix of size M×M. At the beginning, both of these are initialized with zeros. The system scans the sequence from left to right, one character at a time. After each new character is read its corresponding bin counter in the histogram is incremented by one. For example, when the first letter A is read the first element of the vector is incremented. The newly updated frequency vector is then added to the column of the SSM matrix that corresponds to the character that was just read (A in this case). This completes the first iteration. This process is repeated for every character in the sequence.

The last row of FIG. 6 shows the operations performed during the fifth iteration, but in this case the components that are added or modified are highlighted. Note that, at this iteration, there are five new open bigrams that have to be counted, but only 3 elements are updated in the SSM matrix. In other words, only M matrix elements are updated at each iteration. It is this property that gives the nice O(TM) run time of the system of this embodiment. By adding the character frequency vector to the corresponding column of the matrix the algorithm implicitly counts all new open bigrams without having to perform the extra additions. The frequency vector does the bookkeeping that makes this possible.

For example, in the fifth iteration shown in FIG. 6, the vector reveals that there are 2 A's, 2 B's, and 1 C in the first five characters of the sequence that have been read so far. Because the fifth character is an A, it can be inferred that A will be the right letter in all five new open bigrams, i.e., they will be of the form *A. From the frequency vector the left letters can be inferred as well, i.e. there will be two open bigrams of type AA, two of type BA, and one of type CA. Updating their counts in the SSM matrix can be accomplished by simply adding the frequency vector to the first column of the matrix (i.e., the column corresponding to the letter A, which is the right letter in all five open bigrams that must be added at that iteration).

The system has a nice extension for off-line processing of very long sequences in a further embodiment of the present invention, e.g., large training data sets that are stored on an external device. In such an embodiment, each sequence is split into multiple contiguous chunks and each chunk is sent to a separate processor (or core) for encoding. The partial results are then assembled to create the final SSM matrix. This embodiment scales linearly with the number of processors P. It runs in $O(TM^2/P)$ time, which means it will be faster than the prior embodiment if P>M (i.e., if the number of processors is greater than the number of letters in the alphabet).

Figures 7, 8, 9:
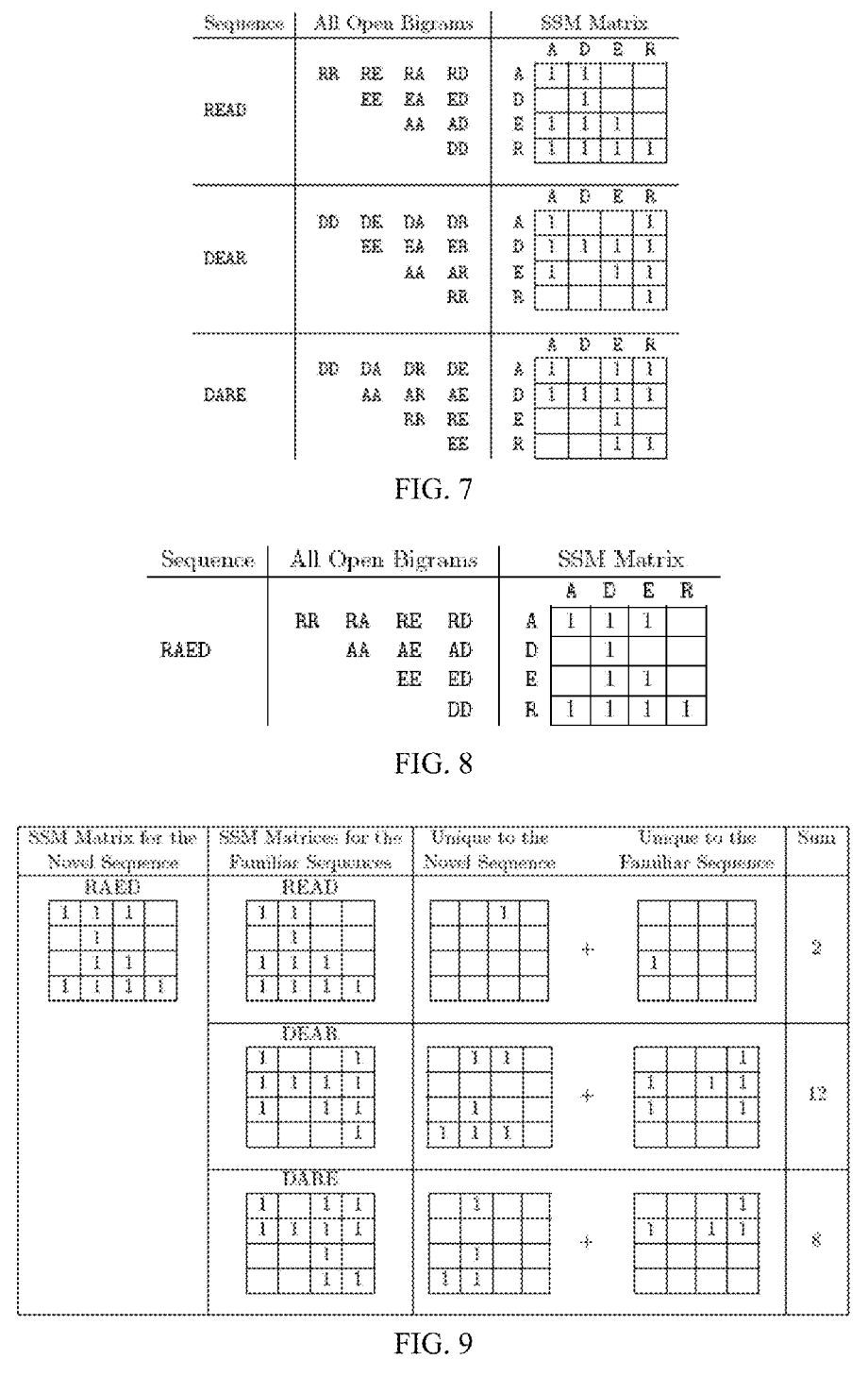

In one embodiment to be described below, the SSMs are used in a system and method of sequence recognition. FIG. 7 shows the SSM matrices for three words: READ, DEAR, and DARE. Without loss of generality, it may be assumed that these are the only words on which the recognition system has been trained. Training consists of simply calculating one matrix for each word, something that can be done really fast by counting the number of open bigrams in a single pass through the sequence as described hereinabove. For the sake of clarity and visibility the zero entries in these matrices are not shown.

FIG. 8 shows the SSM matrix for the word RAED. This word does not exist in the English dictionary, but as discussed in the BACKGROUND OF THE INVENTION section above, humans have no problems matching RAED to READ. As will be discussed below, the SSM Sequence Model also finds that READ is the closest match.

In this embodiment the system and method of the present invention matches the new sequence to the closest familiar sequence. Finding the best match begins by comparing the SSM matrix of the novel word with the matrix of the first familiar word as shown in FIG. 9. The comparison includes two steps. First, for each matrix element that has a value of one in the new matrix, find if the corresponding element in the familiar matrix is zero. If it is zero, then make the corresponding entry in a temporary matrix equal to one. Essentially, this set of operations finds which 1's are unique to the novel matrix and do not occur in the familiar matrix. Second, perform the reverse operation: for every element that has a value of one in the matrix for the familiar sequence, find if the corresponding matrix location for the novel sequence is zero. If it is zero, then make the corresponding element in a second temporary matrix equal to one. This process finds which 1's are unique to the familiar matrix and do not occur in the novel matrix. Finally, count the number of ones in the two temporary matrices. This results in a distance score. This procedure is then repeated for all other matrices in the training set. The novel word is then matched to one of the familiar words that has the lowest distance score. In this example, RAED will be recognized as READ. The distance score for the other two words is significantly higher as shown in FIG. 9.

This example is just an approximation to the actual algorithm that is used for recognition in other embodiments of the present invention. There are two implementation details that must be handled properly for this to work, but the overall process is very similar. First, the matrices for the two sequences must have the same number of rows and columns and they must correspond to the same alphabet characters. If this condition is not met, then empty rows and columns must be added to align the alphabets of the two matrices. The alignment process is described more fully hereinbelow. Second, the comparison between the two matrices must be meaningful in some probabilistic sense. The matching operation described in the embodiment above is an approximation to calculating the symmetrized Kullback-Leibler (KL) divergence. The KL divergence is a commonly used metric in statistics and information theory that measures the difference between two probability distributions. The metric uses the log function and thus it cannot handle zero matrix entries. This problem can be avoided by smoothing the matrix elements, which is discussed more fully hereinbelow along with additional examples.

As mentioned before, an SSM matrix is typically stored (and visualized) in its minimum form. In other words, if the alphabet size is M, but a sequence uses only K of the alphabet letters (K<M), then it makes sense to store the K×K matrix instead of the much larger M×M matrix. When two different matrices have to be compared, however, this may lead to problems if their corresponding sequences use different subsets of characters. In this case, the two matrices need to be brought into alignment before they can be compared. This may require inserting empty rows and columns in one or both of the matrices. Also, up to now it was tacitly assumed that the rows and the columns of an SSM matrix are always sorted in alphabetical order. If for whatever reason this is not the case, then the rows and the columns of one of the matrices must be swapped until they are sorted in the same way as those of the other matrix.

The example illustrated in FIG. 10 shows how to align the matrices for the words CAT and HAT. Notice in FIG. 10 that they appear to have the same SSM matrix in the 3×3 format, but the matrices are different in the 4×4 format. In other words, to properly compare the two, such comparison must be done in the smallest possible matrix that covers the union of the letters in the two words. In this case, the union set consists of the following four letters: A, C, H, and T. To align the two matrices a row and a column of zeroes that correspond to the letter H must be inserted in the first matrix. Similarly, an empty row and an empty column for the letter C must be inserted in the second matrix. Only now would it make sense to compare the two matrices.

If computational speed is an issue, then there is a nice shortcut that can be exploited to perform the alignment. The idea is to align the two sequence representations at the open bigram level instead of at the matrix level. This is possible because the distance metric is insensitive to open bigrams that do not occur in the two sequences (i.e., zero entries that occur in the same positions in the two SSM matrices). Notice that in the CAT and HAT example shown in FIG. 10 there are six open bigrams in the first word and six in the second one. Three of them, however, appear in both words: AA, AT, and TT. Thus, the union of the two sets of open bigrams has only 9 elements instead of 12. Furthermore, both of these numbers are smaller than 16, which is the number of elements stored in the SSM matrix. This shortcut, however, would begin to make more sense after the smoothing operation is defined below.

Given two sequences, the distance between them is to be estimated. Because discrete sequences can be viewed as strings, metrics designed for string matching, such as the Levenshtein edit distance, can be used. Other sequence alignment techniques, such as dynamic time warping, can be used. The time required to compute these metrics, however, depends on the lengths of the sequences and this is something that is desired to be avoided here for the sake of speed. Thus, it would be nice if the distance can be estimated from the corresponding SSM matrices, assuming that the sequences share the same alphabet.

In Mathematics, two matrices are often compared using a matrix norm of their difference. There are many possible matrix norms that can be used. For example, the max-norm, induced norms such as the two-norm, Frobenius norm, and many others. Each of these matrix norms can be used to define a distance between two SSM matrices. More formally, given two sequences $S_1$ and $S_2$ and their SSM matrices $X_1$ and $X_2$, the distance between the two sequences computed using an arbitrary matrix norm ∥•∥ of the difference between $X_1$ and $X_2$ can be defined as follows:

$$d_{\|\cdot\|}(S_1, S_2) = \|X_1 - X_2\|. \quad (1)$$

Another way to compare two sequences using their SSM matrices is to extract the probability distribution of the open bigrams from the matrix of each sequence and then to compare the resulting distributions. This method, which will be used in all examples, is described below. However, it is noted that other distance metrics can be used with the SSM matrices, including, but not limited to an asymmetric D-KL distance, Euclidean distance, both of which run in $O(M^2)$ operations.

In the following discussion, the distance measure is based on the KL divergence. Let S be a discrete sequence of length T and let X be its SSM matrix. The sequence is composed of characters drawn from a finite alphabet $\Gamma = \{c_1, \ldots, c_M\}$ of size M. Because each matrix element $X_{ij}$ represents the number of times the open bigram $c_i c_j$ occurs in the sequence, it is possible to use the matrix to quantify how likely an open bigram is with respect to all other open bigrams in the same sequence. In other words, the SSM matrix can be used to compute the probability distribution of the open bigrams in the sequence. More specifically, the probability p ($c_i c_j$|S) of the open bigram $c_i c_j$ in the sequence S can be computed using the following formula:

$$p(c_i c_j | S) = \frac{X_{ij}}{\sum_{k=1}^{M} \sum_{l=1}^{M} X_M}. \quad (2)$$

If the sequence contains repeated characters, then some open bigrams will occur multiple times, which will increase their probability. On the other hand, open bigrams that do not occur in the sequence will have a probability of zero. Using the formula (2) above the probabilities for all open bigrams in S can be calculated and arranged in an M×M matrix P, such that $P_{ij} = p(c_i c_j | S)$.

Given two sequences $S_1$ and $S_2$ and their corresponding SSM matrices X and Y, it is desired to be able to compare the sequences based on the probabilities of their open bigrams. The Kullback-Leibler divergence (or KL-divergence) is a well-known measure of the difference between two probability distributions. In particular, the KL-divergence can be used to quantify the difference between two probability distributions of open bigrams. More formally, if P and Q are two probability distributions such that $P_{ij}$ is the probability of the open bigram $c_i c_j$ in $S_1$ and $Q_{ij}$ is the probability of $c_i c_j$ in $S_2$, then the KL-divergence $D_{KL}(P\|Q)$ is defined using the following formula:

$$D_{KL}(P\|Q) = \sum_{i=1}^{M} \sum_{j=1}^{M} P_{ij} \log \frac{P_{ij}}{Q_{ij}}. \quad (3)$$

Both P and Q must sum up to 1 for the KL-divergence to be properly defined. If $P_{ij} = 0$ and $Q_{ij} > 0$, then the term 0 log 0 is assumed to be zero. If both $P_{ij}$ and $Q_{ij}$ are zero for some i and j, then the corresponding term 0 log 0/0 in the formula is also assumed to be zero. The KL-divergence is infinite if $Q_{ij} = 0$ and $P_{ij} > 0$ for some i and j.

If an open bigram is absent from both sequences, then its corresponding term in this formula is zero. However, if an open bigram is present in one sequence but absent from the other, then the term corresponding to this bigram can be infinite. Thus, before the KL-divergence can be used for sequence matching, it is necessary to smooth the probabilities of the open bigrams. In other words, the probabilities stored in the matrices P and Q need to be adjusted and come up with two new matrices ^P and ^Q such that none of the terms in this formula are infinite.

There are several smoothing techniques that can be used to prevent the possibility of getting an infinite KL-divergence. One technique that is easy to explain and implement is called additive smoothing. It will be used in all examples described below, but the overall approach is not tied to any specific smoothing method. Using additive smoothing, the smoothed probability $\hat{P}_{ij}$ of the open bigram $c_i c_j$ in the sequence $S_1$ can be computed with the following formula:

$$\hat{P}_{ij} = \hat{p}(c_i c_j | S_1) = \frac{X_{ij} + \alpha}{\sum_{k=1}^{M} \sum_{l=1}^{M} X_{kl} + \alpha U}, \quad (4)$$

where α is a parameter that controls the intensity of the smoothing and U is the number of unique open bigrams that occur in at least one of the two sequences. In other words, if $B_1$ is the set of open bigrams in $S_1$ and $B_2$ is the set of open bigrams in $S_2$, then $U = |B_1 \cup B_2|$. Typically, the parameter α is set to 1.

Similarly, the smoothed probability $\hat{Q}_{ij}$ of the open bigram $c_i c_j$ in the sequence $S_2$ is given by:

$$\hat{Q}_{ij} = \hat{p}(c_i c_j | S_2) = \frac{Y_{ij} + \alpha}{\sum_{k=1}^{M} \sum_{l=1}^{M} Y_{kl} + \alpha U}. \quad (5)$$

Smoothing is performed only for the open bigrams that do occur in at least one of the two sequences, i.e., $c_i c_j \in B_1 \cup B_2$. Thus, the two formulas immediately above are not used for open bigrams that do not appear in either of the two sequences, which means that the probabilities of these missing bigrams will remain zero. Including the missing open bigrams in the smoothing calculations will result in oversmoothing.

Now a distance measure $d_{KL}(S_1, S_2)$ between two sequences $S_1$ and $S_2$ can be defined. The measure, which uses the KL-divergence between the smoothed probability distributions ^P and ^Q extracted from the two SSM matrices X and Y, is defined using the following formula:

$$d_{KL}(S_1, S_2) = D_{KL}(\hat{P} \| \hat{Q}) = \quad (6)$$
$$\sum_{i=1}^{M} \sum_{j=1}^{M} \hat{P}_{ij} \log \frac{\hat{P}_{ij}}{\hat{Q}_{ij}} \sum_{i=1}^{M} \sum_{j=1}^{M} \hat{p}(c_i c_j | S_1) \log \frac{\hat{p}(c_i c_j | S_1)}{\hat{p}(c_i c_j | S_2)}.$$

Because the Kullback-Leibler divergence $D_{KL}(\hat{P}\|\hat{Q})$ is not symmetric, the distance measure $d_{KL}(S_1, S_2)$ is also not symmetric, i.e., $d_{KL}(S_i, S_2) \neq d_{KL}(S_2, S_1)$. However, it is possible to formulate a symmetric distance measure by adding two asymmetric distance measures. More formally, the symmetric distance measure between two sequences $S_1$ and $S_2$ is defined as:

$$d_{KL}^{(symm)}(S_1, S_2) = d_{KL}(S_1, S_2) + d_{KL}(S_2, S_1). \quad (7)$$

As an example with smoothing and the symmetric distance measure just discussed, a very common typing mistake, i.e. typing TEH instead of THE, is used. The following example uses these two words to illustrate how to smooth the open bigram probabilities in order to compute the symmetric distance measure $d_{KL}^{(symm)}$ between two sequences.

Using the same notation as above, let $S_1$=THE and $S_2$=TEH. Also, let $B_1$ and $B_2$ be two sets that contain the open bigrams that occur in each sequence. Furthermore, let X and Y be the SSM matrices for the two sequences. The values of these variables are shown in FIG. 11. This FIG. 11 also shows the two matrices P and Q that represent the unsmoothed open bigram probabilities for each sequence, obtained by dividing the entries of each SSM matrix by the number of open bigrams that occur in the corresponding sequence. The last column of FIG. 11 shows the smoothed open bigram probability distributions ^P and ^Q, calculated using the additive smoothing method described above.

Both sequences have six open bigrams, i.e., $|B_1|=|B_2|=6$. It is easy to notice, however, that the words THE and TEH have five open bigrams in common: TT, TH, TE, HH, and EE. There are only two open bigrams that appear in one word but do not appear in the other word: HE and EH. Thus, the number of all unique open bigrams, U, that appear in at least one of the two sequences is 5+2=7, i.e., $U=|B_1 \cup B_2|=7$.

In FIG. 11, the open bigrams HE and EH have been highlighted to emphasize that they occur in only one of the two sequences. Notice that their corresponding entries in the SSM matrix for the other sequence are zeros (also highlighted). These entries remain zeros in the unsmoothed probability matrices P and Q, which is the reason why the unsmoothed probabilities cannot be used to compute a distance measure based on KL-divergence. The open bigram probabilities, however, have been adjusted in the smoothed probability matrices ^P and ^Q as described below.

Once the size of $|B_1 \cup B_2|$ is known, additive smoothing can be applied to smooth the probabilities. Using the default value of 1 for the smoothing intensity parameter α, the smoothed probabilities for each of the seven open bigrams that appear in the sequences can be computed as follows:

$$\hat{p}(c_i c_j | THE) = \frac{X_{ij} + \alpha}{\sum_{k=1}^{M} \sum_{l=1}^{M} X_{kl} + \alpha \cdot |B_1 \cup B_2|} = \frac{X_{ij} + 1}{13}, \quad (8)$$

$$c_i c_j \in B_1 \cup B_2 = \{TT, TH, TE, HH, EE, HE, EH\}.$$

$$\hat{p}(c_i c_j | TEH) = \frac{Y_{ij} + \alpha}{\sum_{k=1}^{M} \sum_{l=1}^{M} Y_{kl} + \alpha \cdot |B_1 \cup B_2|} = \frac{Y_{ij} + 1}{13}, \quad (9)$$

$$c_i c_j \in B_1 \cup B_2 = \{TT, TH, TE, HH, EE, HE, EH\}.$$

Given the three alphabet characters in this example (E, H, and T), there are nine possible open bigrams. As already illustrated, seven of them appear in either THE or TEH, or in both. The open bigrams ET and HT, however, do not appear in either of the two sequences. Therefore, their probabilities are not smoothed. In other words, ^p(ET|THE)=^p(HT|THE)=0 and also ^p(ET|TEH)=^p(HT|TEH)=0. This means that their corresponding terms in the KL-divergence formula will also be zero.

FIG. 12 shows the values of the smoothed probabilities for all open bigrams for each of the two sequences. Because these are probabilities they must sum up to 1, which is indeed the case as shown in the bottom row of FIG. 12.

Finally, the distance between the two sequences is ready to be calculated. This is done in two steps as shown in FIG. 13. First, the asymmetric distance measure $d_{KL}(S_1, S_2)$ is calculated between the first and the second sequence. Second, the distance in the opposite direction, i.e., between $S_2$ and $S_1$ using $d_{KL}(S_2, S_1)$ is calculated. The results of these operations are shown as two matrices in FIG. 13. Summing over all elements of these two matrices, the symmetric distance between THE and TEH is found to equal to 2/13.

Figure 14:
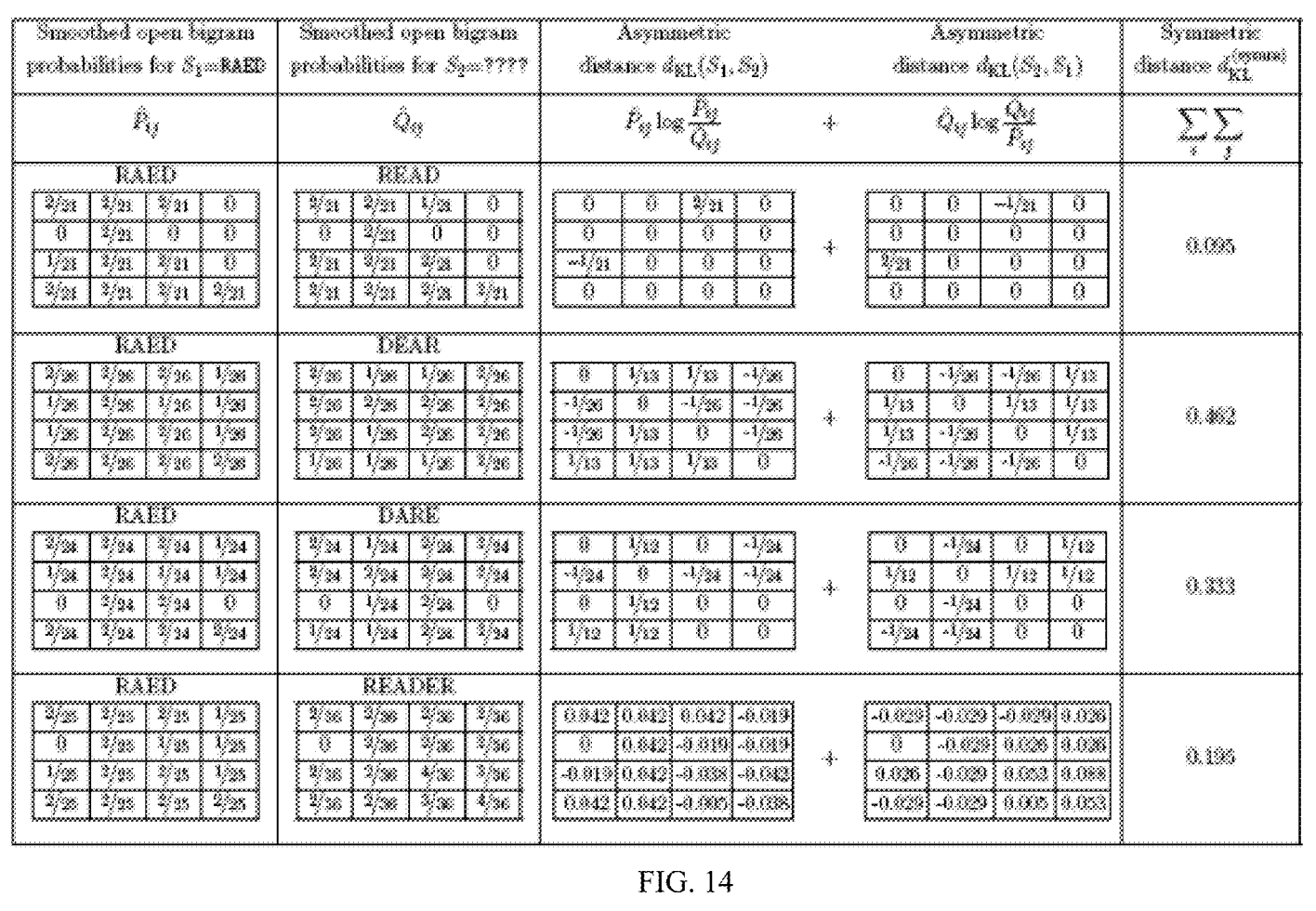

Previously, an example with the words: RAED, READ, DEAR, and DARE was discussed (see FIG. 9). The first was the test word and the other three were the training words. At that time, however, only an intuitive description of the steps required to calculate the distance between two sequences was given. FIG. 14 revisits this example, but this time utilizes a system and method of the present invention that uses smoothing and KL-divergence.

The SSM matrices for the sequences (not shown here, but see the original example) are first interpreted as probability distributions over the set of open bigrams. These probabilities are then smoothed before the distance measure between two sequences is computed. One thing that is worth pointing out is that smoothing is only defined relative to a pair of sequences. This explains why the denominators in the smoothed matrices ^P and ^Q are different for every row. In other words, the open bigram probabilities for the test sequence RAED must be smoothed separately with the open bigrams probabilities for each of training sequences.

As before, the novel word is matched with the familiar word that has the lowest distance measure. In this case, RAED is still recognized as READ. To illustrate one subtlety of the smoothing procedure, in this example, the word READER is added, which is composed of the same four letters as the other words, but has a length of six. Because this word is longer than the test word, the smoothing denominator in the ^Q matrix is larger than the one in the ^P matrix in the last row. The reason for this is that the smoothing equations take into account the total number of open bigrams in each sequence and longer sequences naturally have more open bigrams. Despite the two extra characters, the sequence READER is ranked second after READ in terms of its distance to the test word RAED. In other embodiments, the system and method check if at the end of the search the minimum distance is greater than some threshold, in which case it will indicate that the testing sequence is unknown. Second, it may be extended to find the best 3 (or best k) sequences and pick the most common label among them. Finally, it is worth mentioning that this calculation can be parallelized quite easily as the set of matrices for the familiar sequences can be split into multiple chunks and the each of the chunks can be searched in parallel.

There is a more direct formula for computing the symmetric distance measure that does not require division. This formula can be derived from the previous formulas by performing some straightforward algebraic transformations as shown below:

$$d_{KL}^{(symm)}(S_1, S_2) = d_{KL}(S_1, S_2) + d_{KL}(S_2, S_1) \quad (10)$$

$$= \sum_{i=1}^{M} \sum_{j=1}^{M} \hat{P}_{ij} \log \frac{\hat{P}_{ij}}{\hat{Q}_{ij}} + \sum_{i=1}^{M} \sum_{j=1}^{M} \hat{Q}_{ij} \log \frac{\hat{Q}_{ij}}{\hat{P}_{ij}}$$

$$= \sum_{i=1}^{M} \sum_{j=1}^{M} \hat{P}_{ij} (\log \hat{P}_{ij} - \log \hat{Q}_{ij}) +$$

-continued $$\sum_{i=1}^{M}\sum_{j=1}^{M}\hat{Q}_{ij}(\log\hat{Q}_{ij}-\log\hat{P}_{ij})$$

$$=\sum_{i=1}^{M}\sum_{j=1}^{M}(\hat{P}_{ij}\log\hat{P}_{ij}-\hat{P}_{ij}\log\hat{Q}_{ij}+$$

$$\hat{Q}_{ij}\log\hat{Q}_{ij}-\hat{Q}_{ij}\log\hat{P}_{ij})$$

$$=\sum_{i=1}^{M}\sum_{j=1}^{M}((\hat{P}_{ij}-\hat{Q}_{ij})\log\hat{P}_{ij}-(\hat{P}_{ij}-\hat{Q}_{ij})\log\hat{Q}_{ij})$$

$$=\sum_{i=1}^{M}\sum_{j=1}^{M}(\hat{P}_{ij}-\hat{Q}_{ij})\cdot(\log\hat{P}_{ij}-\log\hat{Q}_{ij})$$

$$=\sum_{i=1}^{M}\sum_{j=1}^{M}(\hat{p}(c_ic_j|S_1)-\hat{p}(c_ic_j|S_2))\cdot$$

$$(\log\hat{p}(c_ic_j|S_1)-\log\hat{p}(c_ic_j|S_2)).$$

This algorithm described below uses this formula, so it might be helpful to give an example using the same two words as in one of the previous examples: THE and TEH. Using this new formula, the symmetric distance measure between these two sequences can be computed as follows:

$$d_{KL}^{(symm)}(THE, TEH) = \tag{11}$$

$$\sum_{c_ic_j \in \{TT,TH,TE,EE,EH,HE,HH\}} (\hat{p}(c_ic_j|THE) - \hat{p}(c_ic_j|TEH)) \cdot$$

$$(\log\hat{p}(c_ic_j|THE) - \log\hat{p}(c_ic_j|TEH)).$$

As explained before, the summation is performed only for the terms that correspond to the open bigrams that appear in at least one of the two words. In this example, however, the smoothed probabilities $\hat{p}(c_ic_j|THE)$ and $\hat{p}(c_ic_j|TEH)$ are equal for each open bigram $c_ic_j$ that is present in both words, i.e., for $c_ic_j \in \{TT, TE, TH, EE, HH\}$. Because of that, the terms corresponding to these five open bigrams are zero. In other words, the summation can be performed only for the terms that correspond to the two open bigrams HE and EH, which are present in one of the words but not in both. Thus, the symmetric distance between these two sequences is:

$$d_{KL}^{(symm)}(THE, TEH) = (\hat{p}(HE|THE) - \hat{p}(HE|TEH)) \cdot \tag{12}$$

$$(\log_2\hat{p}(HE|THE) - \log_2\hat{p}(HE|TEH)) +$$

$$(\hat{p}(EH|THE) - \hat{p}(EH|TEH)) \cdot$$

$$(\log_2\hat{p}(EH|THE) - \log_2\hat{p}(EH|TEH))$$

$$=\left(\frac{2}{13}-\frac{1}{13}\right)\cdot\left(\log_2\frac{2}{13}-\log_2\frac{1}{13}\right)+$$

$$\left(\frac{1}{13}-\frac{2}{13}\right)\cdot\left(\log_2\frac{1}{13}-\log_2\frac{2}{13}\right)$$

$$=\frac{1}{13}\cdot\log_2\frac{2}{1}-\frac{1}{13}\cdot\log_2\frac{1}{2}$$

$$=\frac{1}{13}\cdot(1)-\frac{1}{13}\cdot(-1)$$

$$=\frac{2}{13}.$$

Perhaps the most mysterious property of the SSM matrix is that it can be used to reconstruct the sequence that was used to construct the matrix. In other words, given only the SSM matrix, it is possible to unroll the original sequence, one character at a time. Furthermore, the sequence can be reconstructed both from start to end, and also from end to start. The following describes several methods for performing these operations in accordance with various embodiments of the present invention.

To describe the unrolling methods, one simple example will be used hereinbelow. FIG. 15 shows the SSM matrix for an unknown sequence. While the original sequence is unknown, there are several things that can be learned about this sequence from its matrix. First, the total number of open bigrams that are present in the sequence can be calculated by summing up all $X_{ij}$ elements of the matrix. In this case, the sum is 6, which corresponds to a sequence of length 3. The sequence length, T, can be calculated by solving the quadratic equation $T(T+1)/2=6$ and taking its positive root, which is indeed equal to 3. Second, from the diagonal entries of the matrix we can extract the character histogram, $h=[h_1, h_2, h_3]$, of the entire sequence. This can be achieved by solving the quadratic equation $h_i(h_i+1)/2=X_{ii}$ for $i=1, 2, 3$. From this calculation it is clear that $h=[1, 1, 1]$, i.e., each of the letters A, B, and C occurs exactly once in the sequence. Indeed, the frequency for the $i^{th}$ character in the alphabet can be calculated from the following formula:

$$h_i = \frac{-1+\sqrt{1+8X_{ii}}}{2}, i=1,\ldots,M. \tag{13}$$

Indeed, the relationship between the diagonal elements to the frequency counters is represented by the following table:

TABLE 3

| $X_{ii}$ | 0 | 1 | 3 | 6 | 10 | 15 | 21 | 28 | 36 | 45 | 55 |
|---|---|---|---|---|---|---|---|---|---|---|---|
| $h_i$ | 0 | 1 | 2 | 3 | 4 | 5 | 6 | 7 | 8 | 9 | 10 |

Next, the row sums of the matrix can be calculated by adding the open bigram counters in each row. The row and column sums for the SSM matrix is shown in FIG. 16. Finally, the total order of the characters in the sequence can be reconstructed by sorting the row sums in descending order. In this case, the sorted order is: C=3, A=2, and B=1. Thus, the original sequence is CAB.

An intuitive explanation as to why this sorting method works is as follows. The first character in any sequence of length T forms T open bigrams with all other characters, including one with itself. The second character forms T−1 open bigrams, the third one forms T−2, and so on. Finally, the last character forms only 1 open bigram with itself. Thus, for a sequence with unique characters, like the one used in this example, the reconstruction task is trivial using the methods of embodiments of the present invention.

It is worth pointing out that if all characters of the sequence are unique, then the column sums of the matrix can also be used to reconstruct the sequence. In this case, however, the column sums must be sorted in increasing order. Otherwise, the reversed sequence BAC is obtained. The reason for this is that the last letter in a sequence of length T is the right character in T open bigrams that it forms with all previous letters, including one with itself. The last but one letter forms T−1 open bigrams, and so on. The first letter forms only 1 open bigram with itself. Thus, the first letter will have the lowest sum among the columns, while the last letter will have the highest.

The embodiment of the unrolling method described so far works only for matrices constructed from sequences in which all characters are unique, i.e., each character occurs only once in the sequence. When the sequence has repeated characters, however, reconstructing it from the matrix using this embodiment is not possible. To illustrate this, FIG. 17 shows another SSM matrix, along with its row and column sums.

One thing that can been seen about this matrix is that both row B and column B contain only zeros. Thus, the original sequence does not contain the character B. If the row sums are sorted in decreasing order, then the sequence DECA is obtained. On the other hand, if the column sums are sorted in increasing order, then the sequence CADE is obtained. Thus, two different 4-letter sequences are obtained. From the diagonal elements of the matrix, however, it is known that the original sequence has 6 letters, with A and B occurring once and D and E occurring twice. After some guessing it can probably be figured that the original sequence was DECADE. In more complicated examples, however, guessing becomes very difficult as two or more characters may have the same row and/or column sums. Furthermore, guessing is not the same as having a principled method that will work in all cases.

Fortunately, embodiments of the method of the present invention provide more elegant approaches for unrolling a sequence from its SSM matrix. They will be introduced shortly, but first some properties of SSM matrices will be described. These properties explain how the matrix changes as we insert new characters or delete existing characters from the sequence, either from the end or from the beginning of the sequence. These properties are described hereinbelow.

The first property helps one understand how the SSM matrix associated with a sequence changes if a character is appended at the end of the sequence. It turns out that the matrix for the new sequence can be computed incrementally from the matrix for the original sequence. Furthermore, the changes to the matrix are quite minimal as the elements of only one column have to be modified. The updated column corresponds to the character that is being inserted. Thus, only M of the $M^2$ elements of the matrix have to be updated.

Figures 18, 19:
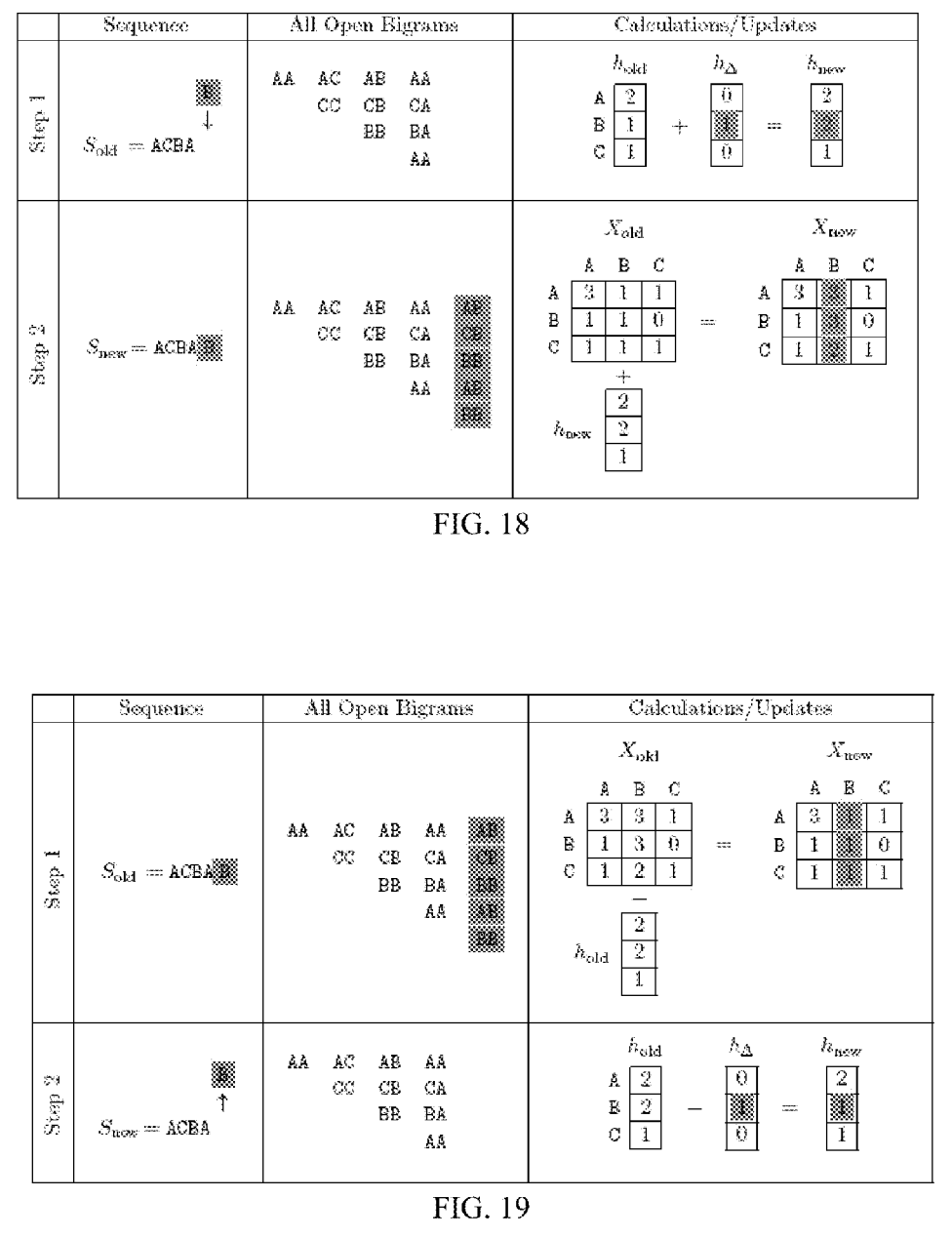

The FIG. 18 shows one example in which the character B is inserted at the end of the sequence ACBA. This results in the sequence ACBAB, which has an SSM matrix that is different from the matrix of the original sequence. The new matrix, however, can be derived from the old matrix in two easy steps. First, the histogram vector of the old sequence is modified by adding one to the bin counter that corresponds to the character that is begin inserted (B in this case). Second, the updated histogram vector is added to the B column of the matrix. That is it.

In other words, appending a character at the end of the sequence is equivalent to running the SSM encoding algorithm for one more iteration. If the histogram vector is not available, then it can be extracted from the diagonal elements of the matrix as described above.

This FIG. 18 illustrates how the SSM matrix for the sequence ACBA changes when the character B is inserted at the end of the sequence. First, the histogram vector is updated by adding one to the bin that corresponds to B, which is the character that is appended to the sequence. Second, the new matrix is obtained from the old matrix by adding the updated histogram vector to the elements of the column that corresponds to B. The entities that are added or modified during each of the two steps are highlighted in FIG. 18.

Another interesting question is what happens to the elements of the SSM matrix if the last character of the sequence that is associated with the matrix is deleted. It turns out that in this case the new matrix can also be computed using a two-step process that reverses the order of the operations described in the previous example. First, the current histogram vector is subtracted from the matrix column that corresponds to the character that is being deleted. Second, the element of the histogram vector that corresponds to the deleted character is decremented by one.

FIG. 19 shows an example that illustrates these two operations. In this example, the character B is deleted from the end of the sequence ACBAB. The new sequence is ACBA, which has the SSM matrix $X_{new}$. Removing the last character removes five instances of open bigrams in which B is the right character (they are highlighted as shown in FIG. 19).

The new matrix is obtained by subtracting the histogram vector for the old sequence from the elements of column B of the old matrix. Bin B of the histogram is then decremented by one. The modified entries of the matrix and the histogram are highlighted. In the general case, only M of the $M^2$ elements of the matrix need to be modified, along with one element of the histogram vector. Thus, the new matrix can be computed quite efficiently from the old matrix.

In FIG. 19 an example of how the SSM matrix changes after deleting the last character of the sequence associated with the matrix is illustrated. First, the histogram vector for the original sequence ACBAB is subtracted from the B column of the SSM matrix, i.e., the column that corresponds to the character that is being deleted. Second, the histogram bin counter that corresponds to B is decremented by one. The entities that are deleted or modified during each step are highlighted.

Figure 20:
FIG. 20 is a tabular flow diagram illustrating an effect of insertion of a character at the beginning of a sequence on the open bigrams and on an SSM matrix in accordance with an embodiment of the present invention.

Next, what happens to the matrix if a character is inserted at the beginning of the sequence is examined. FIG. 20 shows an example in which the original sequence is CBAB. Inserting the character A at the beginning of this sequence adds five instances of the open bigrams AA, AC, AB, AA, and AB (these are highlighted in FIG. 20). In other words, the newly inserted character forms four open bigrams with the four characters of the original sequence and one open bigram with itself.

Because the left character in all of these open bigrams is A, it may be determined from the foregoing that only row A of the matrix will be affected. Once again, the changes to the matrix can be calculated in two steps. First, the element of the histogram vector that corresponds to A is incremented by one. Second, the updated histogram vector is added to the elements of the matrix row that corresponds to the character that is being inserted.

In other words, this procedure is identical to the one described above, except in this case the histogram vector is added to the corresponding row instead of column. Another way to explain this swapping of rows with columns is to remember that reversing the sequence transposes the matrix. Thus, appending a character at the end of the reversed sequence will add the histogram vector to the corresponding column; reversing the sequence again will cause these changes to appear in the corresponding row of the matrix.

FIG. 20 illustrates how the SSM matrix for the sequence CBAB changes when the character A is inserted at the beginning of the sequence. The new matrix is calculated in two steps. First, the histogram bin counter that corresponds to the new character (A in this case) is incremented by one.

Second, the updated histogram vector is added to the A row of the matrix. The components that are inserted or modified at each step are highlighted.

Figure 21:
FIG. 21 is a tabular flow diagram illustrating an effect of deletion of a character at the beginning of a sequence on the open bigrams and on an SSM matrix in accordance with an embodiment of the present invention.

The last property that is discussed before describing the unrolling algorithms shows what happens to the elements of the matrix if the first character of the sequence is deleted. FIG. 21 gives an example with the sequence ACBAB. Deleting the first A from this sequence is equivalent to removing the following five instances of open bigrams: AA, AC, AB, AA, and AB (they are highlighted in FIG. 21).

Because A is the left character in all five of these open bigram instances only row A of the matrix will be affected by this deletion. Again, the new matrix can be calculated from the old matrix using a two-step procedure. First, the histogram vector of the original sequence is subtracted from the elements of row A of the matrix. Second, the counter for bin A of the histogram is decremented by one. In other words, the order of operations is reversed (relative to the one described in the previous example) and plus is replaced with minus.

FIG. 21 shows an example of how the SSM matrix for the sequence ACBAB changes when the character A is deleted from the beginning of the sequence. The new matrix can be computed from the old matrix in two steps. First, the histogram vector for the old sequence is subtracted from row A of the old matrix. Second the histogram bin counter that corresponds to the deleted character is decremented by one. The entities that are deleted or modified are highlighted.

As discussed above the first character of a sequence can be extracted from its SSM matrix if one row of the matrix from which to subtract the histogram vector can be found without any of the matrix elements becoming negative. It has been shown that in every SSM matrix there is at least one row with elements that are all greater than or equal to the corresponding elements of the histogram vector. This suggests that it might be possible to unroll the entire sequence from the matrix if the two steps described above are repeated multiple times.

FIG. 22 gives an unrolling example that uses this approach. The original matrix in this example corresponds to the sequence ACBAB. If the first character is repeatedly deleted, then the following progression of sequences is obtained: ACBAB, CBAB, BAB, AB, B, and the empty sequence. Each of these sequences has an associated matrix that can be derived from the matrix for the previous (longer) sequence. This can be achieved by subtracting the histogram vector from one of the rows of the matrix, decrementing the histogram bin counter that corresponds to the unrolled character, and then repeating this process multiple times. In other words, during the first iteration the histogram vector is subtracted from the first row, which corresponds to the character A. During the second iteration it is subtracted from the third row, which corresponds to C, and so on until all five characters of the original sequence are unrolled. The elements of the matrix that are modified during each iteration are highlighted in red. The unrolling ends when a matrix is reached that contains only zeros, which corresponds to the empty sequence.

Notice that in this example the unrolling process is completely deterministic. In other words, during each iteration the histogram vector can be subtracted from one and only one row of the matrix without any of its entries becoming negative. Furthermore, the order in which the characters are unrolled matches exactly their order in the sequence ACBAB, which was used to construct the original matrix. After the last character is unrolled the matrix contains only zeros and the histogram vector contains only zeros as well. Each of these can be used as a termination condition in case the sequence length is unknown.

In FIG. 22 the example of unrolling the sequence ACBAB from its SSM matrix by repeatedly subtracting the histogram vector from one of the rows of the matrix without any matrix elements becoming negative is illustrated. This process is repeated until the matrix contains only zeros. The matrix elements highlighted are the only ones that are modified during each iteration. The character that is unrolled at each iteration is shown in the right column. After each iteration the histogram bin counter that corresponds to the unrolled character is decremented by one. The unrolled sequence matches the sequence that was used to construct the original SSM matrix. Notice that in this example the unrolling is completely deterministic as the histogram vector can be subtracted from one and only one row of the matrix during each iteration.

By this point it should be apparent that the sequence can also be unrolled in reverse (i.e., starting from the last character) by repeatedly applying the procedure described above. That is, by repeatedly subtracting the histogram vector from the columns of the matrix and then decrementing the corresponding histogram bin counter by one.

FIG. 23 shows an example with the matrix for the sequence ACBAB. Once again, the system makes sure that none of the matrix elements becomes negative. This condition restricts the columns from which we can subtract the histogram vector during each iteration. In this case the unrolling is also fully deterministic as the histogram vector can be subtracted from only one column during each iteration.

The first character that is unrolled is B because the histogram vector $h=[2, 2, 1]$ can only be subtracted from the B column of the original SSM matrix. In other words, only the elements of the second column of the matrix are all greater than or equal to their corresponding elements of the histogram vector. After the first iteration the histogram bin counter for the character that was just unrolled (i.e., B) is decremented by one. That is, before the start of the second iteration the histogram vector is equal to $h=[2, 1, 1]$. At this point the newly updated histogram vector can be subtracted only from the first column of the matrix, which corresponds to the character A. As shown in FIG. 23, this process can be repeated for three more iterations. After the last iteration the matrix contains only zeros. The histogram vector also contains only zeros after the fifth iteration (not shown in FIG. 23).

The sequence that is unrolled using this process is BABCA. If this sequence is read in reverse, then the sequence ACBAB is obtained, which was used to construct the original SSM matrix (i.e., the one used during the first iteration in FIG. 23).

FIG. 23 shows an example of unrolling the sequence ACBAB in reverse by repeatedly subtracting the histogram vector from one of the matrix columns without any of the matrix elements becoming negative. After each iteration the histogram bin counter that corresponds to the unrolled character is decremented by one. The unrolling process in this example is fully deterministic as the histogram vector can be subtracted from one and only one column of the matrix during each iteration. The unrolled sequence is BABCA, which is the reverse of the original sequence ACBAB that was used to construct the SSM matrix.

While the embodiment of the unrolling algorithm just discussed is relatively straightforward, its computational complexity is not very nice. It runs in $O(TM^2)$ time because the second function has two nested loops, each with up to M iterations. The SSM encoding algorithm, however, runs in O(TM) time as discussed above. Ideally, it is desirable to have a decoding (or unrolling) algorithm that has the same computational complexity. Otherwise, the decoding will be slower than the encoding by a factor of M.

Fortunately, it is possible to derive a faster algorithm by maintaining a helper variable $\gamma_i$, one for each row of the matrix. This algorithm is very similar to the previous one, but instead of checking all $M^2$ elements of the matrix it checks only the M elements of the $\gamma$ array. Each $\gamma_i$ contains the number of elements in the i-th row that are greater than or equal to the corresponding elements of the histogram vector. Because each row has exactly M elements, the maximum value of $\gamma_i$ is M. Thus, the histogram vector can be subtracted from the i-th row if and only if $\gamma_i$ is equal to M. Some additional maintenance is required for the $\gamma$ array as the histogram is always decremented after each iteration. This is done in a separate loop that checks the elements of the i-th column of the matrix to see if any other rows may become eligible for unrolling during the next iteration. In other words, if $X_{ji}$ is equal to $h_i-1$ after successfully subtracting h from the i-th row, then $\gamma_j$ is incremented by one, where j=1, 2, . . . , M.

Once again, it is possible to state a version of the fast algorithm that unrolls the sequence in reverse. This algorithm, however, is not stated here as it is relatively straightforward to derive it from the foregoing.

While the above examples were deterministic, the embodiment of the method of the present invention used therein can get stuck for certain classes of sequences. It is possible to modify this method, though, by using a standard technique from computer science called search with backtracking The basic idea is to try something and if it leads to a dead end to backtrack your steps and make a different choice. Many problems in computer science are solved using this trial-error-backtracking approach, including the famous 8 queens problem.

Given an SSM matrix, this embodiment unrolls all sequences that map to this matrix (in case there is more than one). If the matrix is a proper SSM matrix, i.e., if it was derived from a real sequence, then this embodiment is guaranteed to unroll that sequence.

This embodiment of the method of the present invention loops through the rows of the matrix and tries to find a row in which all elements are greater than or equal to the corresponding elements of the histogram vector. If such a row is detected, then the method subtracts the histogram from that row, appends the character associated with that row to the partially unrolled sequence, and then tries to unroll the remaining matrix using a recursive call.

If a recursive call fails, then the method undoes the latest changes by adding the histogram back to the row from which it was subtracted. It then tries to find another row. If all rows fail, then the current recursive call fails. If all recursive calls at the top level of the recursion fail, then the matrix cannot be unrolled, but that should never happen if the matrix was constructed from a sequence. If the method finds a sequence, then it prints it and attempts to find other sequences, treating the solution as just another backtracking step. The method prints all sequences that map to the input matrix. It prints nothing if it fails.

It is also possible to state another embodiment of the backtracking method that unrolls the sequence in reverse. This is not difficult to do as the same operations that were described above now have to be performed on the columns of the matrix instead of on the rows. This algorithm will not be stated explicitly as it is easy to derive it from the discussion above.

To see why the backtracking embodiment always succeeds while the prior embodiment may get stuck, it should be remembered that the SSM encoding algorithm builds the matrix by incrementally by adding the histogram to the appropriate column of the matrix during each iteration. The unrolling algorithm has to do this but in reverse (in case of backward unrolling). Due to aliasing effects in the matrix, however, it may not be immediately obvious which is the next character that must be unrolled. Because the order of unrolling matters, making a bad choice may lead to a dead end from which the system must backtrack. The search space is a tree where at each node it may be possible to unroll up to M different characters. In practice, however, this is never the case. Typically, there will be at most 2-3 characters that could be unrolled during each iteration. In the case of forward unrolling the role of columns and rows is swapped, but the same principle applies.

In a further embodiment of the present invention, two discrete sequences that unfold in parallel may be used with dual-band SSM. From Psychology it is known that most forms of learning are inherently multimodal. In other words, the learner can easily make associations between signals that are coming from at least two different sensory modalities. For example, in Pavlovian conditioning experiments, a restrained dog can learn that a bell (auditory stimulus) can predict the arrival of food (gustatory stimulus). In operant conditioning experiments, a rat in a Skinner box can learn that by pressing a lever (motor action) it can turn on a light (visual stimulus). In many of these experiments, the two signals can be modeled as discrete sequences that unfold concurrently over time. In other words, the continuous-time signals are modeled as discreet-time sequences. One of the main goals of this field is to formulate and test different theories about the mechanisms that make perception, learning, and memory possible. The exact nature of these mechanisms is still unknown, with competing theories favoring different ones (e.g., associations, probabilities, or temporal contingencies). There is no doubt, however, that biological brains can extract invariants from multiple sensory channels.

The discussion of this further embodiment describes how the notion of open bigram and the notion of SSM matrix can be generalized and used to extract invariants from two concurrent sequences. This new representation will be referred to herein as dual-band SSM, or dual-sequence SSM, or just dual SSM for short.

Two discrete sequences that unfold in parallel over time can be encoded into a dual SSM matrix. The two sequences may come from two different sensory modalities (e.g., audio and proprioception) or from two sub-channels or bands of the same sensory modality (e.g., low and high auditory frequencies). For the moment, this discussion will ignore the question about the origin of the sequences and will only focus on describing how the matrix can be constructed. The SSMs and SSM cascades recognizing these invariants allow for building an associative and autoassociative memory, e.g., building, maintaining and querying a hierarchical associative and autoassociative memory.

To distinguish between the two sequences the English alphabet will be used for the characters of one of them and the Greek alphabet for the characters of the other one. In addition to making the distinction between the two sequences more obvious, this convention also emphasizes the fact that the two sequences are truly different from one another. Because the sequences could come from different sensory modalities, comparing characters from different sequences is like comparing apples with oranges. Therefore, different alphabets will be used to emphasize this.

FIG. 24 shows and example with the English word SIGMA and the Greek word δελτα (delta). The middle column shows all open bigrams that can be formed by the characters of these two sequences. Because in the dual case there are two sequences, however, the notion of open bigram is generalized in the following way. An open bigram is still formed by only two characters, but the left character can only come from the first sequence (the one using the English alphabet), while the right character can only come from the second sequence (the one using the Greek alphabet). For example, the open bigram Sλ means that the character S from the first sequence occurred temporally before the character λ from the second sequence. An open bigram can also be formed by two characters that occur simultaneously. One such example is Sδ, as S and δ are the first characters in the two sequences. What is still not allowed, however, is for the right character in any open bigram to occur temporally before the left one.

The last column in FIG. 24 shows the dual SSM matrix. It is similar to a regular SSM matrix, but in this case the rows are labeled with the English characters of the first sequence, while the columns are labeled with the Greek characters of the second sequence. As before, the convention of sorting the row and the column labels in the dual SSM matrix in alphabetical order is adopted.

In the previous example the order of the two sequences was somewhat arbitrary. In other words, it was assumed that the English sequence was the first one, but there was no real justification for this assumption. By swapping the two sequences, however, another set of open bigrams and another dual SSM matrix can be obtained. FIG. 25 shows an example with the two words δελτα and SIGMA. In this case, the left character in each open bigram comes from the Greek sequence and the right character comes from the English sequence. Notice that this matrix is different from the one shown in FIG. 24. In other words, when working with dual SSMs the order of the input sequences does matter.

In fact, given two different sequences S' and S" there are four dual SSM matrices that can be computed, one for each of the four possible pairs of sequences: S'S', S'S", S"S', and S"S". FIG. 26 gives an example and shows the four sets of open bigrams when S'=SIGMA and S=δελτα. The four corresponding SSM matrices are shown in FIG. 27. All four of these matrices can be collectively used as a representation for the two sequences. As will be discussed later, this additional information can be used to improve the accuracy of sequence recognition tasks. It can also be used to predict one sequence given the other and vice versa.

The two off-diagonal boxes in FIG. 27 contain the two dual SSM matrices that were already shown above. The two diagonal boxes in FIG. 27 contain matrices that are equivalent to two single SSM matrices constructed from the sequence SIGMA and the sequence δελτα, respectively. In other words, a dual SSM matrix constructed from two identical sequences is equivalent to a single SSM matrix constructed from that same sequence.

In the previous example it was assumed that both sequences have the same length and that they both have the same number of unique characters. As a general rule, however, in the dual case, the sizes of the two alphabets do not have to be the same and also the number of unique characters in the two sequences does not have to be the same. Therefore, dual SSM matrices do not have to be square matrices. To illustrate this, FIGS. 28 and 29 provide another example with the English word DELTA and the Greek word γαμμα. The first word has five unique letters, while the second one has only three. Because the Greek word has two repeated letters (α and μ) the off-diagonal boxes in FIG. 29 contain dual SSM matrices that are not square.

The four sets of open bigrams that can be formed by the characters of the two sequences S'=DELTA and S"=γαμμα for the four possible pairs of sequences S'S', S'S", S"S', and S"S" are shown in FIG. 28.

The four dual SSM matrices that can be constructed from the characters of the two sequences S'=DELTA and S"=γαμμα, one for each of the four possible pairs of sequences: S'S', S'S", S"S', and S"S" are shown in FIG. 29. Because the two sequences have different number of unique characters some of the resulting matrices are not square.

Given three sequences S', S", and S''' there are nine possible sequence pairs that can be formed: S'S', S'S", S'S''', S"S', S"S", S"S''', S'''S', S'''S", and S'''S'''. A separate SSM matrix can be constructed for each of these pairs. FIG. 30 gives one example for S'=DELTA, S"=31415, and S'''=γαμμα. The first sequence has 5 unique characters, the second one has 4, and the third one has only 3. Because of these differences, the matrices have different dimensions and the off-diagonal boxes contain non-square matrices. The four matrices in the four corners of FIG. 30 are the same as the ones shown in FIG. 29.

Obviously, this concept can be generalized to more than 3 sequences. Given n different sequences, there can be formed $n^2$ pairs of sequences and a dual SSM matrix for each of them can be constructed. Exactly n of these matrices will be equivalent to single SSM matrices. The remaining $n^2-n$ will be dual SSM matrices that do not necessarily have to be square. Even though each matrix couples only two sequences, all $n^2$ matrices can be collectively used to capture the invariants between the n sequences.

From the previous examples it should be clear that the number of byproducts of any dual encoding algorithm could be quite large. The following introduces a notation for describing these byproducts. A discrete dual SSM model in which the two sequences are presented in parallel, have the same length, and are sampled at the same frequency typically has the following set of inputs. S' is the first sequence, its length is T, and its alphabet is $\Gamma' \in \{a_1, a_2, \ldots, a_{M'}\}$. S" is the second sequence, its length is T, and its alphabet is $\Gamma'' \in \{b_1, b_2, \ldots, b_{M''}\}$.

Some of the possible outputs of a dual encoding algorithm include the following. h(S') is the histogram of the first sequence, which could also be denoted with h'. h(S") is the histogram of the second sequence, which could also be denoted with h". X(S') is the single SSM matrix for the first sequence S'. X(S") is the single SSM matrix for the second sequence S". D(S', S") is the dual SSM matrix that counts open bigrams $a_i b_j$ such that $t_{ai} \leq t_{bj}$. D(S", S') is the dual SSM matrix that counts open bigrams $b_i a_j$ such that $t_{bi} \leq t_{aj}$. H(S', S") is the histogram of pairs of characters $a_i b_j$ that occur together in time, i.e., $t_{ai}=t_{bj}$. Finally, H(S", S') is the histogram of pairs of characters $b_j a_i$ that occur together in time, i.e., $t_{bj}=t_{ai}$.

Thus, there is a whole family of encoding algorithms depending on which of these they output. In other words, it is not necessary to output all of them. Similarly, the algorithm may output additional byproducts that enforce additional constraints.

There is a distinction between which components go into a dual model and which of these components can be inferred from the other components. For example, a dual model may include both h(S') and X(S'), i.e., both the histogram and the single SSM matrix for the first sequence S'. As is known from the foregoing description of the single SSM theory, however, it is possible to derive h(S') from X(S'). Thus, any model that includes both will contain some redundant information. But extracting the histogram from the matrix requires some computation. If it cannot be afforded to perform this computation every time or if this computation requires operations (e.g., taking a square root) that are not feasible in a specific embodiment of this model, then both components should be part of the model.

Here are some inference rules that the preceding description makes clear. Given X(S'), one can infer h(S'). Given X(S"), one can infer h(S"). Given h(S'), h(S"), D(S', S"), and H(S', S"), one can infer D(S", S'). Given h(S'), h(S"), D(S", S'), and H(S', S"), one can infer D(S', S"). The formulas for these rules are as follows:

$$D_{ji}(S'', S')=h_i(S') \cdot h_j(S'')-D_{ij}(S', S'')+H_{ij}(S', S''). \quad (14)$$

$$D_{ij}(S', S'')=h_i(S') \cdot h_j(S'')-D_{ji}(S'', S')+H_{ij}(S', S''). \quad (15)$$

With the preceding in mind, the following provides several examples of dual models that can be unrolled. It will be assumed that the components that go into each model are all part of that model, even if some of them can be derived from the others. A rectangular box will be put around the components of each model. Arrows will be used to denote what can be unrolled from each model.

With this convention, the first example starts with the familiar single SSM model. Using this new notation it can be represented as shown in FIG. 31. In other words, this model is trained on the sequence S and the model contains both the single SSM matrix as well as the histogram for this sequence. As is known from the previous discussion, the sequence S can be unrolled from this model, which is denoted with the arrow coming out of the box.

In the dual case, we have two input sequences: S' and S". Depending on which one is to be unrolled, there are different models that can be used. FIG. 32 illustrates some of them. It is also possible to unroll both sequences at the same time in parallel as shown in FIG. 33. These models contain all components except H(S', S") and H(S", S'). As it turns out these are not needed in order to unroll in this embodiment.

As the number of potential byproducts of any dual encoding algorithm is fairly large, it is natural to pose the question: What is the minimum number of components that is necessary for unrolling? In the dual case, however, there are two sequences. So when unrolling is discussed, it should be mentioned explicitly which of the two sequences is desired to be unrolled: S' or S". The minimum dual model that has been identified so far is shown in FIG. 34.

In other words, this model has only two components: a dual matrix D(S', S") and the histogram for the second sequence h(S"). Given this model it is possible to unroll the first sequence S'. This is only possible, however, if the second sequence S" is presented to the model as well. Note that S" is not part of the model, but it is required at run time for unrolling.

In light of the original inspiration for the dual model, i.e. Pavlovian conditioning, this model makes a lot of sense. In Pavlovian conditioning experiments the animal is trained by presenting two sequences on two different channels. During testing, however, only one sequence is presented. Nevertheless, the animal is able to anticipate the other sequence, which leads to certain physiological responses (e.g., salivation). FIG. 35 shows another example that flips the input and the output sequences.

The dual unrolling algorithms presented in this embodiment are all of this form. In other words, they require a sequence at run time. Algorithms for unrolling the other embodiments of the models that have additional components can also be stated.

FIG. 36 gives an example that illustrates how this embodiment of the dual encoding algorithm works. The two sequences in this example are S'=βαγβ and S"=ABAB. These two sequences unfold in parallel and they are read by the system one character at a time from left to right (see the second column in FIG. 36). The third column of this FIG. 36 shows the dual open bigrams that have been formed up to the current time. The fourth column shows how the histogram vector h' for the first sequence S' evolves over time. The dual matrix shown in the fifth column is constructed by incrementally adding the value of this histogram vector to the appropriate column of the matrix during each iteration. The appropriate column is selected by the current character from the second sequence.

The last row of FIG. 36 shows the fourth iteration of the algorithm. Certain elements are highlighted to better illustrate how the encoding works. For example, the last letter of the first sequence, β, is highlighted. The second bin of the histogram vector, which corresponds to β, is also highlighted to indicate that this bin counter was incremented by one during this iteration. The last character of the second sequence, B, is highlighted. The matrix column that corresponds to B is also highlighted to indicate that the recently updated histogram vector h' was added to this column. Thus, during each iteration the elements of only one column of the matrix are updated. This gives the algorithm its O(TM') computational complexity, where M' is the size of the first alphabet (the Greek alphabet in this case).

Notice that even though there are four new open bigrams (βB, αB, γB, βB) that are added during the last iteration, they can be counted using only three additions (i.e., adding the histogram vector to the B column of the matrix). They are highlighted in the middle column of FIG. 36. But notice that the open bigram βB occurs twice in this list. The histogram, however, contains only three bins. Thus, the histogram vector implicitly counts the open bigrams. This property gives the encoding algorithm its nice computational complexity.

To summarize, during each iteration, the incoming character from S' is used to find which bin counter must be incremented in h'. On the other hand, the incoming character from S" selects the matrix column to which h' must be added. Note that in the single SSM case, the same character selected both the histogram bin and the matrix column. In the dual case, these two roles are decoupled.

FIG. 37 shows all three dual components that this embodiment of the encoding algorithm returns. These also include the histogram vector h" for the second sequence. As will be seen later, only the dual matrix D(S', S") and the histogram h" are required for unrolling. The histogram vector h', however, is required for encoding.

FIG. 38 illustrates another dual encoding example. In this case, the sequence S' is the same as in the previous example. The sequence S" is different (S"=BBBA), but the resulting dual matrix is the same as the one shown in FIG. 37. The histogram vector h' is also the same in both examples. There is a second histogram vector h" shown in FIG. 39 and the vector is different from h" in the previous example. As will be seen later, the unrolling algorithm for D(S', S") uses h". So even though the matrix is the same as in the previous example, the sequence S' can be uniquely unrolled if the sequence S" is presented at run time.

As will now be apparent, this embodiment of the unrolling algorithm is different from the ones for the single SSM. It uses one of the sequences at run time. In the single case a sequence was not needed. The histogram was enough. In this case, however, the dual model includes the dual matrix D(S', S") and the histogram h(S") for the sequence. In order to unroll, this algorithm requires the sequence S" to be provided at run time. The algorithm unrolls the sequence S'. The schematic diagram of the dual unrolling algorithm presented in this example is shown in FIG. 34. Once again, there are multiple other embodiments of dual unrolling, depending on what goes in the model. This section presents only one type.

Figures 41, 42, 43:
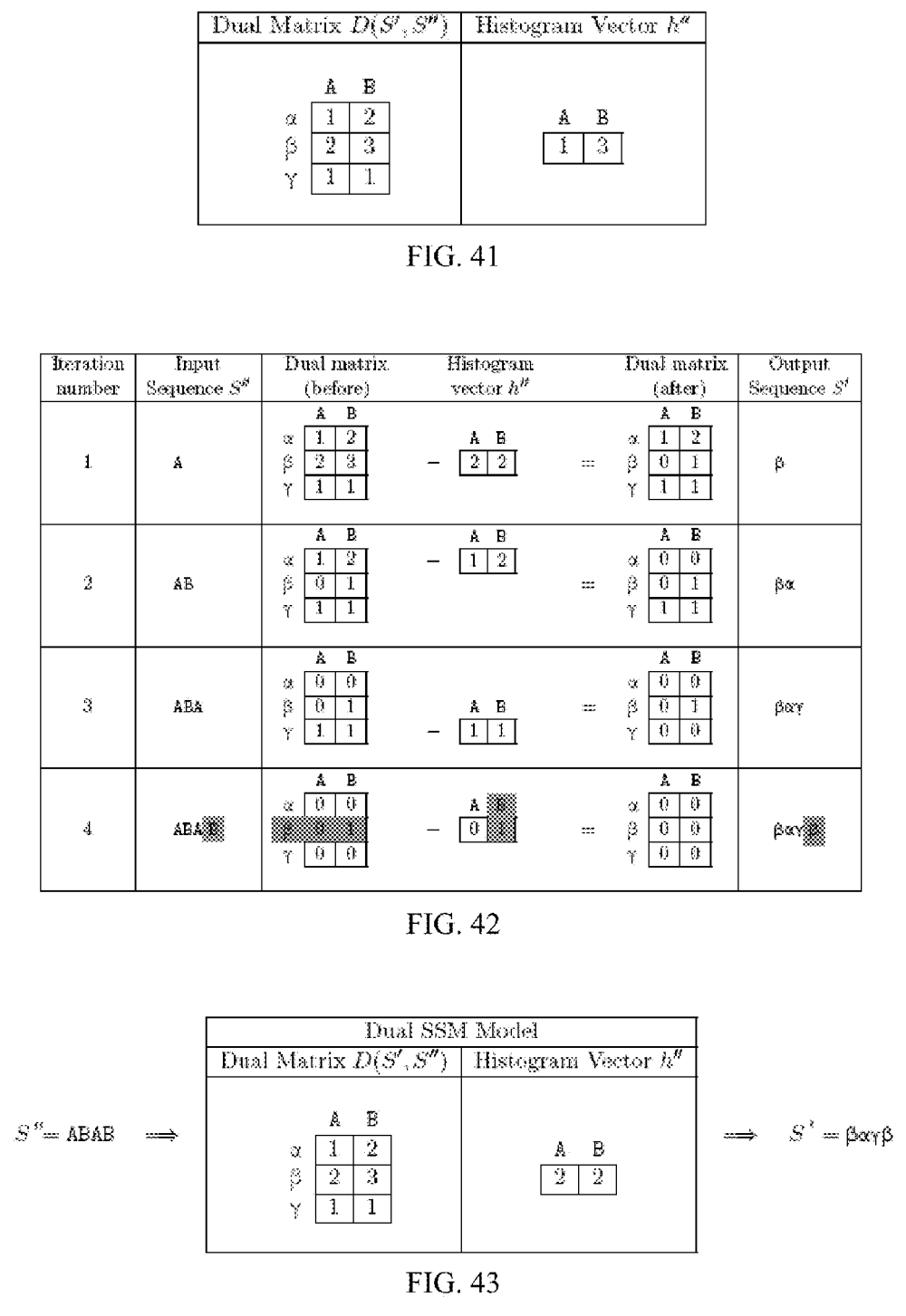

FIG. 40 illustrates the minimal dual model for S'=βαγβ and S"=ABAB that can be unrolled. Doing this, however, requires the sequence S" at run time. In other words, this FIG. 40 shows the minimum dual model that can be used to unroll the sequence S' from the dual matrix D(S', S"). FIG. 41 shows the minimal dual model for S'=βαγβ and S"=BBBA that can be unrolled. If the sequence S" is presented at run time, then it is possible to unroll S'.

With this understanding in mind, FIG. 42 illustrates the unrolling process for the dual matrix D(S', S") that was constructed from the two sequences S'=βαγβ and S"=ABAB. During each iteration the histogram vector h" for the second sequence is subtracted from the rows of the matrix. The character that corresponds to that row is unrolled. The bin counter in h" that corresponds to the incoming character from S" is decremented by one. This process is repeated until the matrix contains only zeros.

FIG. 43 shows a diagram of the unrolling problem, to wit, given the dual matrix D(S', S"), the histogram vector h", and the sequence S", the task is to unroll the sequence S'.

Unrolling of the second example discussed above, i.e. S'=BBBA and S"=βαγβ, is shown in FIG. 44, and the dual unrolling problem is shown in FIG. 45.

FIG. 46 shows yet another forward unrolling example. The dual matrix D(S', S") in this case is constructed using the sequence S'=γαμμα and S"=DELTA. The characters from the second sequence S" are provided one at a time at run time in order to unroll the characters of the first sequence S'.

While the preceding examples unrolled the sequences in a "forward" direction, FIG. 47 illustrates that such dual unrolling may be conducted in the "reverse" direction as well. That is, when the dual matrix D(S', S") is constructed from the two sequences S'=γαμμα and S"=DELTA, given the reverse of the first sequence, i.e. $(S')^R$, it is possible to unroll the reverse of the second sequence, i.e. $(S")^R$.

The following illustrates one embodiment of matching the dual SSM matrix for two parallel sequences S' and S" to the closest entry in an array A of dual SSM matrices. This embodiment utilizes a simple linear search through an unsorted array of matrices. Several optimizations are possible as will be recognized by those skilled in the art. For example, the search can be parallelized by splitting the array A and letting a separate processor or core handle the segments. Methods for pruning the search space can also be exploited. For example, on a massively parallel architecture each node may be encoding its own local version of the dual SSM matrix and subtracting it at each step (after each new character) from the already encoded matrix Ai. If at any point in time the system gets a negative number, then that would mean that the current matrix cannot be encoding for this pair of sequences.

As with the single SSM matrices discussed above, a distance measure can be defined between two dual SSM matrices. In one embodiment, the Euclidean distance between two dual SSM matrices is calculated.

Another distance measure can be computed in a further embodiment based on the symmetrized KL-divergence between the two distributions of open bigrams. This metric was discussed above for the single SSM matrix embodiments. This embodiment is similar to the embodiment discussed above which computes the distance between two single SSM matrices. The main difference in this case is that the two matrices are of size M'×M" instead of M×M. The complexity of this algorithm is O(M'M"), which reduces to $O(M_2)$ if the two alphabets are of equal size.

In yet another embodiment, the distance measure can be computed using the asymmetric KL-divergence metric. As before, the open bigram probabilities need to be smoothed before these measures can be calculated. One way to do this is additive smoothing.

In the dual examples that have been discussed so far, the two sequences always unfolded simultaneously over time. Thus, even though it was possible to predict S' given S", the prediction was always for the current time step. Predicting even a few characters into the future is not possible with the embodiments of the models discussed so far.

However, in a further embodiment to be discussed below, this limitation can be overcome. To illustrate this, the single sequence example shown in FIG. 48 is used. In this example the sequence S is split into two segments $S_A$ and $S_B$. The two segments can then be aligned as shown in the middle part of FIG. 48. Finally, a dual matrix $D(S_B, S_A)$ can be constructed. Note that the B segment is the first one.

The goal is to construct a dual SSM model such that given the sequence $S_A$, the sequence $S_B$ can be predicted (or unrolled). One such model is shown in FIG. 49. In this example the sequence was encoded against itself. From a practical point of view, however, this requires buffering the two segments before the dual matrix can be encoded. If there are two different sequences S' and S" that unfold in parallel over time, however, the buffering problem can be resolved with a cascade of dual models. FIG. 50 shows two sequences that are each split into two segments. Several dual SSM matrices can then be encoded using the separate segments.

With these two sequences, the cascade shown in FIG. 51 can then be defined. In other words, given $S'_A$ (the first part of S') it is possible to infer the second half $S'_B$. Two dual models are used in this case and the sequence S" is used as a helper sequence in order to do the dual encoding.

Arbitrarily complex cascades can be constructed in this way. They can include not only two sequences, but multiple ones. By choosing/fixing specific sequences in these cascades it is possible to accomplish complex control logic.

In a further embodiment of the present invention, sequences that have different lengths are accounted for. If the two discrete sequences are sampled at the same rate, but one of them is longer than the other, then they can be aligned by adding dummy characters to the end of the shorter sequence or by truncating the tail of the longer sequence. After this alignment an SSM matrix can still be computed without modifying any of the algorithms.

In the previous examples it was assumed that the two sequences were sampled at the same rate and thus have equal lengths (in terms of the number of characters). In practice, this assumption is unrealistic for sequences coming from different sensory modalities as one of the sequences may come from a fast varying signal, while the other one may come from a slow varying signal. For example, audio signals are typically sampled at 44.1 KHz, while tactile signals are sampled at 10 Hz. This embodiment relaxes this assumption and shows how an SSM matrix can still be encoded when the sequences are sampled at different frequencies.

FIG. 52 gives an example with two sequences in which the sampling frequency for the second sequence is two times higher than the frequency used for the first sequence. In this case open bigrams can still be formed, but the rule for forming an open bigram needs to be clarified.

FIG. 53 shows three different sets of open bigrams that can be constructed from the two sequences shown in FIG. 52, depending on the discretization and rescaling rules. Essentially, it boils down to deciding when a character has been emitted: at the beginning, at the middle, or at the end of its time window. Notice that even though the second and the third sets have a smaller number of open bigrams in them, they are still proper subsets of the first one. Indeed, depending on the sampling and rescaling rules, three different sets of open bigrams from the two sequences can be obtained.

The two sequences can be rescaled to have equal lengths. Note that this does not require alignment of the two sequences similar to what dynamic timewarping tries to achieve. Instead, the two sequences are simply put into two arrays of equal size and shifts and replicates the characters of one of them so that the two sequences have equal length. This embodiment also takes care of the border effects. The algorithm returns the two rescaled sequences as two arrays of equal length. The discussion of the embodiment that utilizes a spike-based representation, below, will also describe another way to resolve the scaling issues. In that case, the requirement to have discrete sequences, or even sequences that have the same length is no longer needed.

In a further embodiment of the present invention, the concept of open bigram can be generalized to open trigram in the following way. An open trigram is defined as an ordered triple of characters that occur one after another in some sequence S, but they do not have to occur right next to each other. In other words, the open trigram characters may be separated by one or more characters in the sequence. As in the case of open bigrams, it is still allowed for a character to form an open trigram with itself. In other words, all three characters in the open trigram can be the same and they all can occur at the same location in the sequence.

Once again, it is worth emphasizing that open trigrams are different from regular trigrams, which have been widely used by others for different tasks. In regular trigrams the three characters must always occur consecutively one after another. This is not required for open trigrams. As a result of this, the number of open trigrams in any sequence is much larger than the number of regular trigrams. To illustrate this fact, FIG. 54 shows an example with the sequence S=ABCD, which has 20 open trigrams, but only 2 regular trigrams.

As can be seen from this FIG. 54, open trigrams provide a much denser sequence model. A sequence model based on regular trigrams, on the other hand, is quite sparse. It is well known that sequence models based on regular trigrams require vast amounts of data in order to be trained accurately. In contrast, a sequence model based on open trigrams can be trained from a single sequence and can still recognize the sequence in the presence of noise. This is due to the vastly greater number of open trigrams.

Another difference between the two is that regular trigrams capture the total order relationships between the characters of the sequence on a local scale, while the open trigrams capture the partial order relationships between the characters of the sequence on a global scale. Thus, dropping the total order requirement results in a much denser and much more accurate sequence model that can be trained from a single instance. This is indeed a remarkable property. Thus, the open trigrams provide a much denser model of the sequence because they capture the partial order relationships between the characters in the sequence on a global scale. In contrast, regular trigrams capture only the total order relationships between the characters in the sequence on a local scale. Because regular trigrams provide a sparse model they require large amounts of data to be trained accurately. The density of the open trigram model makes it possible to train them from just one sequence.

Figures 55, 56:
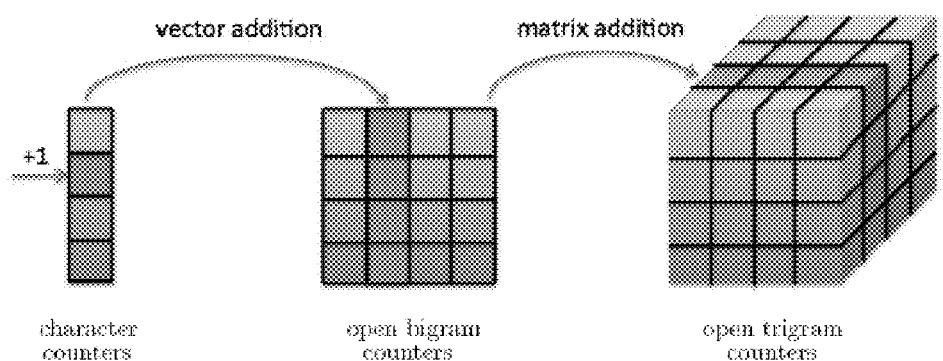
FIG. 55 is a tabular illustration of a comparison of the number of regular bigrams, regular trigrams, open bigrams, and open trigrams as a function of the sequence length.
FIG. 56 is a schematic Illustration of the incremental encoding algorithm for open trigrams in accordance with an embodiment of the present invention.

FIG. 55 compares the number of regular bigrams, regular trigrams, open bigrams, and open trigrams for sequences of different lengths. As can be seen from FIG. 55, a sequence of length T has (T−1) regular bigrams and (T−2) regular trigrams. Thus, their number is almost the same as the sequence length. In contrast, the same sequence of length T has $T(T+1)/2$ open bigrams, i.e., their number increases as the square and the cube of the sequence length. Interestingly, in any sequence, there are more open trigrams than open bigrams. For example, a sequence of length T has $T(T+1)(T+2)/3!$ open trigrams. Thus, they capture the partial order relationships between the characters of the sequence even better. As will be discussed below, this is the reason why embodiments of the present invention that utilize open trigram models outperform those that utilize open bigram models on sequence recognition tasks.

As just discussed, a sequence of length T has $T(T+1)(T+2)/3!$ open trigrams. Because this is such a large number, however, it is not immediately obvious if a sequence can be encoded in terms of open trigrams in an efficient way in order to make this representation usable for any practical applications. Fortunately, there is an elegant and computationally efficient extension of the open bigram encoding algorithm that works for open trigrams. The main idea is that for any sequence the number of open trigrams can be incrementally calculated from the number of open bigrams, which, in turn, can be incrementally calculated from the number of unigrams that are equal to the bin values of the character histogram. FIG. 56 illustrates the incremental updates that have to be performed after reading each character from the sequence.

As shown in this FIG. 56 illustrating the incremental encoding algorithm for open trigrams, the grey areas show the memory locations that must be updated after the current character from the sequence is scanned (in this example, the current character has an integer value of 2). First, the histogram vector (h) is updated by adding one to the bin counter for the current character. Second, the whole histogram vector is added to the matrix (X) column that corresponds to this character. Finally, the elements of the entire matrix are added to the 2D slice of the 3D array (Z) that corresponds to the current character. These three steps are repeated for each character of the sequence.

In other words, even though there are $T(T+1)(T+2)/3!$ instances of open trigrams in a sequence of length T, there are only $M^3$ unique open trigrams, where M is the size of the alphabet. Because the encoding algorithm counts the number of unique open trigrams it does not have to maintain a list of all instances. Furthermore, by cleverly reusing the intermediary counter values for open bigrams and unigrams the algorithm only has to update $M^2$ memory locations in the 3D array at each step. Thus, the trigram encoding algorithm runs in $O(TM^2)$ time.

FIG. 57 gives a step-by-step illustration of how this embodiment operates. The example sequence in this case is ABBA. The last three columns in FIG. 57 show the values of the three internal data structures (h, X, and Z) for each iteration of the algorithm. During the initialization step all data structures are initialized with zeros. The histogram vector h is updated first by incrementing one of its entries (the one that corresponds to the current character). The entire vector is then added to the appropriate column of the matrix X. The entire matrix is then added to the corresponding 2D slice of the 3D array Z.

The strange-looking entries in the last column represent one way to visualize the 3D array of open trigram counters by showing two separate 2D slices from that array. The first slice (the one on top) corresponds to the counters for open trigrams in which the last character is A, i.e., open trigrams of the form A. The second slice (the one on the bottom) contains the counters for open trigrams that end in B, i.e., they have the form B.

The entries that are changed during the fourth iteration of the algorithm are highlighted in the last row of FIG. 57. It should be easy to notice that there are 10 open trigrams that are added during this iteration, but only 4 entries are updated in the 3D array. The reason for this is that the new trigrams are obtained by appending the current character to all open bigrams that have already been detected in the sequence so far (all open bigrams, not just the ones added during the fourth iteration). Because their counts are already stored in the matrix, the proper counts for the open trigrams can be calculated by simply adding the 2D matrix to the appropriate 2D slice of the 3D array.

The algorithm does not construct or maintain a list of open bigrams and a list of open trigrams at run time. This FIG. 57 shows these lists only for visualization purposes. If the algorithm were to maintain these lists, then it would no longer have the same nice computational complexity. The algorithm only counts the number of unique open bigrams and open trigrams in these lists. It does that by using the intermediary results as illustrated in this FIG. 57.

Nevertheless, if the list of open trigrams is to be constructed by hand here is a nice way to do this systematically. The first thing that should be noted is that it is very hard to do this given the whole sequence. It is easy to skip some. Thus, just like the encoding algorithm, the enumeration process is iterative. Start with the first character, say it is A. Then list all open bigrams for this sequence. In this case there is just one: AA. Append the current character A to the end of AA and obtain the first open trigram: AAA. Next, the second character is read; it is a B. List all open bigrams in the sequence prefix AB that have been seen up to now: AA, AB, and BB. Append the current character B at the end of each open bigram and get the list of open trigrams: AAB, ABB, and BBB. Next, read the third character, suppose that it is a B again. List all open bigrams that have been seen in the sequence prefix ABB. This list is: AA, AB, BB, AB, BB, and BB. Then append B to get the list of open trigrams that occur in the first three characters of the sequence: AAB, ABB, BBB, ABB, BBB, and BBB. For the remaining character in the sequence the system can continue in the same way. First list all open bigrams that occur in the sequence prefix $S_1, S_2, \ldots, S_i$. Then append the current character $c = S_i$ to the end of all open bigrams to get the set of open trigrams that is added during the i-th iteration. FIG. 57 shows these lists in separate columns. It is worth pointing out that the list of open bigrams can be incrementally updated as well.

In summary, FIG. 57 shows how the open trigram counters are calculated for the sequence S=ABBA. Each row shows a separate iteration as the sequence is scanned from left to right, one character at a time. The last three columns show the contents of the three internal data structures (h, X, and Z) that the system updates during each iteration. The highlighted values in the last row show the entries in the data structures that are updated during the fourth iteration. The lists of open bigrams and open trigrams (third and fourth column) are shown here for visualization purposes only. These lists are not constructed by the algorithm at run time.

As it was mentioned before, a symmetric sequence (i.e., a palindrome) has a symmetric SSM matrix. In certain examples, the matrix may not be uniquely unrollable. For example, the two sequences ABBA and BAAB have the same SSM matrix as shown in FIG. 58. The unrolling algorithm discussed above using open bigrams can output either of these two sequences. When these two sequences are encoded as open trigrams, however, this ambiguity disappears as shown in FIG. 59.

To give just one example why there is no ambiguity, the open trigram ABA occurs two times in the sequence ABBA, but it is completely missing from the sequence BAAB. Because in any sequence there are more open trigrams than open bigrams, a sequence representation based on open trigrams should provide additional information that may improve the accuracy of sequence recognition tasks. This is indeed confirmed by the experimental results that are described later.

In the embodiment discussed above, the number of open trigrams in a single sequence is counted. One possible extension of that embodiment is to count the open trigrams formed by three different sequences. In this embodiment, however, the left character in each open trigram can only come from the first sequence, the middle character from the second sequence, and the right character from the third sequence. This embodiment assumes that all three sequences have the same length.

The computational complexity of this algorithm is $O(TM_F M_S)$, where T is the length of each sequence, $M_F$ is the alphabet size of the first sequence, and $M_S$ is the alphabet size of the second sequence. Notice that the complexity does not depend on $M_R$, which is the size of the alphabet of the third sequence.

To illustrate the output of this embodiment, FIG. 60 shows an example with three different sequences: $S_1$=ABCA, $S_2$=1234, and $S_3$=αβαβ. In keeping with the convention introduced above, three different alphabets are used to emphasize that the three sequences are truly different. For example, they may come from different sensory modalities, and thus it may not be possible to compare characters from different sequences. Fortunately, the algorithm does not have to compare them. It only needs to know which one arrived first and which one arrived second.

FIG. 61 shows another tri-band SSM example that is constructed from the same three sequences, but in this case the order of the first two sequences is swapped. Note that in this case the resulting matrices are different. Thus, the order in which the sequences are presented to the tri-band SSM does matter. Once again, because the alphabet sizes of the three sequences are not the same, the dimensions of the 3D array are all different.

Given three sequences $S_1$, $S_2$, and $S_3$, there are 3×3×3=27 different triples of sequences that can be constructed: $S_1S_1S_1$, $S_1S_1S_2$, $S_1S_1S_3$, $S_1S_2S_1$, $S_1S_2S_2$, $S_1S_2S_3$, ..., $S_3S_3S_2$, and $S_3S_3S_3$. Thus, there are 27 possible 3D arrays of open trigram counters that can be constructed. It is difficult to visualize all of these arrays in one table, but the idea is similar to the one described above for building four dual SSM matrices, one for each possible pair of sequences.

The concept of open bigram can also be generalized to open n-gram in a further embodiment of the present invention. An open n-gram is an ordered n-tuple of characters such that all n characters occur one after another in some sequence S, but they do not have to occur immediately one after another.

In this embodiment the system scans the sequence from left to right, one character at a time and after each new character it performs the following updates. First, it updates the character histogram. Then it uses the histogram to update the open bigram counters. Next, it uses the open bigram counters to update the open trigram counters, which are used to update the open quadgram counters, and so on up to the open n-gram counters. In one embodiment the system writes this general algorithm with nested loops and n-dimensional arrays. However, a preferred embodiment uses a map data structure instead of arrays to store the counters.

The algorithm returns an array Z of n mappings that have a positive counter value for each open k-gram in the sequence S for k=1, . . . , n. The character histogram is stored in the map $Z_1$, which is used to update the open bigram counters in the map $Z_2$, which, in turn, is used to update the counters in the open trigram map $Z_3$, and so on. This iterative process continues until the open n-gram counters in $Z_n$ have been updated.

To perform these updates more effciently, the algorithm uses the idea that an open (k−1)-gram that occurs in the first i characters of the sequence (i.e., in the sequence prefix $S_1$, $S_2$, . . . , $S_i$) will form an open k-gram with the current character $c=S_i$. Thus, by appending c to the end of g it can get a new k-gram γ and update its counter. Because the last character in γ is always the same for all k-grams updated at each iteration, only the counters for the corresponding subset of $Z_k$ have to be updated. The idea of using the counters for (k−1)-grams to update the k-gram counters is quite powerful; without it the algorithm would not be computationally feasible. The complexity of this algorithm is $O(TM^{n-1})$, where T is the length of the sequence, M is the size of the alphabet, and n is the desired n-gram level (e.g., when n=4 the algorithm encodes the sequence in terms of open quadgrams).

Because the n-gram encoding algorithm runs in $O(TM^{n-1})$ time, it is exponential in the alphabet size (which is usually small) and not in the sequence length (which is usually large). Thus, it can be used for real-time applications, especially when the value of n is small.

Matching and smoothing algorithms with open trigrams and open n-grams can also be stated. Because they can be derived by modifying the corresponding algorithms for open bigrams, however, they will not be discussed here.

Embodiments of the present invention discussed so far utilize an SSM representation that used only integers. This was very convenient as it made it possible to describe the theory and the algorithms at an easily accessible level. Also, it did not seem necessary to use anything else as counting open bigrams requires only integers. The integer-based representation, however, has several drawbacks in certain applications. First, there are many aliasing effects, i.e., the mapping from sequences to matrices is not one to one (e.g., ABBA and BAAB). As the sequence length increases these aliasing effects also increase. Second, the integer-based representation makes it possible to encode only discrete sequences that are sampled at regular intervals. In other words, the temporal distance between successive characters must always be an integer. Third, natural phenomena that can be modeled with this representation would not strictly obey these restrictions.

In view of these issues for certain applications, the following will discuss a further embodiment that extends the key ideas from the previous embodiments in several non-trivial ways. First, the histogram accumulation is now done through a function. Before the system simply added one to the histogram element that corresponded to the current character. Now this embodiment can add a real number that is computed by a function, which may depend on time. Second, in the previous models the entries of the histogram vector could only go up. Now this embodiment allows the histogram entries to vary with time, e.g., they can decay exponentially with time. Third, similar rules apply to the matrix. For example, instead of simply adding the histogram vector to the matrix the system can use a function that performs that operation.

FIG. 62 shows an encoding example that uses the exponential update rules. The input sequence in this case is ABAB. All histogram entries decay exponentially with time. In other words, they are divided by 2 at the start of each iteration. Each iteration can be broken down into three steps. First, all histogram bin counters are divided by 2 and stored in the same place. Second, the constant 1 is added to the histogram bin counter that corresponds to the current character. Third, the histogram vector is added to the matrix column that corresponds to the current character. The resulting matrix is no longer an integer matrix.

The notion of a histogram is also no longer nice and clean as the histogram entries decay over time. A different name is probably required for that vector, but this may create more confusion for the reader who is already familiar with the previous notation. Thus, this description will continue to use the term histogram, but it now means a slightly different thing.

This FIG. 62 illustrates the exponential SSM encoding example for the sequence ABAB. As discussed above, during each iteration the entries of the histogram vector are first divided by 2 and then a 1 is added to the bin counter that corresponds to the current character. The entire histogram vector is then added to the matrix column that corresponds to the current character.

FIG. 63 shows the resulting SSM matrices for the sequences ABBA and BAAB when they are encoded with two different algorithms. Using the standard linear algorithm the two matrices are identical. Using the exponential decay algorithm, however, the two matrices are different. This example shows that the only two sequences of length four (given an alphabet of size two) that were confusing before are no longer confusing. In fact, as it turns out, sequences encoded with the exponential decay algorithm are never aliased. In other words, the mapping between sequences and matrices is one to one.

FIG. 64 gives another example with the exponential decay encoding algorithm of this embodiment of the present invention. The input sequence in this case is ACBAB. It has three unique characters, and thus the resulting matrix is of size 3×3. Once again, during each iteration the elements of the histogram vector are first divided by 2 and then a constant, which is equal to 1 in this case, is added to the element that corresponds to the current character that is read at the current iteration. The entire histogram vector is then added to the matrix column that corresponds to the current character.

In all previous SSM model embodiments only one element of the histogram vector was updated during each iteration. In the exponential SSM model embodiment they all decay over time. So all of them are changed at each iteration. This is why all histogram elements are highlighted in this FIG. 64.

That is, this FIG. 64 provides an illustration of the encoding algorithm with exponential decay. The input sequence in this example is ACBAB. Notice that during the fifth iteration there are five new open bigrams that must be counted (highlighted). Only three elements of the matrix, however, are changed during that iteration. Thus, the histogram vector implicitly counts all new open bigram instances.

FIG. 65 shows an unrolling example using the matrix for the sequence ABAB. In this case the unrolling is done in reverse so the resulting sequence is BABA. The unrolling rules are similar to the encoding rules, but the process is done in reverse. During each iteration the system attempts to subtract the histogram vector from one of the columns of the matrix. The subtraction is subject to the constraint that none of the matrix elements can become negative. This imposes a constraint on which columns are eligible for subtraction during each iteration. This, in turn, imposes an order in which the sequence can be unrolled.

After the histogram vector is subtracted the system subtracts 1 from the bin that corresponds to the current character. The elements of the entire histogram vector are then multiplied by two. This process is repeated during the following iterations. In other words, the order of the operations for unrolling in reverse is the following. First, find a column from which the vector h can be subtracted without any of the matrix elements becoming negative. Second, subtract the vector h from that column and unroll the character that corresponds to it. Third, subtract one from the element of h that corresponds to the character that was just unrolled. Fourth, multiply all entries of the histogram vector h by 2. Fifth, if all elements of the histogram vector h are zero, then exit; otherwise go to the first step.

As just discussed, FIG. 65 provides an example of unrolling the sequence ABAB in reverse, i.e., it is unrolled as BABA, by repeatedly subtracting the encoding histogram vector h from one of the matrix columns without any of the matrix elements becoming negative. After the last iteration the matrix contains only zeros.

This procedure works for unrolling in reverse. If the system attempts to unroll the sequence going forward, however, it reaches the situation shown in FIG. 66. That is, if the system attempts to use the encoding histogram vector h for forward unrolling, then it gets stuck as that vector cannot be subtracted from any row of the matrix without any of the matrix elements becoming negative.

The way out of this is to realize that the system needs two histogram vectors. The first one, h, is constructed and used during encoding. The second one, h*, is also constructed during encoding (but using a different procedure) and it is used for unrolling. FIG. 67 shows a forward unrolling example using the matrix for the sequence ABAB. Using the second histogram vector h*, the unrolling is now fully deterministic. The elements of h* are updated during forward unrolling similar to the way the elements of h are updated during unrolling in reverse.

The second histogram vector, h*, is constructed during encoding as follows. First, all elements of h* are multiplied by 2. Second, add 1 to the entry of h* that corresponds to the current character. Third, at the end of the encoding normalize all values of h* by dividing them by $2^{T-1}$.

The following gives another unrolling example with a 3×3 matrix. The sequence from which this matrix was constructed is ACBAB. FIG. 68 shows the forward unrolling process, which is fully deterministic. The only thing that is worth mentioning again is that the unrolling histogram h* is different from the encoding histogram h. In this example of unrolling the sequence ACBAB from its exponential SSM matrix, the system repeatedly subtracts the histogram vector h* from one of the rows of the matrix without any matrix elements becoming negative. At the end of this process the matrix contains only zeros.

FIG. 69 shows that the unrolling process gets stuck immediately if the encoding histogram h is used for unrolling. That is, this FIG. 69 shows that if the system attempts to use the encoding histogram vector h for forward unrolling, then the process gets stuck. The matrix in this case is the same as the one shown in FIG. 68, i.e., it corresponds to the sequence ACBAB.

FIG. 70 shows the process for unrolling in reverse. That is, it shows an example of unrolling the sequence ACBAB in reverse by repeatedly subtracting the histogram vector h from one of the matrix columns without any of the matrix elements becoming negative. In other words, the sequence is unrolled as BABCA. Notice that the histogram vector that is used for unrolling in reverse is different from the one used for forward unrolling.

Finally, it is worth mentioning that there are other coupling functions that can be used. So far the description has only given examples with "multiply by 2" and "divide by 2." In the general case, however, there is a whole class of functions that can be used with similar results. Here is one of them:

$$f(t) = A \cdot \exp\left(-\frac{t}{\tau}\right) \tag{16}$$

where A is a constant, $\tau$ is also a constant that controls the decay rate, and t is the time at which the character arrives. The sequences described so far were discrete. Thus, the value of t can only be an integer, e.g., 0, 1, . . . , T−1. A much more general embodiment that, among other things, eliminates this restriction is described hereinbelow.

Figures 71, 72:
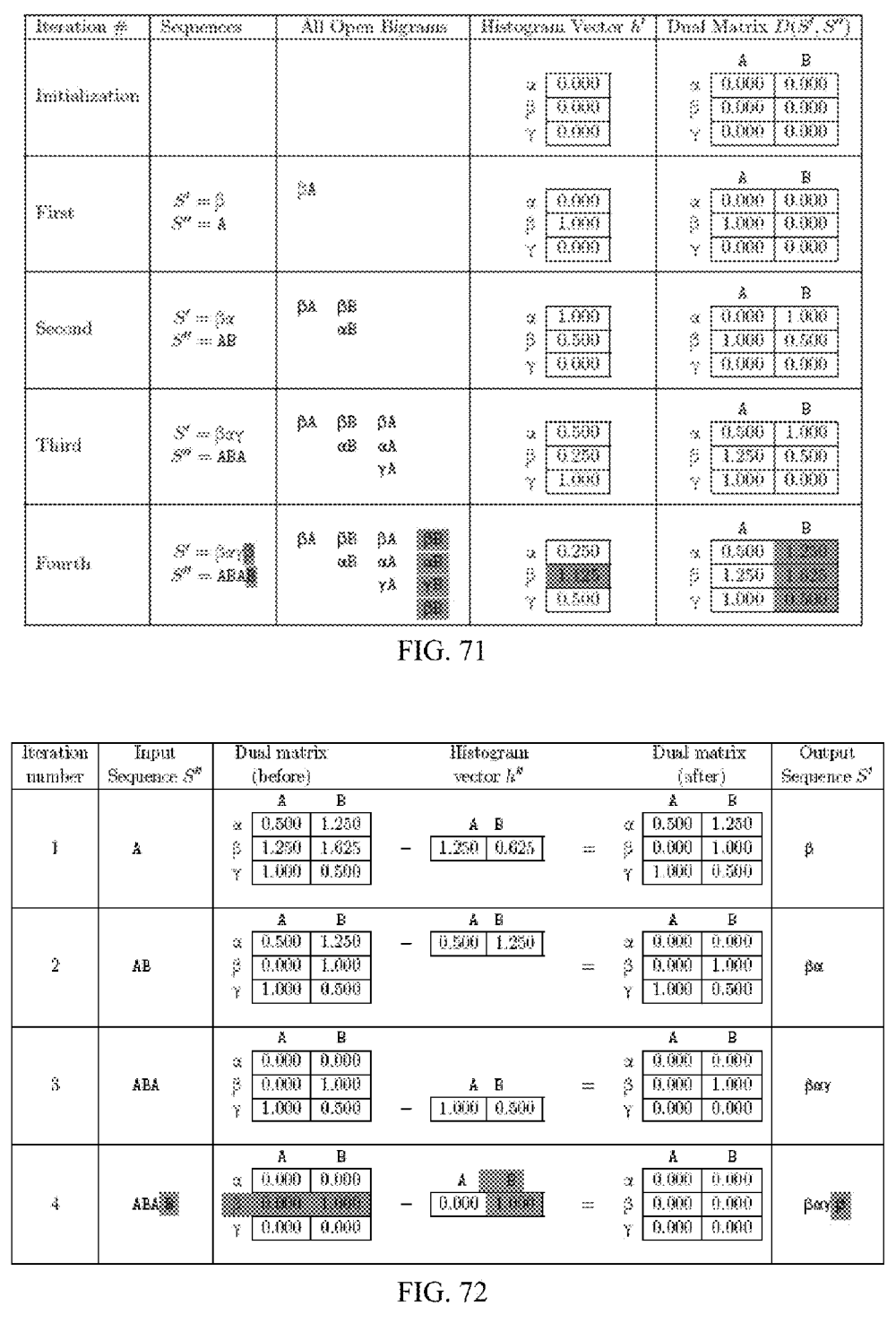

FIG. 71 illustrates the dual encoding process with exponential decay. The two input sequences are S'=βαγβ and S"=ABAB. The histogram vector h' for the first sequence is used for encoding. The encoding procedure uses the following steps. First, divide all entries of h' by 2. Second, add 1 to the element of h' that corresponds to the current character in S'. Third, add the vector h' to the column of the dual matrix that corresponds to the current character in S".

Having illustrated in FIG. 71 an example of the dual encoding with exponential decay, FIG. 72 illustrates an example of forward unrolling of a dual exponential matrix. The two sequences from which the matrix was encoded are the same as above. The dual matrix is denoted by D(S', S"). Given the sequence S" this example shows how to unroll the sequence S'. The dual model consists of the dual matrix D(S', S") and the histogram h" for the second sequence.

Figure 73:
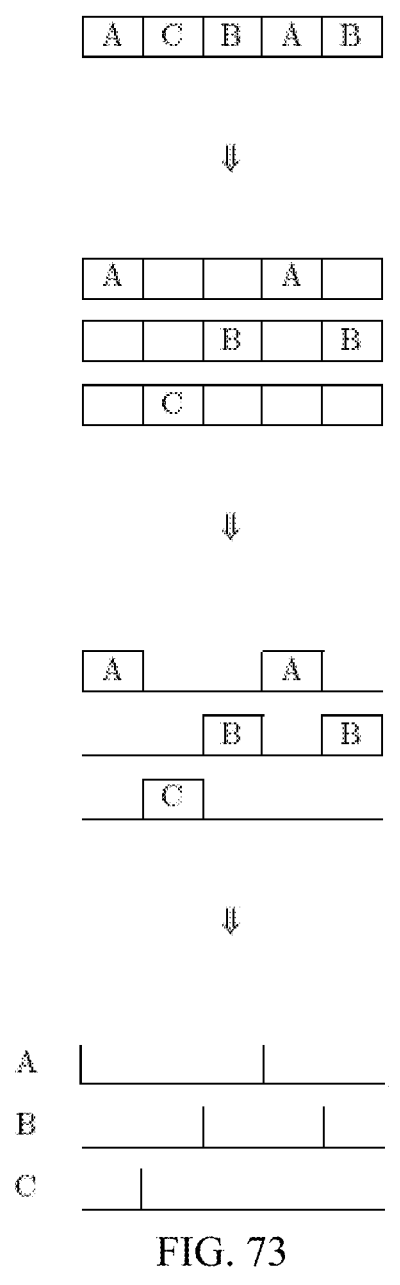

While the examples discussed above utilize discrete sequences, it was suggested that a spike-based encoding could be used in other embodiments. Indeed, FIG. 73 shows how to convert a discrete sequence into a spike-based encoding. Converting a discrete sequence into a spike-based representation requires that the characters of the sequence be placed one per box. During the second step the sequence is split into three sequences, each containing instances of only a single letter. Stage three is the same as stage two, but now the empty boxes have been removed. Finally, the conversion to spikes is achieved by keeping only the left edge of each box.

Figure 74:
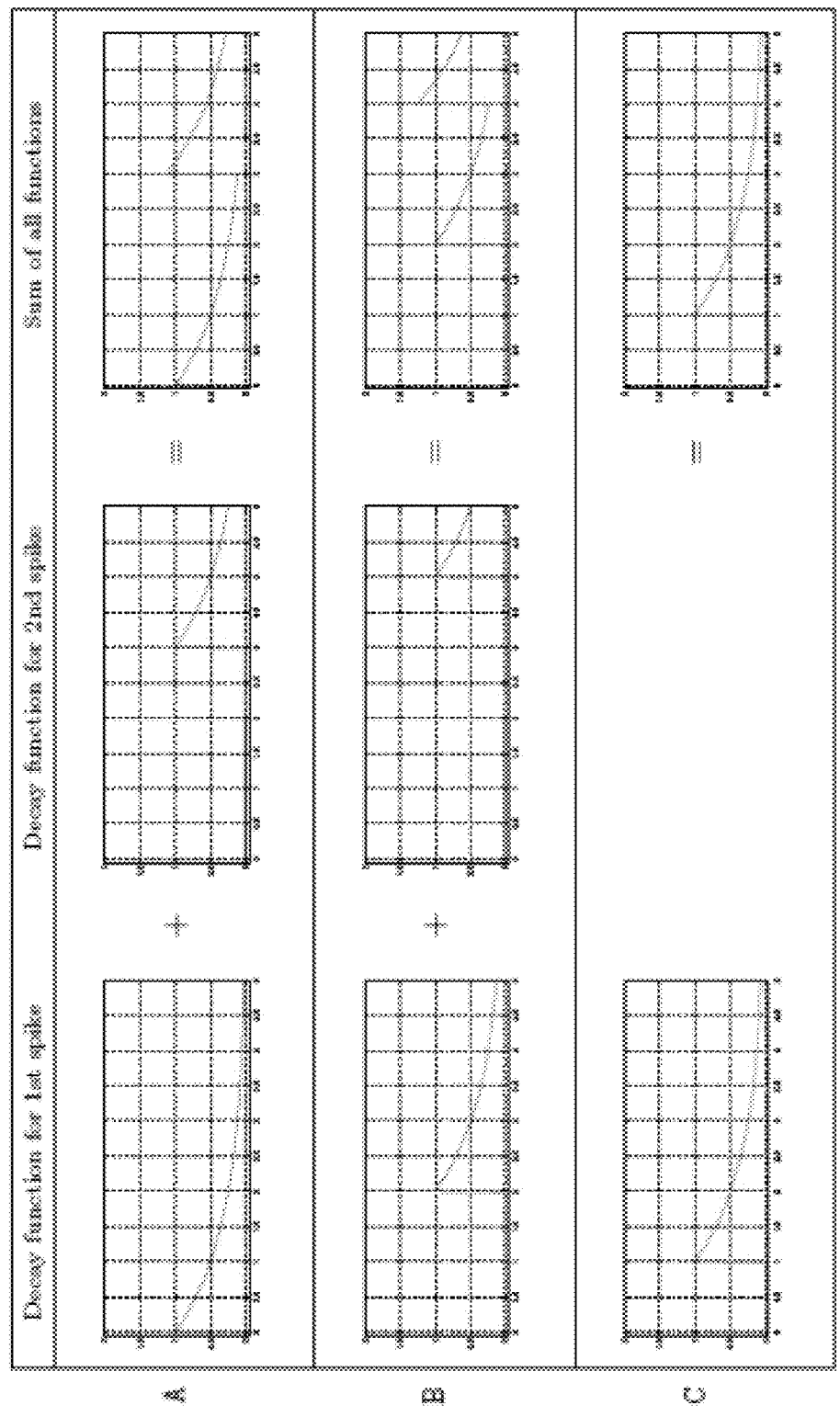
FIG. 74 is a graphical flow diagram illustrating the spike-based encoding for an exemplary sequence in accordance with an embodiment of the present invention.

FIG. 74 shows another way to look at this type of encoding. Each spike creates a bump in the signal, which then decays exponentially over time. A second spike on the same line creates a second bump. The decay functions on each channel are added together as shown in the third column of the figure. The last line, which corresponds to the character C has only one spike. In this example the inter-spike distance is always the same (and always an integer number). So this encoding example looks a lot like the one for the same sequence that was given in the exponential SSM section above. The values of the histogram vector during each encoding iteration are equal to the values of the coupling function at the times when the spikes occur. As may be seen, FIG. 74 illustrates the spike-based encoding for the sequence ACBAB. The horizontal axis in each plot is time. It should be noted that while these plots illustrate the occurrence of the spikes at discrete times, the SSM can utilize continuous time variation as well, i.e. the spike can occur at any time. For example, the coupling function $2^{(t0-t1)}$, where $t_0$ and $t_1$ are the times at which the two spikes occurred. In such a situation, the slicing or sampling occurs when the second spike occurs, and the value is that of the decay function of the first. The vertical axis in these plots is intensity. In this example there are 5 spikes.

As introduced above, embodiments of the present invention can process their algorithms even faster since they are really easy to run in parallel. Implementation on a GPU (Graphical Processing Unit) instead of CPU is also possible in various embodiments.

If the SSM matrix needs to be computed for a very long string, then the communication between different processes is limited to sending the chunk of the string and receiving the SSM matrix and the vector of character counters for this chunk. Each processor runs a version of the encoding algorithm that requires $O(TMP^{-1})$ operations, where T is the length of the sequence, M is the size of the alphabet, and P is the number of processors.

FIG. 75 illustrates spike-based sequences for demonstrating dual SSM encoding with exponential decay in accordance with one embodiment of the present invention. In this case the spikes are not derived from discrete sequences, i.e., the spikes do not occur at integer or even regular intervals. The first two rows ($\alpha$, $\beta$) in this FIG. 75 correspond to the first spike-based sequence S'. The bottom three rows (A, B, C) of this FIG. 75 correspond to the second spike-based sequence S". In other words, the sequence S' has two channels $\alpha$ and $\beta$. The spike-based sequence S" has three channels A, B, and C. The goal is to encode an exponential dual SSM matrix from the channels of these two spike-based sequences.

In this embodiment the approach is generalized to dual encoding and the restriction on the timing of the spikes in different channels is dropped. FIG. 75 shows an example of the dual spike-based encoding that uses the coupling function $2^{t0-t1}$, where $t_0$ and $t_1$ are the times at which the spikes occurred. In other words, in this embodiment the coupling function uses exponential decay.

Figure 76:
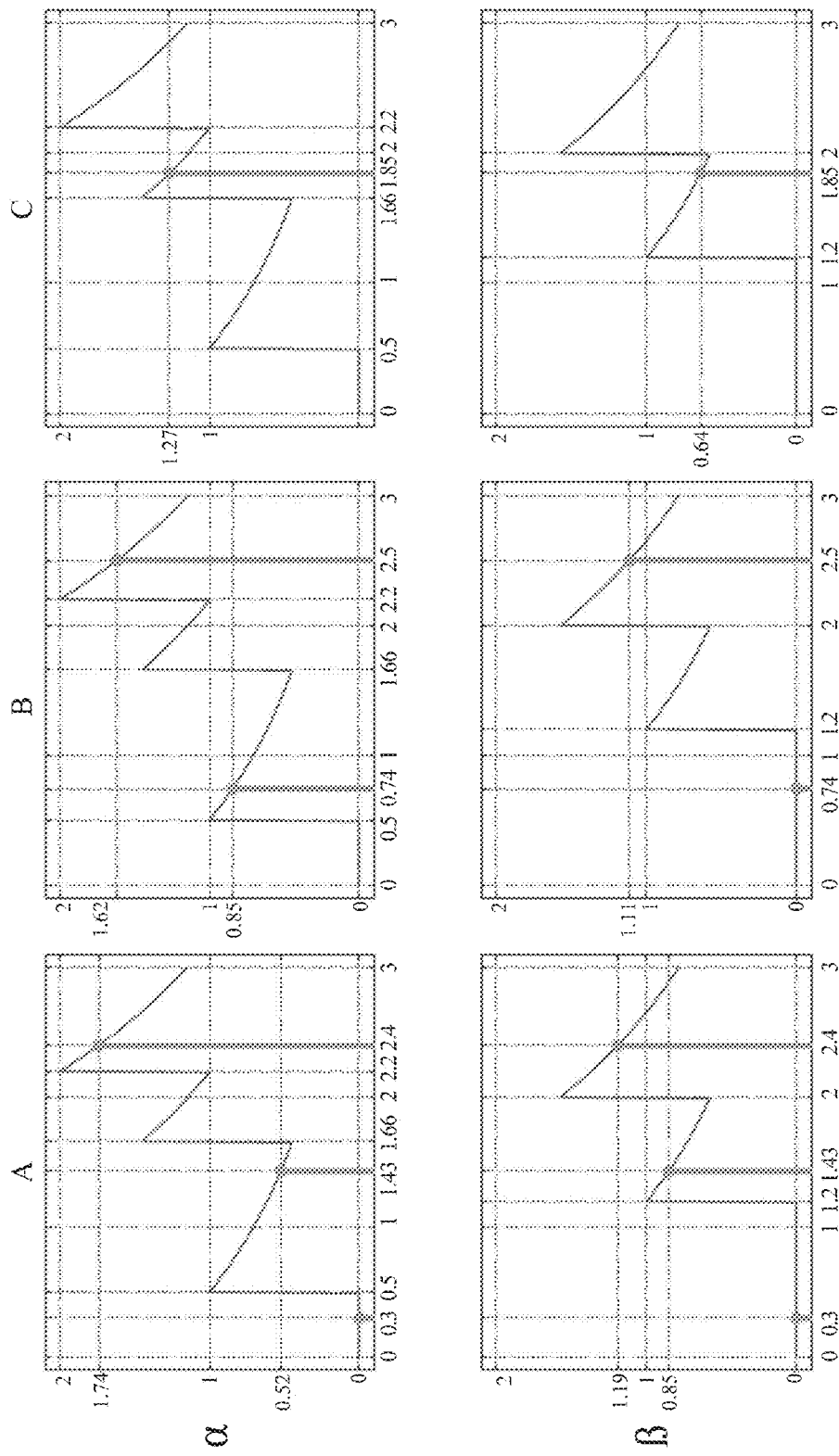
FIG. 76 is a graphical flow diagram illustrating the dual SSM encoding with exponential decay for the spike-based sequences of FIG. 75.

FIG. 76 shows that an approach that is similar to the one that was used for single exponential SSM encoding works for the dual exponential embodiment as well. In this FIG. 76, the function plotted in each of the three plots in the top row traces the value of the first element of the exponentially decaying histogram vector h', which corresponds to the a channel of S'. The function plotted in each of the three plots in the bottom row traces the value of the second element of the histogram vector h', which corresponds to the $\beta$ channel of S'. The vertical lines in the upper-left image correspond to the spikes on the A channel of S". The intersections between these spikes and the histogram curve are indicated with dots. The Y-coordinates of these dots are equal to the values of the histogram curve at the times when the spikes occurred. In other words, each spike of sequence S" samples the value of the histogram curve. The sampled value is added to the corresponding element of the dual SSM matrix. The remaining five plots show similar information for the remaining five combinations of the $\alpha$ and $\beta$ channels of the first spike-based sequence S', and the A, B and C channels of the second spike-based sequence S".

As may be seen from this FIG. 76, a spike on one of the input channels in S' creates a bump in the corresponding bin value of the histogram h'. A spike on one of the channels in S", on the other hand, samples the value of the histogram h' and adds it to the corresponding column of the dual SSM matrix.

Figure 77:
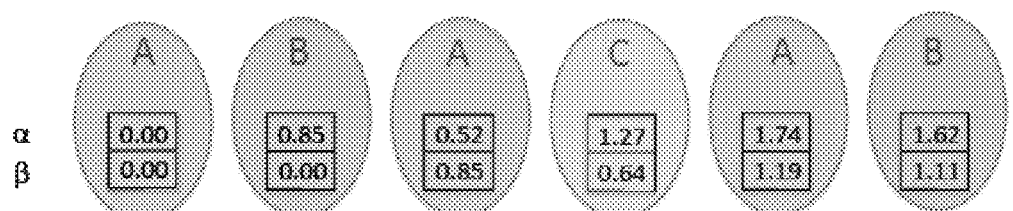
FIG. 77 illustrates sampled values of the exponentially decaying histogram vector h' at times when a spike occurred on any of the channels of the second spike-based sequences of FIG. 76.

FIG. 77 shows the sampled histogram values. Specifically, FIG. 77 shows the sampled values of the exponentially decaying histogram vector h' at the times when a spike occurred on any of the channels of the second spike-based sequence S" as shown in FIG. 76. Because the first spike-based sequence S' has two channels ($\alpha$ and $\beta$), the value of the exponentially decaying histogram vector h' can be represented with a column vector of size 2. Each of the sampled column vectors is labeled with the name of channel from S" on which the spike occurred when the value of h' was sampled.

Figure 78:
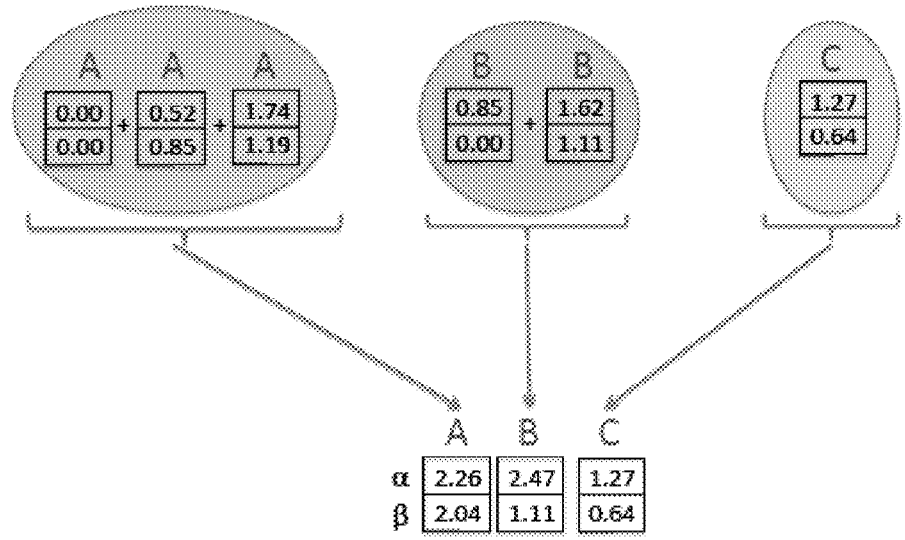
FIG. 78 illustrates grouping of the sampled column vectors from h' of FIG. 77 based on their labels from the channels of the second sequence of FIG. 75.

FIG. 78 shows how the values of h' can be added to the corresponding columns of the SSM matrix. Specifically, this FIG. 78 shows the same sampled column vectors from h' as in FIG. 77, but in this case they are grouped based on their labels from the channels of S". All vectors in the same group are added to the same column of the dual SSM matrix. In other words, the dual SSM matrix is computed by adding each sampled value of h' to the corresponding column of the dual SSM matrix where the column is selected by the channel of S" on which the spike that sampled this value of h' occurred.

Having discussed the various embodiments of the SSM matrix algorithms, attention is now turned to an embodiment of the present invention that uses SSMs for speech recognition. While such embodiment providing speech recognition is particularly advantageous, other embodiments of the present invention can be applied to many other domains, and the following should be taken by way of example and not by way of limitation. The following examples use sample words from the TIMIT corpus.

Figure 79:
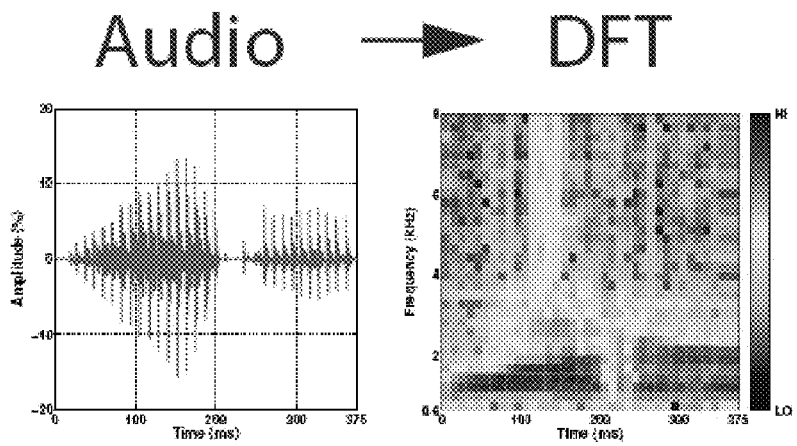
FIG. 79 is a graphical transformation illustration showing a raw audio signal and its associated Discere Fourier Transform (DFT)
Figure 80:
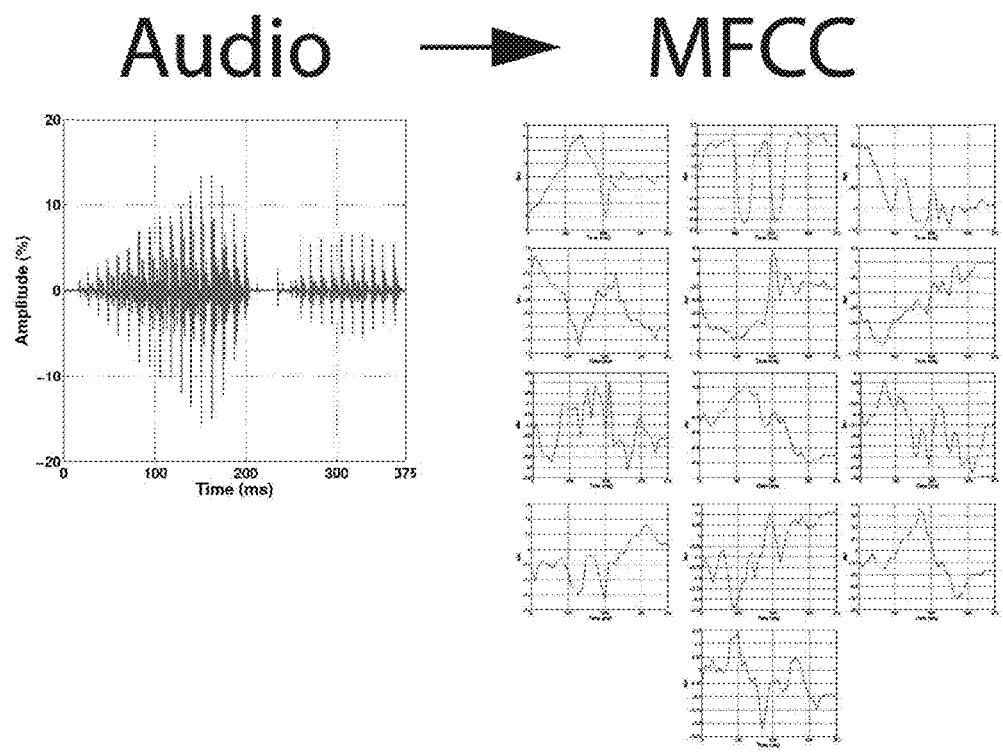
FIG. 80 is a graphical transformation illustration showing a raw audio signal and its associated 12 Mel Frequency Cepstrum Coefficients.

When working with audio signals one typically applies the Discrete Fourier Transform (DFT) to the raw audio signal as shown in FIG. 79. The colors of the histogram correspond to the energy of the signal in each frequency band. This representation, however, is not very optimal for working with speech signals. However, the raw audio signal can also be represented in terms of the 12 Mel Frequency Cepstrum Coefficients and the normalized energy parameter. This is a standard part of the first stage of the auditory pipeline for speech recognition and is shown in FIG. 80.

Figure 81:
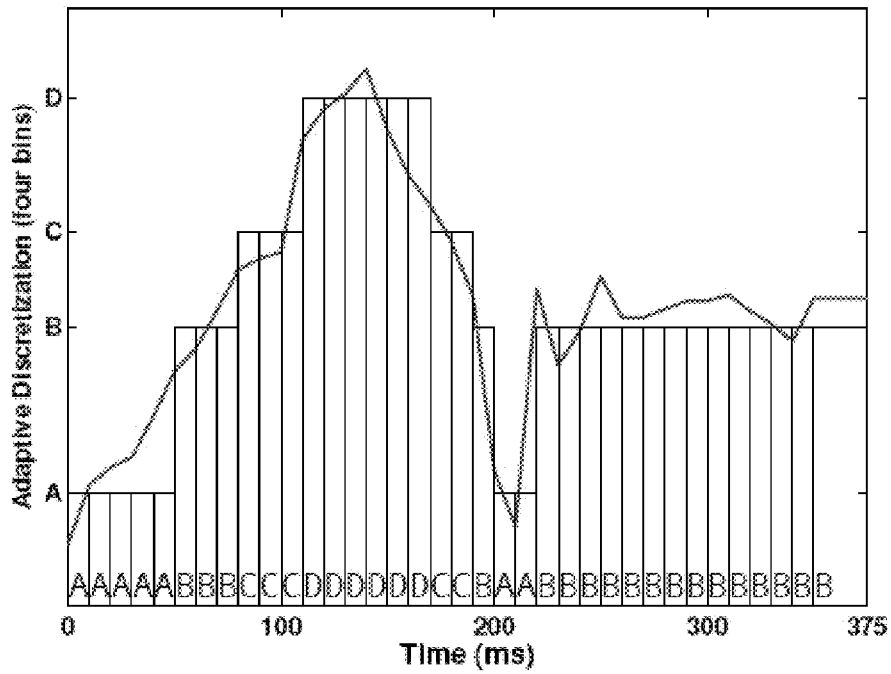
FIG. 81 is a graphical illustration of the adaptive discretization for a normalized energy parameter of the raw audio signal of FIG. 100 in accordance with an embodiment of the present invention.

In this embodiment, adaptive discretization for the normalized energy parameter is used. The four discretization levels are mapped to the characters: A, B, C, and D. The signal is then converted into a discrete sequence as shown in FIG. 81.

Figure 82:
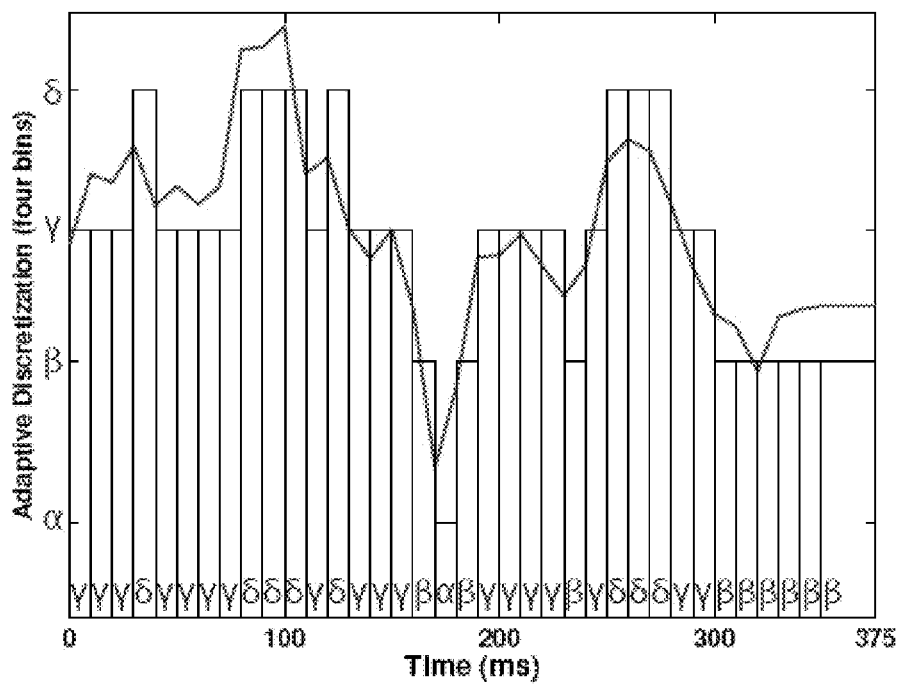
FIG. 82 is a graphical illustration of the adaptive discretization for one of the Mel Frequency Sepstrum Coefficients of the raw audio signal of FIG. 100 in accordance with an embodiment of the present invention.

In FIG. 82, the adaptive discretization for the Mel Frequency Spectrum Coefficient number 12 is illustrated. Notice that in this case the resulting alphabet is different from the one used in FIG. 81 as the two plots have different units along their vertical axes.

Figure 83:
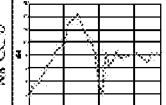
FIG. 83 is a tabular flow diagram of the adaptive discretization, sequencing, and SSM matrix encoding for each of the Mel Frequency Sepstrum Coefficients of the raw audio signal of a spoken word in accordance with an embodiment of the present invention.

With this principle in mind, the pipeline used for encoding an audio signal into SSMs is shown in FIG. 83. The raw audio signal is converted into the Mel Frequency Cepstrum Coefficients. Each of these 13 is then discretized using an adaptive discretization. Each one has a different alphabet as they have different units on the y axis and putting them into the same alphabet would be like trying to add apples with oranges. Finally, each sequence is encoded into an SSM. The 13 SSM matrices collectively represent the encoding for this word. The word "water" is spoken by the speaker having the speaker identification MMAG0 from TIMIT.

Figure 84:
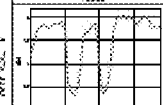
FIG. 84 is a tabular flow diagram of the adaptive discretization, sequencing, and SSM matrix encoding for each of the Mel Frequency Sepstrum Coefficients of the raw audio signal of a spoken word in accordance with an embodiment of the present invention.
Figures 85, 86:
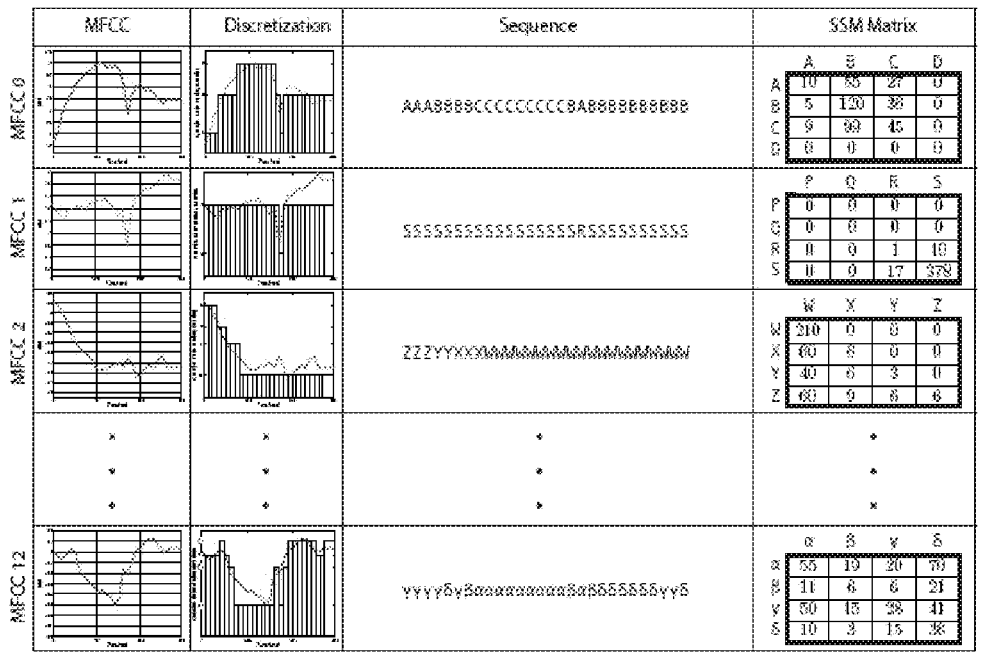
FIG. 85 is a tabular flow diagram of the adaptive discretization, sequencing, and SSM matrix encoding for each of the Mel Frequency Sepstrum Coefficients of the raw audio signal of a spoken word in accordance with an embodiment of the present invention.
FIG. 86 is a graphical illustration of computed distance measurements between two utterances of different words spoken by the same speaker in accordance with an embodiment of the present invention.

This encoding can be done for each word and speaker. For example, FIG. 84 is for a different word spoken by the same speaker (year_MMAG0 in TIMIT notation). Similarly, FIG. 85 shows the encoding for the same word (water) spoken by a different speaker (water_FFSB0 in TIMIT notation).

In order to determine the correct word spoken, the distance between the utterance and the model is computed. For example, FIG. 86 illustrates the computed distance between two utterances of different words spoken by the same speaker (water_MMAG0 and year_MMAG0). The distance metric in this example is the smoothed symmetric D-KL metric. FIG. 87 illustrates this distance calculation for two different utterances of the word water spoken by a male and a female speaker (water_MMAG0 and water_FFSB0).

Matching the word water to the closest words in a database of words spoken by 4 different speakers is illustrated in FIG. 88. The three closest matches are indicated with X marks.

Figure 89:
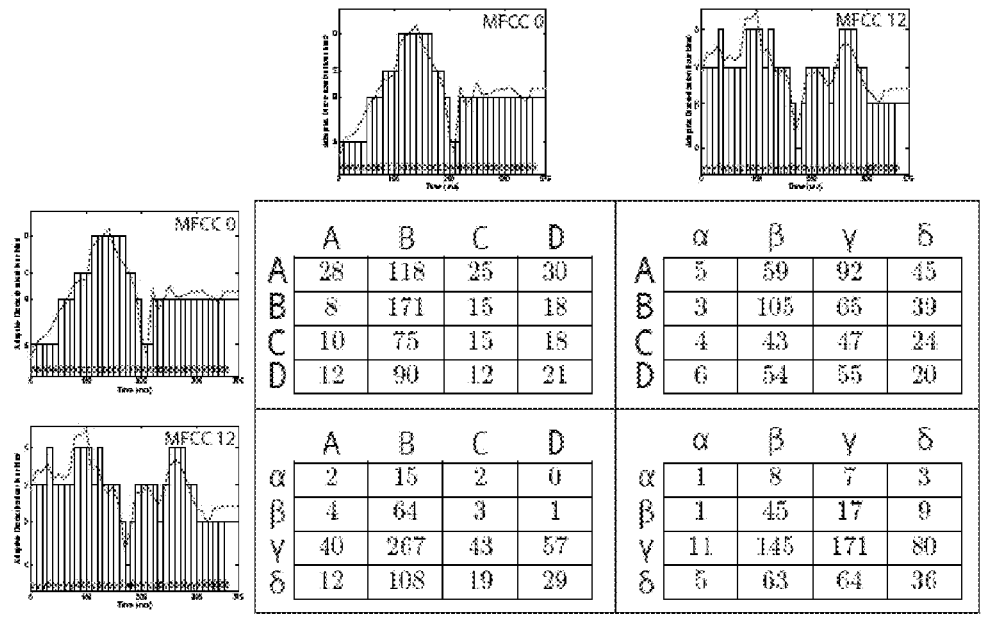
FIG. 89 is a graphical illustration of dual SSM matrices constructed for all 4 possible combinations of mel0 and mel12 for the word WATER spoken by speaker MMAG0 in the TIMIT dataset in accordance with an embodiment of the present invention.

As discussed, each audio sample can be represented with 13 MFCC curves over time. While these curves are derived from the same signal they can capture different aspects of it, and thus they can be fed to an embodiment of the present invention that utilizes a dual SSM model. FIG. 89 shows MFCC 0 and MFCC 12 for the word water again. These are discretized using adaptive discretization. The four possible combinations of these two sequences are fed to dual SSMs, resulting in four matrices. That is, the dual SSM matrices are constructed for all 4 possible combinations of mel0 and mel12 for the word WATER spoken by speaker MMAG0 in the TIMIT dataset.

Figure 90:
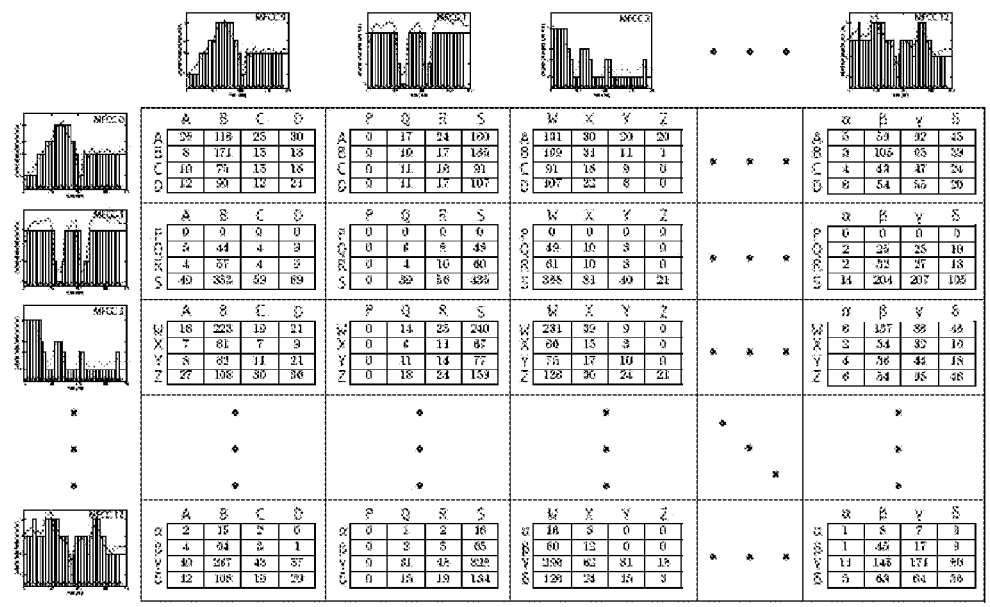
FIG. 90 is a graphical illustration of the dual SSM matrices resulting from encoding each of the 13 MFCCs against all other ones for the word WATER spoken by speaker MMAG0 in accordance with an embodiment of the present invention.
Figure 91:
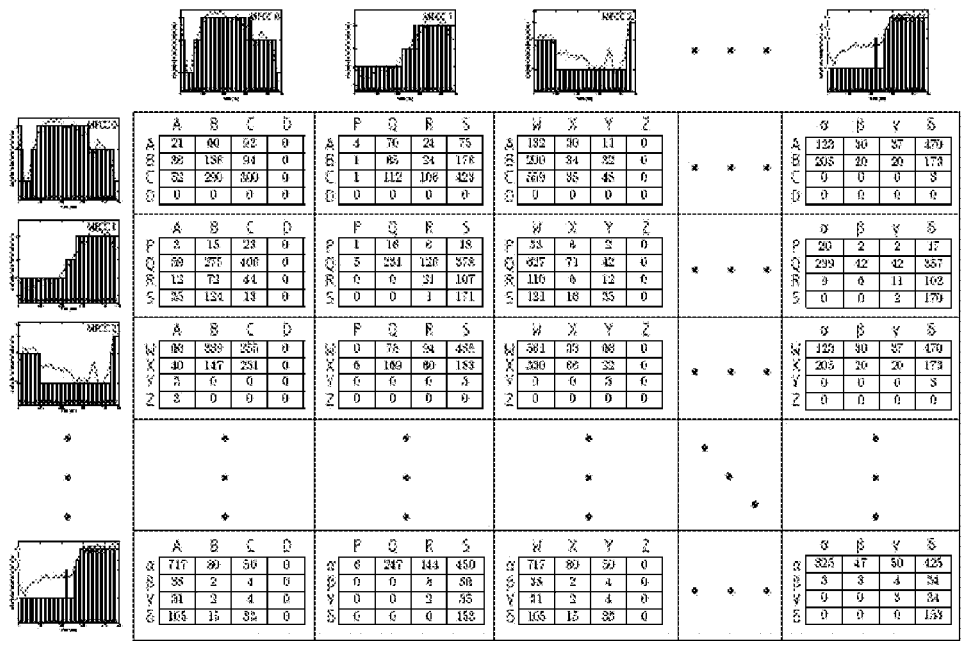
FIG. 91 is a graphical illustration of the dual SSM matrices resulting from encoding each of the 13 MFCCs against all other ones for the word YEAR spoken by speaker MMAG0 in accordance with an embodiment of the present invention.
Figure 92:
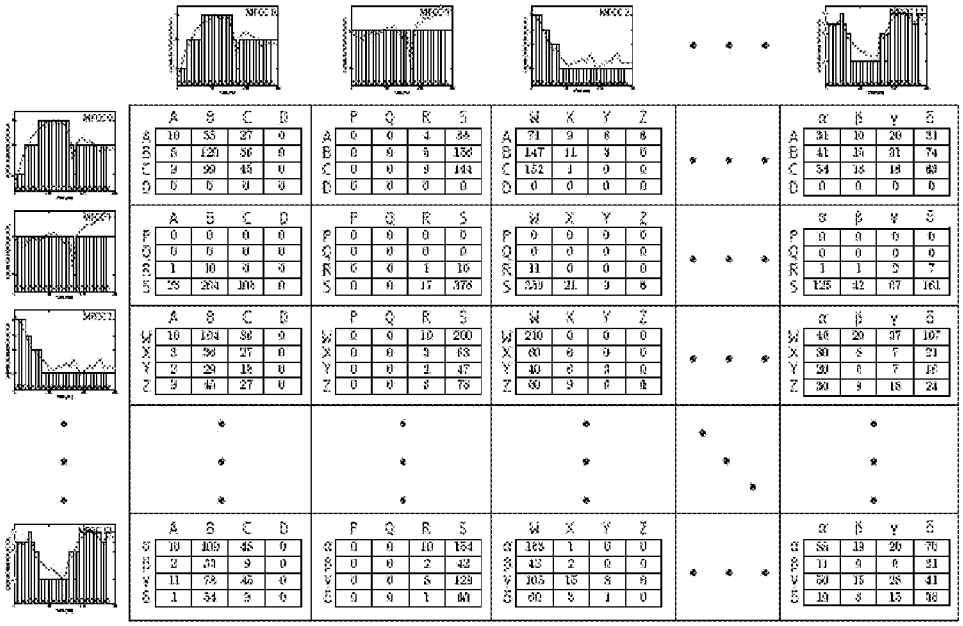
FIG. 92 is a graphical illustration of the dual SSM matrices resulting from encoding each of the 13 MFCCs against all other ones for the word WATER spoken by speaker FSSB0 in accordance with an embodiment of the present invention.

Because there are 13 MFCCs, the sequence for each of them can be encoded against all other ones, resulting in 13×13=169 different SSM matrices. FIG. 90 shows the 169 matrices. While FIG. 90 shows a representation for the word "water," FIG. 91 shows the same representation, but for the word "year" spoken by the same speaker. Finally, FIG. 92 shows this representation for another utterance of "water," but this one is spoken by a female speaker (FSSB0).

As before, the system of this embodiment can calculate the distance between two speech signals in terms of the resulting SSM matrices by using the $d_{KL}^{(symm)}$ metric or any other distance metric. In this case, however, there are 169 dual matrices and distances can be calculated between each pair of corresponding matrices built for two utterances.

To do word recognition the system can find the distance between the test word and all other training words stored in the database. FIG. 93 shows an example of this process with 4 different speakers and different words illustrating the results for four speakers with the dual SSM. The testing word utterance is WATER spoken by Speaker 1. The closest 3 matches, which are indicated with X marks, are for WATER spoken by Speaker 3, WATER spoken by Speaker 4, and WASH spoken by Speaker 1. In one embodiment, the system of the present invention utilizes a voting mechanism to recognize the test word. Thus, the testing word in this example is correctly recognized as WATER. Note that WATER spoken by Speaker 1 is at distance 0, but that is the testing utterance and it is not part of the training database in this example.

Beyond these examples, the TI-DIGITS Speech Corpus is used to ensure accurate recognition by using the test utterances of 326 speakers (111 Men, 114 Women, 50 boys, 51 girls), each speaking 77 digit sequences, however 6 were removed due to speaker errors. This results in 326*77−6=25,096 total utterances. Another way to look at this is 326 speakers, each spoke 11 digits, two times each. The 11 digits were: 1, 2, 3, 4, 5, 6, 7, 8, 9, 0, Oh, which resulted in 326*11*2=7,172 utterances. In describing the TI-DIGITS Speech Corpus, it is noted that the transcriptions made by the listeners differed for only 136 utterances: 30 because of speaker errors; the remaining 106 because of listener errors. This was used to set an acceptable error rate for machine speech recognition, i.e. 0.4 percent (106 errors out of 25,102 utterances). Building a recognizer that would identify spoken isolated digits with that same low error rate was the ultimate challenge set by the TI-DIGITS corpus. It has been reported that the best working system was developed at AT&T and based on a segmental characterization of the digits, and achieved digit error rates on the order of 0.2%.

With these goals in mind, a test of an embodiment of the present invention was conducted on the single digits section of TI-DIGITS using these parameters. The results were 99.84% correct for all adult speakers (56 men and 57 women), based on only 4 errors out of 2,486 utterances. For all 50 children's utterances, the system achieved a 98.82% success rate, or only 13 errors out of 1,100 utterances. For all speakers (113 adults and 50 children), the embodiment of the system of the present invention achieved 99.27% success rate, having only 26 errors out of 3,586 utterances. In comparison to the results of the embodiment of the present invention just discussed, the Google speech API achieved a 93.52% success rate for adult speakers, an 80.18% success rate for children speakers, and an overall success rate of 89.43%.

In another embodiment of the present invention, an SSM representation for the DNA sequence GATTACA is accomplished. Thus, the SSM sequence model can be used to analyze biological sequences. As shown in FIG. 94, this encoding is done at the level of base pairs (the letters A, T, G, and C). As shown below, it is also possible to use an encoding over the set of amino acids.

In molecular biology there are problems where the goal is to predict a property of a biological molecule or a part of a biological molecule. Examples of these problems include predicting the location of a protein within a cell, e.g., subcellular protein localization, predicting the structural class of a protein: α, β, α+β, or α/β, predicting the functional family of an enzyme: oxidoreductase, transferase, hydrolase, lyase, isomerase, or ligase (each family may have sub-families, which can also be predicted), predicting the location of a protein within the nucleus of a cell, e.g., subnuclear protein localization, predicting the location of a protein within mitochondria, e.g., submitochondria protein localization, detecting papillomaviruses that can infect humans and may cause cancer, detecting proteins that may bind to DNA, participating in gene regulation, etc. This list is by no means complete as new problems arise as more genetic sequences become available.

Approaches to solving these problems often use sequences of nucleic or amino acids that encode molecules or parts of a molecule to infer the needed property. Standard machine learning techniques are applied to numeric features extracted from these sequences. These learning pipelines can be viewed as two stage processes: 1) converting the sequences, and, in some cases, other information about molecules or regions within molecules into numeric feature vectors, and 2) applying standard machine learning algorithms to build models that can infer properties of molecules or regions within molecules from their feature vectors.

For these approaches, the SSM representation can be used without fully redesigning the pipeline, i.e., as a "plug-in" into existing pipelines. SSM features can replace or extend numerical feature vectors extracted from genetic sequences. Existing feature vector designs often include amino acid histograms, regular n-gram counters, and other numerical characteristics that describe local features of sequences. SSM features can be used to capture local and global features of sequences. Dual-band and multi-band SSM representations can be used to combine different types of information about sequences in a single coherent framework, potentially allowing the building of increasingly powerful models using the SSM framework.

The following describes how the SSM can be utilized by plugging it into an existing learning pipeline for subcellular protein localization. In particular, instead of using regular n-grams, the SSM uses open bigram counters, which leads to improvement in learning performance. In other words, comparing the performance of the same machine learning algorithm applied to regular n-grams and open bigrams reveals the potential benefits of using the SSM for analyzing biological sequences.

The "plug-in" approach that incorporates SSM into an existing machine learning pipeline for subcellular protein localization was reduced to practice for the pipeline described in the academic paper entitled "Protein sequence classification using feature hashing" by C. Caragea, A. Silvescu, and P. Mitra, the teachings and disclosure of which are incorporated herein in their entireties by reference thereto. The paper describes an approach that uses numeric features obtained by counting regular n-grams in protein sequences (in their experiments n varied between 1 and 5). Because the number of possible n-grams grows exponentially as n increases, the paper proposes a method for reducing the dimensionality of the feature vector by merging some n-grams using a hash function that may produce the same value for different n-grams. This value gives the index of an element in the feature vector. Despite these efforts, the number of regular n-gram counters that need to be used to achieve a desired level of performance for subcellular protein localization may be quite high.

The "plug-in" approach was reduced to practice in four steps: 1) obtaining the same open source library LIBLINEAR that implements the standard machine learning algorithm based on linear support vector machine (linear SVM) described in that paper, 2) obtaining the public datasets that contain protein sequences for the benchmarks described in that paper, 3) plugging SSM into the pipeline by replacing the feature extraction step that uses regular n-grams with SSM features that use open n-grams (using open bigrams was sufficient to match and exceed the top performance levels described in the paper), and 4) evaluating the performance of the extended pipeline using the same cross-validation technique and performance metrics that were used in that paper. Because the benchmark datasets, the evaluation procedure, and the evaluation metrics are the same, the results can be directly compared to those of the paper, and positive conclusions about the utility of the SSM for subcellular protein localization problem can be made.

An example record from one of the datasets used to reduce the SSM to practice for subcellular protein localization problem is shown in FIG. 95, wherein: (a) the amino acid sequence of the example protein in FASTA format; (b) the name of the example protein; (c) the class of the example protein (this is the property that the machine learning pipeline learns to predict). The standard mapping from letter codes to amino acids used in the FASTA format for representing nucleotide and protein sequences in plain text is shown in FIG. 96.

The high level structure for existing pipelines for subcellular protein localization is shown in FIG. 97, and the SSM pipeline for subcellular protein localization is shown in FIG. 98. Utilizing this embodiment, the SSM representation for the example protein shown in FIG. 95 is illustrated in FIG. 99 at (a). The SSM matrix was computed using a sliding window of size 51, the first character in an open bigram corresponds to a row, the second character corresponds to a column in the matrix. Shown at (b) in FIG. 99 is the histogram of amino acid occurrences in the example protein.

Figures 100, 103, 104:
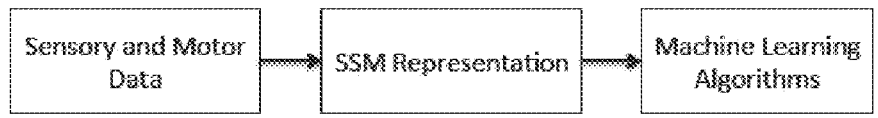
FIG. 100 is tabular illustration of a matrix of regular bigrams for the example protein shown in FIG. 95.
FIG. 103 is a schematic illustration of a data processing pipeline for interactive object recognition in accordance with an embodiment of the present invention.
FIG. 104 is a tabular illustration of the performance of the learning pipeline for interactive object recognition of FIG. 103 measured in percentage of correctly recognized objects for individual behavior/modality combinations and for combinations of the two sensory modalities.

FIG. 100 illustrates a matrix of regular bigram counters for the example protein shown in FIG. 95. The first character in a bigram corresponds to a row, and the second character corresponds to a column in the matrix. A comparison of these two shows that the SSM Matrix has more nonzero entries, to wit, 293 nonzero entries for the SSM Matrix compared to 58 nonzero entries for the Regular Bigram Matrix. The number of all entries is $22^2=484$. As such, it is clear the utilizing the SSM Matrix provides a substantially improved sequence processing pipeline.

To demonstrate this improved performance, the graph of FIG. 101, which is a modified version of a FIG. 4a) from the paper, shows the results of the pipeline without SSM features and the results of the pipeline that uses SSM features. The SSM pipeline achieved better performance while using fewer features than the pipeline based on regular n-grams. The results are shown for the non-plant dataset of protein sequences. Further, FIG. 102 also shows a modified version of another FIG. 4b) from the paper that shows the results of the pipeline without SSM features and the results of the pipeline that uses SSM features. The SSM pipeline also achieved better performance while using fewer features than the pipeline based on regular n-grams. The results are shown for the plant dataset of protein sequences.

In a further embodiment of the present invention, representations based on SSMs are used to integrate information from sensors and motors to help robots operate in their environment. Data processing pipelines that are used in Robotics often apply standard machine learning algorithms to numerical feature vectors extracted from data generated by the sensors and the motors of the robot. Similarly to pipelines designed for analyzing genetic sequences, it may be possible to use the SSM representation to extract features without fully restructuring the pipeline. Thus, SSMs can be used as "plug-ins" for existing data processing pipelines in Robotics.

In one such embodiment, the SSM is reduced to practice in the form of a "plug-in" for the learning pipeline described in the academic paper entitled "Interactive Object Recognition Using Proprioceptive and Auditory Feedback" by J. Sinapov, T. Bergquist, C. Schenck, U. Ohiri, Griffith, S., and A. Stoytchev, the teachings and disclosure of which are incorporated herein in their entireties by reference thereto. The paper described how a robot can recognize different household objects using audio and proprioceptive data recorded by the robot as it interacts with the objects. The SSM representation was reduced to practice by replacing an intermediate numerical representation based on Self-Organizing Map used in the original pipeline with numerical features extracted from SSM matrices. This modification led to significant improvement in performance, which is measured as the proportion of correctly recognized objects. The structure of the modified pipeline is shown in FIG. 103.

The SSM matrices were computed for data from the 7 joints of the robot that was discretized by sorting the individual data recordings into bins of equal size, i.e., using adaptive histograms. The SSM matrices were also computed for temporal data in each of the 33 frequency bins used for audio (more details about the data and the raw data recordings are available in the paper and the publicly available dataset that accompanies the paper). The audio data was also discretized using adaptive histograms. The distance metric based on KL-divergence and additive smoothing was used to compute distances between recorded instances of object interactions. These distance values were summed to obtain distance matrices for proprioception and audio. At this point the SSM representation has been applied, and the remaining part of the learning pipeline described in the paper was used to benchmark object recognition performance.

The benchmark showed that using SSM led to significant improvement in the performance of the pipeline. FIG. 104 shows the improvement in performance due to using the SSM for the task of detecting objects using single behavior and modality combinations. The improvement is shown against the original results described in the paper. These results, FIG. 104 illustrates the performance of the learning pipeline for interactive object recognition that uses SSM, measured in percentage of correctly recognized objects for individual behavior-modality combinations and for combinations of the two sensory modalities. The improvement in performance against the previously published results (shown in Table 1 in the paper) is indicated in parentheses.

FIG. 105 shows the improvement in performance due to using the SSM for the task of detecting objects using multiple behaviors and modalities. For single behavior-modality combinations the accuracy went up by as much as 73.2%, which occurred for proprioception-shake. This means that, on average, using SSM enabled the robot to recognize 36 additional objects correctly (out of 50 objects total) using only joint torques that occurred as the robot was shaking the objects. The improvement for combinations of multiple behaviors and modalities are also significant. In particular, the object recognition accuracy for combining all five behaviors and both modalities increased from 98.2% in the paper to 99.6%. In other words, the error rate went down from 1.8% to 0.4%, which means that the SSM representation had 4.5 times lower error rate than the original pipeline.

As discussed above, FIG. 105 illustrates the performance of the learning pipeline for interactive object recognition that uses SSM, measured in percentage of correctly recognized objects for combinations of multiple different behaviors. The improvement in performance against the previously published results (shown in FIG. 11 in the paper) is indicated in parentheses.

Figure 106:
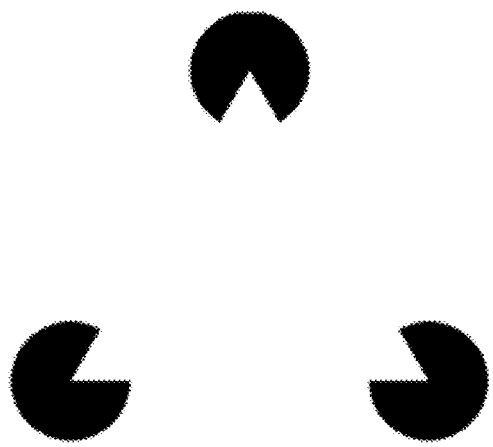
FIG. 106 is a graphical illustration illustrating a computer vision problem.
Figure 107:
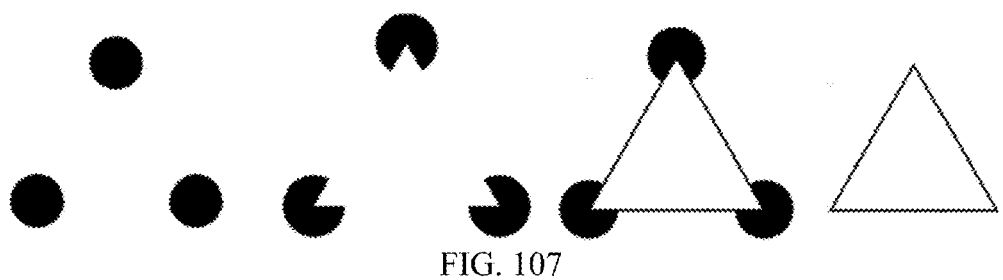
FIG. 107 is a graphical illustration illustrating progression in computer vision for the image of FIG. 106 to possible recognition end points of three balls or a triangle.

Turning now to FIG. 106, there is illustrated a graphical illustration demonstrating a computer vision problem. That is, given the image of FIG. 106, the problem is how this image should be interpreted. FIG. 107 is a graphical illustration illustrating progression in computer vision for the image of FIG. 106 to possible recognition end points of three balls or a triangle. In other words, the computer vision system must determine which of the images in its database of images is the image of FIG. 106 most like.

Figure 108:
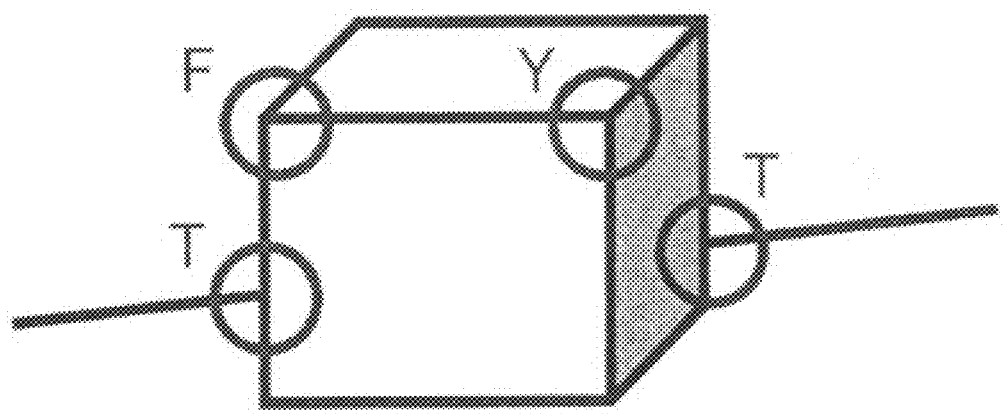
FIG. 108 is a graphic illustration of a computer vision recognition system identifying letter transformations of the image features.
Figure 109:
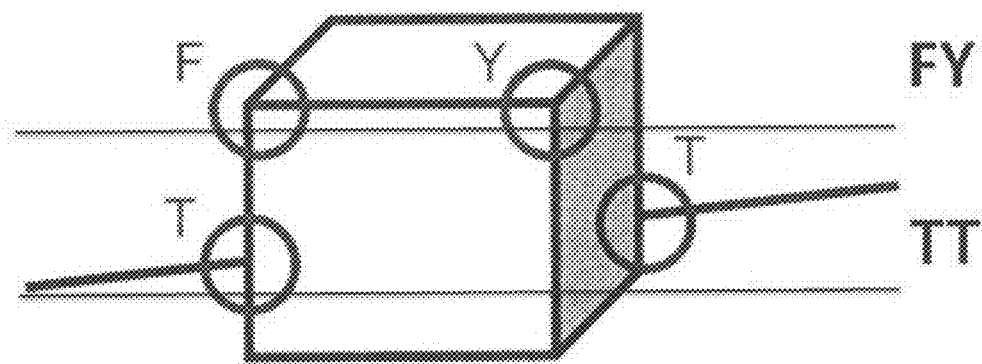
FIG. 109 is a graphical illustration of sequence generation from the letter transformations of the image features based on a horizontal scanning mode in accordance with an embodiment of the present invention.
Figure 110:
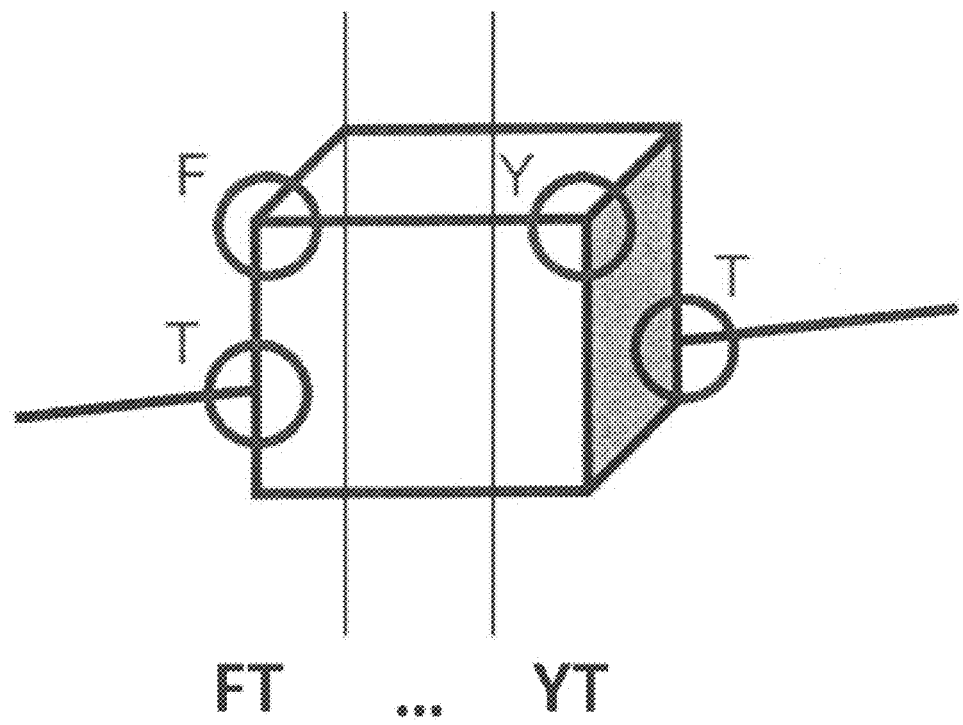
FIG. 110 is a graphical illustration of sequence generation from the letter transformations of the image features based on a vertical scanning mode in accordance with an embodiment of the present invention.
Figures 111, 112:
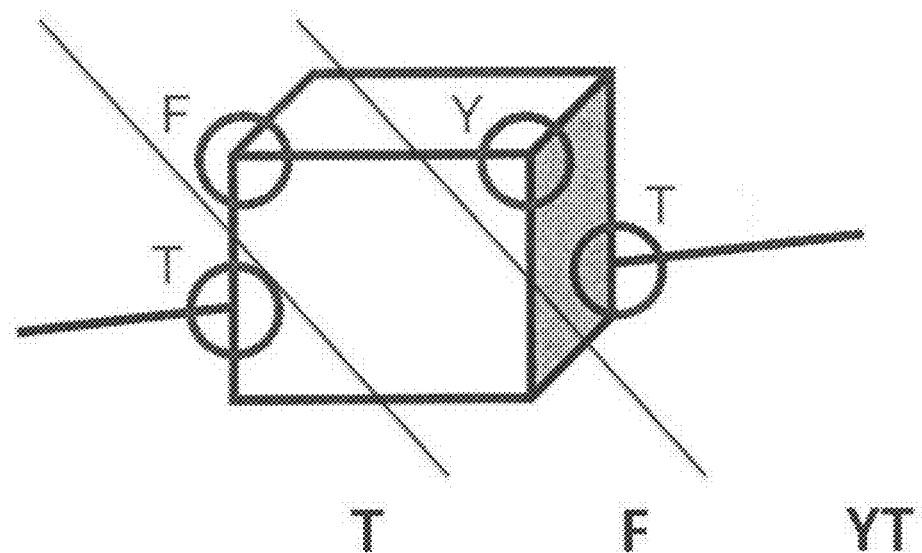
FIG. 111 is a graphical illustration of sequence generation from the letter transformations of the image features based on a diagonal scanning mode in accordance with an embodiment of the present invention.
FIG. 112 is a graphical illustration of a regular dual SSM matrix produced by the dual encoding algorithm for the sequences are $S'=\beta\alpha\gamma\beta$ and $S''=ABAB$ in accordance with an embodiment of the present invention.

FIG. 108 is a graphic illustration of a computer vision recognition system identifying letter transformations of the image features that allows the use of the sequence processing power of the SSM matrices and systems. Basically, as the input imaging device observes an object, certain letters can be identified that are used to form the sequence. To increase the likelihood of identifying the object correctly, the object is scanned in multiple orientations. FIG. 109 is a graphical illustration of sequence generation from the letter transformations of the image features based on a horizontal scanning mode. FIG. 110 is a graphical illustration of sequence generation from the letter transformations of the image features based on a vertical scanning mode. Finally, FIG. 111 is a graphical illustration of sequence generation from the letter transformations of the image features based on a diagonal scanning mode. Once the scanning sequence(s) is(are) formed, these sequences are encoded into SSM matrices. These are then used in the matching algorithms discussed above to identify a match from a database of objects.

In other words, the SSM system performs swipes of the visual frame in different directions (see FIGS. 109-111) and extracts temporal responses of primitive features such as T, Y, and F edge junctions shown in FIG. 108. These responses are converted into sequences, which are grouped so that collections of sequences are broadcasted in a way that guarantees that swipe collections from different orientations actually reach the prototype library. In this way, the SSM system deals with the fact that vision is at least 2D by brute force. All kinds of sequence collections that result from swipes are broadcasted and only later will sequences that do not trigger anything in memory simply die out.

An embodiment of the SSM visual system includes a primitive visual processing unit that receives 2D frames, i.e., pixels, and performs swipes of primitive feature detectors through these frames. The 1D sequences that result from these swipes are packaged either by this unit or by some other unit in a way that the resulting packages retain certain structure. An example of a valid packaging would be collecting sequences from swipes performed at regular angular increments and then packaging the sequences so that different packages correspond to different angles of the viewer with respect to the scene.

The system also contains a broadcasting system of high capacity that is capable of properly routing the packages from the visual processing unit without being overwhelmed. A P2P system in which the processing units are distributed can have this capacity. The system will also have a vast library of primitives to which the packaged sequences are routed. The library may be fixed in one embodiment or it can be extensible in another embodiment. In other words, to see a triangle in FIG. 106, the system has to have some sort of ideal triangle in its memory.

As intimated above, an embodiment of the present invention utilizes a distributed dual model that is produced by a distributed dual encoding algorithm. As discussed at length above, the regular dual SSM matrix shown in FIG. 112 is produced by the dual encoding algorithm. In this example the sequences are S'=βαγβ and S"=ABAB. To encode the dual matrix D(S', S") the regular dual encoding algorithm needs only the histogram vector h' for the first sequence S'. To unroll the matrix, only the histogram vector h" for the second sequence S" is needed.

To explain the distributed dual SSM model produced by the distributed dual encoding algorithm, the same two sequences S'=βαγβ and S"=ABAB will be used with reference to FIG. 113. The numbers stored in the distributed dual matrix are the same as the ones in the regular dual matrix shown in FIG. 112. In this case, however, the elements of the matrix are distributed by rows. The histogram vector h', which is a column vector in FIG. 112, is now distributed by rows as well. Furthermore, each bin value of h' is now replicated in each row, one copy for each column of the matrix. The histogram vector h", which is a row vector of size two in FIG. 112, is now replicated three times, one copy for each row of the matrix.

In other words, because calculations that are performed to encode or decode a character in the SSM matrix touch only one row or only one column at a time, it is possible to distribute these rows or columns across individual computational units in a way that guarantees that a separate unit is dedicated to each row or column of the matrix.

FIG. 114 illustrates the distributed dual model produced by the distributed dual encoding algorithm similarly to FIG. 113, but in this case the rows of the dual matrix D(S', S") are clearly distributed across three different computational nodes. For each node, the corresponding elements of the two distributed and replicated histograms h' and h" are also shown.

With this structure in mind, attention is now directed to FIG. 115 wherein a distributed dual encoding example is illustrated. The two input sequences in this example are still S'=βαγβ and S"=ABAB. As will be recognized from the foregoing, this distributed encoding is similar to the regular dual encoding method, but in this embodiment all replicated elements of the histogram h' that correspond to the current input character from S' are incremented during each iteration. As before, only one column of the matrix is updated during each iteration. This is done by adding the corresponding column of the distributed and replicated histogram h' to the column of the matrix that corresponds to the current character from S".

Figure 116:
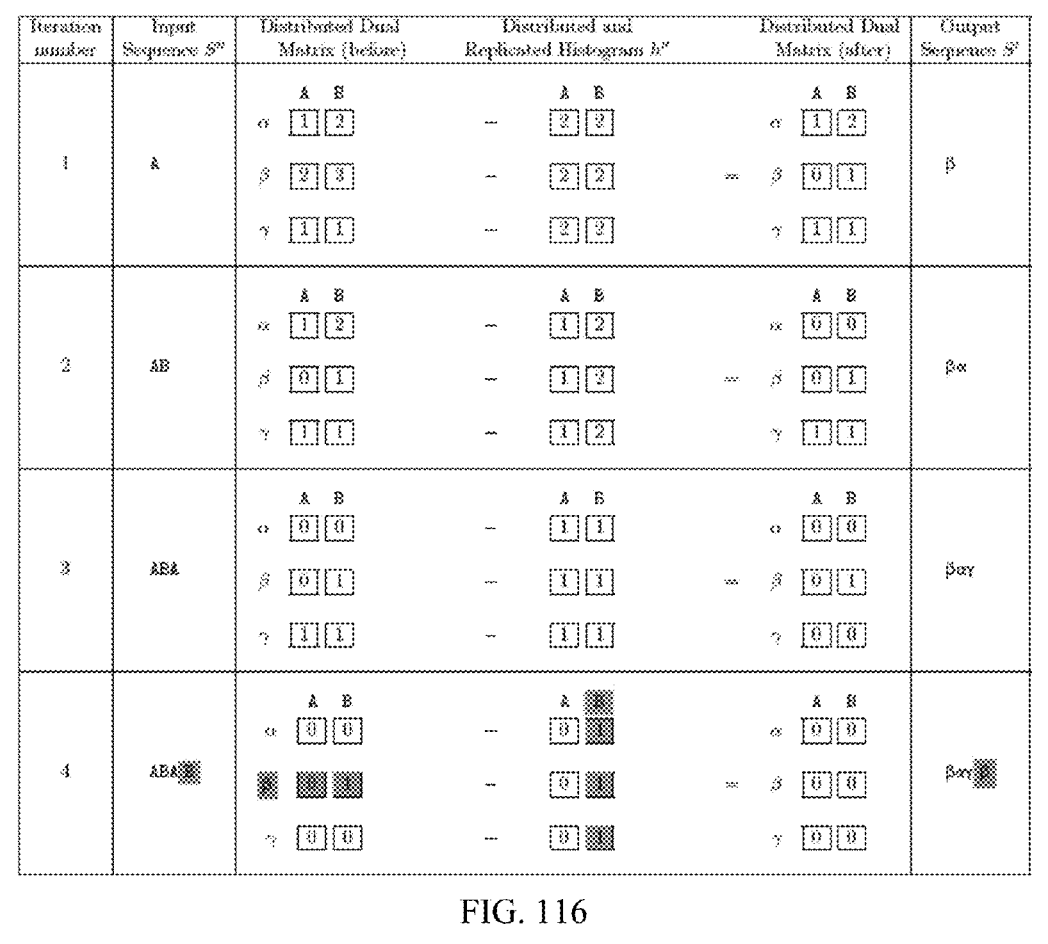

FIG. 116 illustrates the forward unrolling of the distributed dual matrix of FIG. 115. Given the sequence S"=ABAB this example shows how to unroll the sequence S'. The dual model consists of the distributed dual matrix D(S', S") and the distributed and replicated histogram h" for the second sequence. This algorithm is similar to the regular dual unrolling algorithm discussed in detail above, but in this case all computational nodes attempt to subtract their local copy of the histogram vector from their locally stored row of the matrix. All nodes attempt to do this at the same time. As before, this operation succeeds only if all elements of the histogram vector are less than or equal to the corresponding elements of the matrix that belong to the same row. When the bin of the histogram is decremented, this is done for all copies of that bin in all rows/nodes. This is why the B column is highlighted in Iteration 4 of FIG. 116.

As just discussed, therefore, the calculations for dual unrolling can be also distributed. In this case, however, the algorithm needs to access h" instead of h'. FIG. 116 shows how the distributed dual unrolling algorithm works in the example when S'=βαγβ and S"=ABAB. Each node tries to subtract its local copy of h" from its row of the matrix. If this attempt does not make any element of the row negative, then the node emits its character.

Figure 117:
FIG. 117 is a graphical flow diagram illustrating distributed dual encoding with exponential decay in accordance with an embodiment of the present invention.

FIG. 117 illustrates a distributed dual encoding example with exponential decay. The two input sequences in this example are again S'=βαγβ and S"=ABAB. This algorithm combines the methods from the distributed dual encoding and the regular dual exponential encoding discuss above. As before, the elements of the histogram h' decay exponentially over time. In this case, all copies of a histogram bin decay exponentially at the same time.

Figure 118:
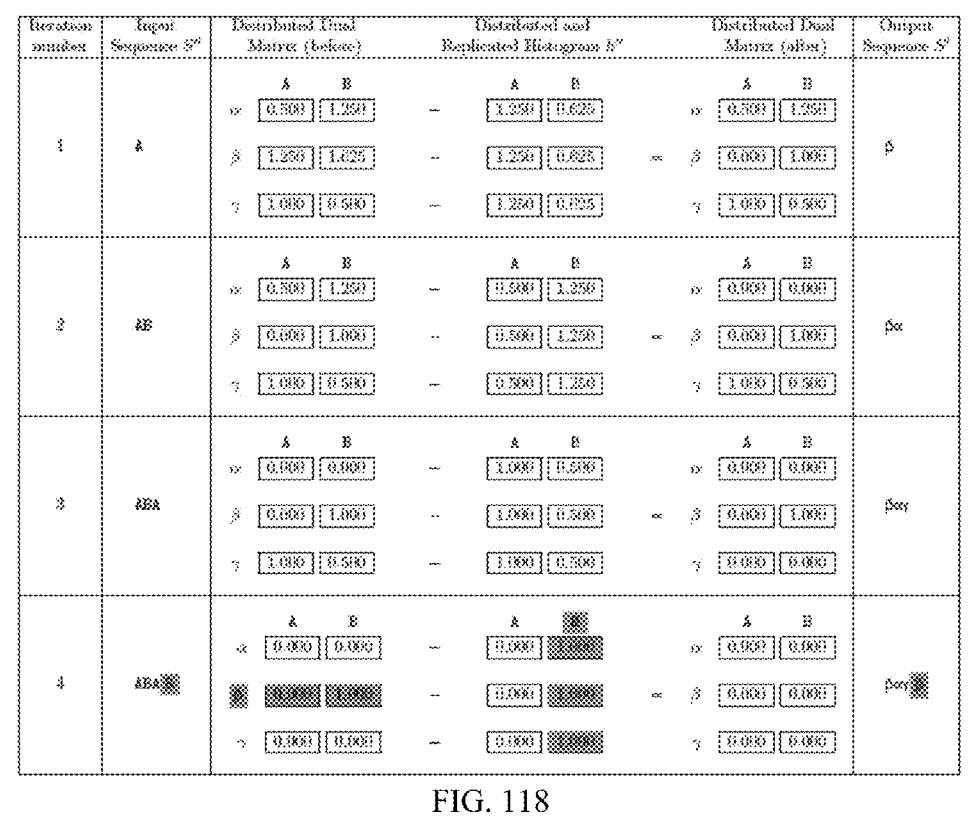

FIG. 118 illustrates the forward unrolling of the distributed dual exponential matrix encoded in FIG. 117. Given the sequence S" this example shows how to unroll the sequence S'. The dual model consists of the distributed dual matrix D(S', S") and the distributed and replicated histogram h" for the second sequence. This method combines the ideas from distributed dual unrolling and dual exponential unrolling, both discussed above in detail.

As FIGS. 117 and 118 make clear, therefore, similar principles can be used to derive distributed versions of dual SSM encoding and unrolling with exponential decay and/or spike-based sequence representation. Each computational unit in the distributed dual encoding algorithm must decay its copy of the histogram h' at every step. On the other hand, each node in the distributed dual unrolling algorithm for exponential matrices needs to exponentially grow its copy of the histogram h" at every step.

Figure 121:
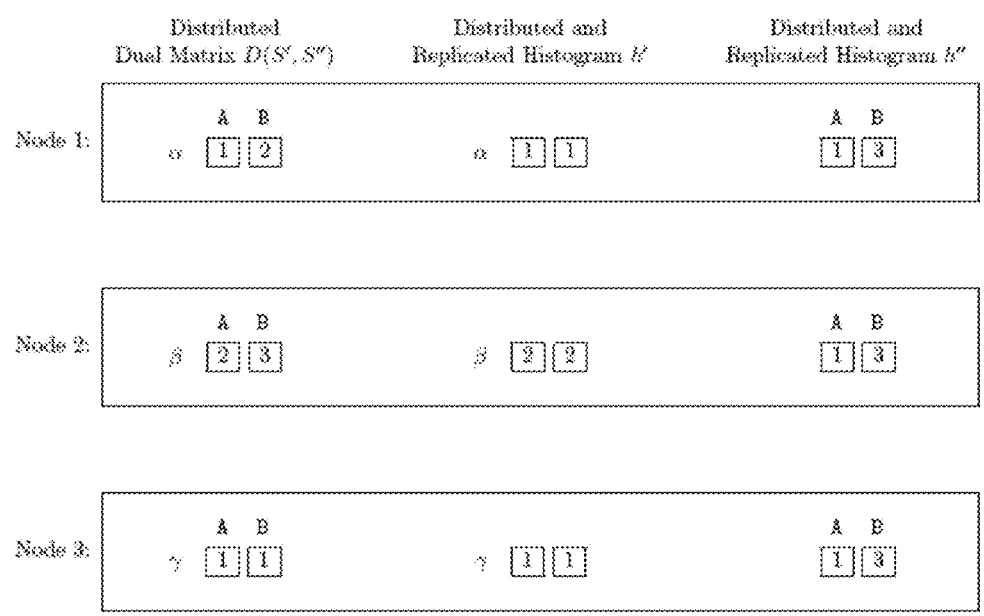

As a second example of the differences between the regular and distributed models, reference is made to FIG. 119 wherein an example of the dual model produced by the encoding algorithm for S'=βαγβ and S"=BBBA is shown. Notice that in this case the dual matrix and the histogram vector h' are the same as the ones in FIG. 112. The histogram vector h" for the second sequence, however, is different. When the distributed dual model produced by the distributed dual encoding algorithm for these sequences is formed as shown in FIG. 120, the numbers stored in the distributed dual matrix are the same as the ones in the regular dual matrix shown in FIG. 119, however, the elements of the matrix are distributed by rows. The histogram vector h', which is a column vector in FIG. 119, is now distributed by rows as well as shown in FIG. 120. Furthermore, each bin value of h' is now replicated in each row, one copy for each column of the matrix. The histogram vector h", which is a row vector of size two in FIG. 119, is now replicated three times, one copy for each row of the matrix. As shown in FIG. 121, the rows of the matrix are mapped to three different computational nodes. The corresponding elements of the distributed and replicated histograms h' and h" are mapped to the correct nodes as well.

Specifically, FIG. 121 shows one example of a dual SSM matrix that is distributed across three different computational nodes. As indicated above, each row of the matrix is mapped to a different node. Each node has local memory and computational resources in order to maintain and update the elements that belong to one row of the matrix. The corresponding elements of the histograms h' and h" are also stored and updated at the node. In the example shown in this FIG. 121, Node 1 hosts the a row of the dual matrix D(S', S"), which is encoded from the two sequences S'=βαγβ and S"=BBBA. Node 1 has one input channel, which is labeled a. This channel is part of the set of channels that are used when representing the sequence S'. In addition, Node 1 has to two other input channels: A and B. In this example, these two channels are used to represent the sequence S". Node 1 also has one output. This output is used by the node to output a signal if it can successfully unroll a character. In other words, if the node is in unrolling mode and if it can successfully subtract the local copy of the histogram h" from the locally stored matrix row without any of the matrix row elements becoming negative then it emits its output character. Similar analysis can be performed for Node 2 and Node 3. Thus, the outputs of the three nodes are collectively used to output the sequence that is unrolled.

FIG. 122 and FIG. 123 show yet another example of the difference between the regular and distributed modes for S'''=γαδγ and S''''=XYZY. As before, the numbers stored in the distributed dual matrix of FIG. 123 are the same as the ones in the regular dual matrix shown in FIG. 122. In the distributed case, however, the elements of the matrix are distributed by rows. The histogram vector h''', which is a column vector in FIG. 122, is now distributed by rows as well. Furthermore, each bin value of h''' is now replicated in each row, one copy for each column of the matrix as shown in FIG. 123. The histogram vector h'', which is a row vector of size 3 in FIG. 122, is now replicated three times, one copy for each row of the matrix as shown in FIG. 123.

FIG. 124 illustrates the distributed dual model produced by the distributed dual encoding algorithm for for S'''=γαδγ and S''''=XYZY. In this example, each row of the dual matrix is mapped to a separate computational node which is responsible for updating only that slice of the matrix along with the corresponding elements of the two histograms. Notice that none of the rows of the matrix are distributed to Node 2, which is not used to perform any of the operations (e.g., encoding or unrolling) related to this distributed dual SSM matrix.

Specifically, FIG. 124 shows another example in which a 3×3 distributed dual matrix is stored across 4 different nodes. In this case Node 2 is not used since the matrix has only 3 rows. Thus, this node will not participate in any of the operations that are required for encoding or unrolling of sequences into or out of this node.

FIG. 125 illustrates the mapping of distributed dual matrices to computational nodes that have subnodes. In this embodiment there are two distributed dual SSM matrices that are mapped across four computational nodes, where each node has two subnodes. Notice that Node 1 hosts the first row of D(S', S'') and the first row of D(S''', S''''). Similarly, Node 3 hosts the third row of D(S', S'') and the second row of D(S''', S''''). In both of these cases, the each row is mapped to a separate subnode. In this example there are two subnodes that are not used (subnode 2.2 and subnode 4.1).

While the nodes in FIG. 125 have only two subnodes, in a different embodiment of this invention each node can have K different subnodes. Also notice that while the y channel is common to the two nodes (i.e., the channel that corresponds to the row label for that node) the inputs from the second sequence are different for the two subnodes. For example, Subnode 3.1 receives input from channels A and B through which S'' is represented. Subnode 3.2, however does not receive these inputs. Instead it receives inputs from channels X, Y, and Z which are used to represent the sequence S''''.

Another thing to notice about the distributed dual representation is that two distributed SSM matrices can share a node not just for computational purposes, but also they share the output of the node. This divergence and convergence of information provides a great flexibility in setting up different computations. While SSM cascades were described previously, now the system is in a position to describe nested and overlapping distributed representations and SSM cascades that use and share computational nodes and subnodes.

In a different embodiment of this distributed representation the nodes may have other control inputs that tell them if they are in encoding or unrolling mode. The nodes many also have inputs that tell them to erase all values stored in each node or subnode. A new matrix with either fewer or mode columns than the previously stored one could also be stored on a node by recruiting more inputs of ignoring existing ones.

It is also worth pointing out that after a matrix is unrolled, its elements contain only zeros. The same is true for the unrolling histogram. In order to use the matrix multiple times (e.g., to match or to unroll) the node will have to have the ability to store a copy of all of these values before it starts to unroll. After a short time interval following unrolling, the node could automatically restore these values to their original levels. This same analysis applies to the previous algorithms that were discussed above.

Note that in this distributed representation each node can perform its computations without the need to know the values of matrix elements or histogram elements stored in any other node. All calculations for both encoding and unrolling can be accomplished locally on the node. There is no need for explicit communication between the nodes or the need for one node to wait to receive data from another node. In other words, the nodes do not have to exchange information for the encoding and unrolling algorithms to work. Thus, this representation is highly parallelizable. Implementation in a GPU or custom hardware can take advantage of this property.

Because the rows of the matrix are distributed across different nodes, these nodes can work in parallel, which can cut the time required to encode the sequence from O(TM') down to O(T). In other words, the algorithm still performs O(TM') operations but each of the M' operations that need to be done to process one of the T characters can be done simultaneously, which can cut the total computational time by a factor of M' (where M' is the number of rows of the matrix).

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

©2013, 2014 Alexander Stoytchev and Vladimir Sukhoy. All Rights Reserved.

What is claimed is:

1. A method of sequence recognition, comprising the steps of:
   receiving an input sequence;
   converting the input sequence to an input sequence SSM Sequence Model (SSM) Matrix;
   comparing the input sequence SSM Matrix to a plurality of known SSM Matrices representing a plurality of known sequences;
   matching the input sequence to the known sequence based on the step of comparing.

2. The method of claim 1, wherein the step of converting comprises the steps of:
   initializing a character histogram vector data structure and the input sequence SSM Matrix to zero;
   scanning a character of the input sequence;
   incrementing a bin counter in the character histogram vector corresponding to the character from the step of scanning;
   adding the character histogram vector to a column in the input sequence SSM Matrix corresponding to the character from the step of scanning;
   repeating the steps of scanning, incrementing, and adding for each character in the input sequence.

3. The method of claim 2, further comprising the step of applying a function to all of the bin counters in the character histogram vector prior to the step of incrementing the bin counter in the character histogram vector corresponding to the character from the step of scanning.

4. The method of claim 3, wherein the step of applying a function comprises the step of exponentially decaying all of the bin counters in the character histogram vector prior to the step of incrementing the bin counter in the character histogram vector corresponding to the character from the step of scanning.

5. The method of claim 1, wherein the step of comparing comprises the step of calculating a distance between the input sequence SSM Matrix and each of the known SSM Matrices, and wherein the step of matching comprises the step of selecting at least one known sequence corresponding to the known SSM Matrix having the smallest distance from the step of calculating.

6. The method of claim 5, wherein the input sequence and the known sequences have non-repeating characters, and wherein the step of calculating the distance between the input sequence SSM Matrix and one of the known SSM Matrices comprises the steps of:
   for each input sequence matrix element in the input sequence SSM Matrix that has a value of one, determining if a corresponding known sequence matrix element in the known sequence SSM Matrix has a value of zero;
   when the step of determining is true, setting a corresponding first distance matrix element in a first distance matrix to one;
   for each known sequence matrix element in the known sequence SSM Matrix that has a value of one, determining if a corresponding input sequence matrix element in the input sequence SSM Matrix has a value of zero;
   when the step of determining is true, setting a corresponding second distance matrix element in a second distance matrix to one;
   counting the number of first distance matrix elements and the number of second distance matrix elements that have a value of one; and
   setting the distance between the input sequence SSM Matrix and the known sequence SSM Matrix to the value of the step of counting.

7. The method of claim 5, wherein the step of calculating the distance between the input sequence SSM Matrix and one of the known SSM Matrices comprises the steps of:
   extracting an input sequence probability distribution of open bigrams for the input sequence from the input sequence SSM Matrix;
   extracting a known sequence probability distribution of open bigrams for the known sequence from the known sequence SSM Matrix; and
   comparing the input sequence probability distribution to the known sequence probability distribution.

8. The method of claim 7, further comprising the step of smoothing probability distributions derived from the input sequence SSM Matrix and the known sequence SSM Matrix to eliminate matrix elements having an initial value of zero.

9. The method of claim 8, wherein the step of smoothing comprises the step of additive smoothing.

10. The method of claim 9, wherein the step of additive smoothing comprises the steps of:
    computing a smoothed probability $\hat{P}_{ij}$ of an open bigram $c_i c_j$ in the input sequence $S_1$ with the formula $$\hat{P}_{ij} = \hat{p}(c_i c_j | S_1) = \frac{X_{ij} + \alpha}{\sum_{k=1}^{M} \sum_{l=1}^{M} X_{kl} + \alpha U},$$

where $\alpha$ is a parameter that controls intensity of the smoothing and U is a number of unique open bigrams that occur in at least one of the input sequence and the known sequence.

11. The method of claim 10, further comprising the step of setting $\alpha$ to a value of 1.

12. The method of claim 10, further comprising the steps of:
    computing a smoothed probability $\hat{Q}_{ij}$ of an open bigram $c_i c_j$ in the known sequence $S_2$ with the formula:

$$\hat{Q}_{ij} = \hat{p}(c_i c_j | S_2) = \frac{Y_{ij} + \alpha}{\sum_{k=1}^{M} \sum_{l=1}^{M} Y_{kl} + \alpha U}.$$

13. The method of claim 12, comprises the step of calculating the KL divergence $d_{KL}(S_1, S_2)$, wherein $S_1$ is the input sequence and $S_2$ is the known sequence, between the smoothed probability distributions $\hat{P}$ and $\hat{Q}$ using the formula:

$$d_{KL}(S_1, S_2) =$$

$$D_{KL}(\hat{P} \| \hat{Q}) = \sum_{i=1}^{M}\sum_{j=1}^{M} \hat{P}_{ij}\log\frac{\hat{P}_{ij}}{\hat{Q}_{ij}} \sum_{i=1}^{M}\sum_{j=1}^{M} \hat{p}(c_ic_j|S_1)\log\frac{\hat{p}(c_ic_j|S_1)}{\hat{p}(c_ic_j|S_2)}.$$

14. The method of claim 13, wherein $D_{KL}(\hat{P}\|\hat{Q})$ is not symmetric and the distance measure $d_{KL}(S_1, S_2)$ is also not symmetric, i.e., $d_{KL}(S_1, S_2) \neq d_{KL}(S_2, S_1)$, formulating a symmetric distance measure by adding two asymmetric distance measures such that $$d_{KL}^{(symm)}(S_1,S_2)=d_{KL}(S_1,S_2)+d_{KL}(S_2,S_1).$$

15. The method of claim 9, wherein the step of additive smoothing is performed only for open bigrams that do occur in at least one of the input sequence or the known sequence.

16. The method of claim 5, wherein the step of calculating the distance between the input sequence SSM Matrix and one of the known SSM Matrices comprises the step of calculating an asymmetric D-KL distance between the input sequence SSM Matrix and the known sequence SSM Matrix.

17. The method of claim 5, wherein the step of calculating the distance between the input sequence SSM Matrix and one of the known SSM Matrices comprises the step of calculating an Euclidean distance between the input sequence SSM Matrix and the known sequence SSM Matrix.

18. The method of claim 5, wherein the step of calculating the distance between the input sequence SSM Matrix and one of the known SSM Matrices comprises the step of calculating a symmetrized Kullback-Leibler (KL) divergence.

19. The method of claim 18, wherein the step of calculating the symmetrized KL divergence comprises the steps of:

for each of the input sequence and the known sequence, computing a probability p ($c_ic_j$|S) for all open bigrams $c_ic_j$ in each sequence S using the formula:

$$p(c_ic_j|S) = \frac{X_{ij}}{\sum_{k=1}^{M}\sum_{l=1}^{M} X_{kl}};$$

and arranging the probabilities for all open bigrams in S in an M×M matrix P for the input sequence such that $P_{ij}$=p ($c_ic_j$|S) and in an M×M matrix Q for the known sequence; and quantifying a difference between P and Q such that $P_{ij}$ is the probability of the open bigram $c_ic_j$ in the input sequence ($S_1$) and $Q_{ij}$ is the probability of $c_ic_j$ in the known sequence ($S_2$), by calculating KL-divergence $D_{KL}(P\|Q)$ defined by the formula:

$$D_{KL}(P\|Q) = \sum_{i=1}^{M}\sum_{j=1}^{M} P_{ij}\log\frac{P_{ij}}{Q_{ij}}.$$

20. The method of claim 5, wherein the step of calculating the distance between the input sequence SSM Matrix and one of the known SSM Matrices comprises the step of calculating a matrix norm $\|\cdot\|$ of the difference between the input sequence matrix ($X_1$) and the known sequence matrix ($X_2$) as $d_{\|\cdot\|}(S_1,S_2)=\|X_1-X_2\|$.

21. The method of claim 1, wherein before the step of comparing, further comprising the step of aligning the input sequence SSM Matrix and the known sequence SSM Matrix.

22. The method of claim 21, wherein the step of aligning comprises the steps of:

determining a union of input sequence elements and known sequence elements;

inserting empty rows and columns in the input sequence SSM Matrix if the input sequence SSM Matrix does not contain all of the union;

inserting empty rows and columns in the known sequence SSM Matrix if the known sequence SSM Matrix does not contain all of the union; and wherein the steps of inserting are done such that the input sequence SSM Matrix and the known sequence SSM Matrix are sorted for rows and columns in a same order.

23. The method of claim 1 adapted for speech recognition, wherein the step of receiving the input sequence comprises the step of receiving an input audio signal spoken by a user directly or from an audio file.

24. The method of claim 23, further comprising the steps of:

converting the input audio signal into input Mel Frequency Cepstrum Coefficients;

discretizing each of the input Mel Frequency Cepstrum Coefficients using an analog to digital conversion to form an input Mel Frequency Cepstrum Coefficient sequence; and encoding each input Mel Frequency Cepstrum Coefficient sequence into an input Mel Frequency Cepstrum Coefficient SSM Matrix.

25. The method of claim 24, wherein each of the known sequence SSM Matrices are formed by known Mel Frequency Cepstrum Coefficient SSM Matrices, and wherein the step of comparing the input sequence SSM Matrix to the plurality of known SSM Matrices representing the plurality of known sequences comprises the step of comparing each input Mel Frequency Cepstrum Coefficient SSM Matrix with a corresponding known Mel Frequency Cepstrum Coefficient SSM Matrix for each known sequence.

26. The method of claim 23, wherein the plurality of known SSM Matrices include SSM Matrices formed from a plurality of known speakers' utterances of known words, and wherein the step of comparing comprises the step of calculating a distance between the input sequence SSM Matrix and each of the known SSM Matrices from the plurality of known speakers' utterances, and wherein the step of matching comprises the steps of selecting one known sequence corresponding to the known SSM Matrix for each known speakers' utterances having the smallest distance from the step of calculating, and determining which of the known sequences from among the known sequences identified by the step of selecting one known sequence corresponding to the known SSM Matrix for each known speakers' utterances is correct by voting among all of the known sequences corresponding to the known SSM Matrix for each known speakers' utterances to determine which known sequence is selected more than any other known sequence from all of the known speakers' utterances.

27. The method of claim 1, wherein the step of receiving the input sequence comprises the step of receiving at discrete times elements of the input sequence.

28. The method of claim 1, wherein the step of receiving the input sequence comprises the step of receiving over a continuous time variation elements of the input sequence.

29. The method of claim 28, wherein the step of receiving over the continuous time variation elements of the input sequence comprises the step of utilizing a coupling function $2^{(t0-t1)}$, where $t_0$ and $t_1$ are the times at which two elements of the input sequence occurred.

30. The method of claim 1 adapted for speech synthesis, wherein the step of receiving the input sequence comprises the step of receiving a textual sequence, and wherein the step of comparing the input sequence SSM Matrix to a plurality of known SSM Matrices representing a plurality of known sequences comprises the step of comparing the input sequence SSM Matrix to a plurality of known SSM Matrices representing a plurality of known sequences for artificial vocal tracts.

31. The method of claim 1 adapted for spell checking, wherein the step of receiving the input sequence comprises the step of receiving a misspelled textual sequence, and wherein the step of comparing the input sequence SSM Matrix to a plurality of known SSM Matrices representing a plurality of known sequences comprises the step of comparing the input sequence SSM Matrix to a plurality of known SSM Matrices representing a plurality of known sequences for correctly spelled textual sequences.

32. The method of claim 1, wherein the step of converting comprises the steps of:
   counting all open bigrams for the input sequence;
   forming the input sequence SSM Matrix from the open bigrams, the input sequence SSM Matrix having the characters of the input sequence sorted alphabetically designate the rows and the columns of the input sequence SSM Matrix; and
   forming an input sequence histogram vector for the input sequence.

33. The method of claim 1, wherein the step of converting comprises the steps of:
   counting all open trigrams for the input sequence;
   forming the input sequence SSM Matrix as a three dimensional SSM Matrix from the open trigrams.

34. The method of claim 1, wherein the step of converting comprises the steps of:
   counting all open n-grams for the input sequence;
   forming the input sequence SSM Matrix as an n-dimensional SSM Matrix from the open n-grams.

35. The method of claim 1, further comprising the steps of:
   retrieving a dual SSM Matrix generated from the known sequence identified by the step of matching and a second sequence (D(S", S'));
   extracting the second sequence (S") from the dual SSM Matrix (D(S", S')) and a first histogram vector (h') of the known sequence identified by the step of matching (S').

36. The method of claim 35, further comprising the cascaded steps of:
   retrieving a dual SSM Matrix generated from the second sequence and a third sequence (D(S'", S"));
   extracting the third sequence (S'") from the dual SSM Matrix (D(S'", S")) and a second histogram vector (h") of the second sequence (S").

37. The method of claim 1, wherein the step of converting the input sequence to an input sequence SSM Matrix comprises the step of converting the input sequence to a spike-based representation of the input sequence and converting the spike-based representation of the input sequence to a spike-based input sequence SSM Matrix, and wherein the step of comparing the input sequence SSM Matrix to a plurality of known SSM Matrices representing a plurality of known sequences comprises the step of comparing the spike-based input sequence SSM Matrix to a plurality of spike-based known SSM Matrices.

38. The method of claim 1, adapted for computer vision, wherein the step of receiving the input sequence comprises the step of visually scanning a physical object in at least one direction, identifying features from the step of visually scanning, assigning sequence elements to the features, and forming the input sequence from the sequence elements.

39. The method of claim 1, wherein the step of receiving an input sequence comprises receiving two input sequences;
   wherein the step of converting the input sequence to an input sequence SSM Matrix comprises the step of converting the two input sequences to a dual input sequence SSM Matrix;
   wherein the step of comparing the input sequence SSM Matrix to a plurality of known SSM Matrices representing a plurality of known sequences comprises the step of comparing the dual input sequence SSM Matrix to a plurality of dual known SSM Matrices; and
   wherein the step of matching the input sequence to the known sequence based on the step of comparing comprises the step of matching the two input sequences to two known sequences based on the step of comparing.

40. The method of claim 39, wherein the step of comparing comprises the step of calculating the Euclidean distance between the dual input sequence SSM Matrix and each of the plurality of dual known SSM Matrices.

41. The method of claim 39, wherein the step of comparing comprises the step of calculating a symmetrized Kullback-Leibler (KL) divergence between the dual input sequence SSM Matrix and each of the plurality of dual known SSM Matrices.

42. The method of claim 39, adapted for prediction of a property of a biological molecule or a part of a biological molecule including at least one of predicting a location of a protein within a cell, subcellular protein localization, predicting the structural class of a protein α, β, α+β, or α/β, predicting the functional family of an enzyme, oxidoreductase, transferase, hydrolase, lyase, isomerase, or ligase, predicting the location of a protein within the nucleus of a cell, subnuclear protein localization, predicting the location of a protein within mitochondria, submitochondria protein localization, detecting papillomaviruses that can infect humans and may cause cancer, detecting proteins that may bind to DNA, participating in gene regulation, wherein the step of receiving the input sequence comprises the step of receiving a sequence of nucleic or amino acids that encode molecules or parts of a molecule.

43. The method of claim 42, adapted for subcellular protein localization in an existing machine learning pipeline, further comprising the step of replacing a feature extraction step from the standard machine learning pipeline that uses regular n-gram counters with open bigram counters.

44. The method of claim 39, adapted for application in data processing pipelines in Robotics wherein the step of receiving the input sequence comprises the step of receiving a sequence that was derived from sensory or motor feedback recorded by the robot.

45. The method of claim 44, further comprising the step of replacing an existing standard machine learning representation with dual SSM Matrices.

46. The method of claim 44, adapted for recognition of objects from data obtained by the robot as it interacts with the objects, wherein the step of receiving a sequence that was derived from sensory or motor feedback comprises the step of deriving a sequence from one of the frequency bins used for audio using adaptive discretization.

47. The method of claim 44, wherein the step of receiving a sequence that was derived from sensory or motor feedback comprises the step of deriving a sequence from proprioceptive feedback including at least one of joint position or torque.

48. The method of claim 47, wherein the step of matching comprises the step of calculating a distance metric between recorded instances of object interactions based on KL-divergence and additive smoothing, summing the distance metrics to obtain distance matrices for proprioception and audio.

49. The method of claim 1, further comprising the step of unrolling the known sequence from the SSM Matrix and the histogram of the known sequence.

50. The method of claim 49, wherein the step of unrolling comprises the steps of:
calculating a total number of open bigrams that are present in the known sequence by summing up all $X_{ij}$ elements of the SSM Matrix of the known sequence;
calculating a sequence length, T, by solving the quadratic equation $T(T+1)/2$ and taking its positive root;
extract the character histogram, $h=[h_1, h_2, h_3, \ldots, h_M]$, from diagonal entries of the SSM Matrix of the known sequence by solving a quadratic equation $h_i(h_i+1)/2=X_{ii}$ for $i=1, 2, 3, \ldots, M$;
calculating a frequency for the $i^{th}$ character in the known sequence alphabet as $$h_i = \frac{-1 + \sqrt{1 + 8X_{ii}}}{2}, i = 1, \ldots, M;$$

calculating row sums of the SSM Matrix of the known sequence by adding open bigram counters in each row; and
reconstructing a total order of the characters in the known sequence by sorting the row sums in descending order.

51. The method of claim 49, wherein the histogram for the known sequence is stored with the known sequence SSM Matrix, comprising the steps of:
subtracting the histogram vector from one of the rows of the known sequence SSM Matrix without any of its entries becoming negative to unroll a first character of the known sequence;
decrementing the histogram bin counter that corresponds to the first character; and
repeating the steps of subtracting and decrementing for each subsequent element of the known sequence to be unrolled until the step of subtracting results in all rows of the known sequence SSM Matrix being equal to zero.

52. The method of claim 51, wherein at least one of the entries of the known sequence SSM Matrix is missing, further comprising the step of skipping the step of subtracting for that matrix element.

53. The method of claim 1, adapted for text categorization, wherein the step of comparing comprises the step of comparing the input sequence SSM Matrix to a plurality of known SSM Matrices representing a plurality of known text categorizations, and wherein the step of matching the input sequence to the known sequence based on the step of comparing comprises the step of categorizing the input sequence as one of the known text categorizations based on the step of comparing.

54. The method of claim 1, adapted for a search engine, wherein the step of comparing comprises the step of comparing the input sequence SSM Matrix to a plurality of known SSM Matrices representing a plurality of known search results, and wherein the step of matching the input sequence to the known sequence based on the step of comparing comprises the step of returning a listing of search results ordered based on closeness calculated in the step of comparing.

55. The method of claim 1, further comprising the step of unrolling in reverse the known sequence from the known sequence SSM Matrix and the histogram of the known sequence, comprising the steps of:
subtracting the histogram vector from one of the columns of the known sequence SSM Matrix without any of its entries becoming negative to unroll a last character of the known sequence;
decrementing the histogram bin counter that corresponds to the last character; and
repeating the steps of subtracting and decrementing for each previous element of the known sequence to be unrolled in reverse until the step of subtracting results in all columns of the known sequence SSM Matrix being equal to zero.

56. A method of extracting a second sequence, comprising the steps of:
receiving a first sequence (S');
retrieving a dual SSM Sequence Model (SSM) Matrix generated from the first sequence and a second sequence (D(S", S'));
extracting the second sequence (S") from the dual SSM Matrix (D(S", S')) and a first histogram vector (h') of the first sequence (S').

57. The method of claim 56, further comprising the step of generating the dual SSM Matrix (D(S", S')) from the first sequence (S') and the second sequence (S").

58. The method of claim 57, wherein the step of generating comprises the steps of:
counting all open bigrams between characters of the first sequence and characters of the second sequence;
forming the dual SSM Matrix (D(S", S')) having the characters of the second sequence designate the rows of the dual SSM Matrix and the characters of the first sequence designate the columns of the dual SSM Matrix.

59. The method of claim 57, wherein the first sequence and the second sequence are of different lengths, wherein the step of generating comprises the steps of:
counting all open bigrams between characters of the first sequence and all characters of the second sequence;
forming the dual SSM Matrix (D(S", S')) having the characters of the second sequence designate the rows of the dual SSM Matrix and the characters of the first sequence designate the columns of the dual SSM Matrix.

60. The method of claim 57, wherein the first sequence and the second sequence are of different lengths, wherein the step of generating comprises the steps of:

counting all open bigrams between characters of the first sequence and characters of the second sequence that occur after each character in the first sequence;

forming the dual SSM Matrix (D(S", S')) having the characters of the second sequence designate the rows of the dual SSM Matrix and the characters of the first sequence designate the columns of the dual SSM Matrix.

61. The method of claim 57, wherein the first sequence and the second sequence are of different lengths, wherein the step of generating comprises the steps of:

counting all open bigrams between characters of the first sequence and characters of the second sequence that occur after a time window of each character in the first sequence;

forming the dual SSM Matrix (D(S", S')) having the characters of the second sequence designate the rows of the dual SSM Matrix and the characters of the first sequence designate the columns of the dual SSM Matrix.

62. The method of claim 57, wherein the first sequence and the second sequence are of different lengths, further comprising the step of rescaling the sequences to have equal lengths.

63. The method of claim 57, further comprising the step of converting the input sequence to a spike-based representation of the input sequence, and wherein the step of generating the dual SSM Matrix (D(S", S')) from the first sequence (S') and the second sequence (S"), comprises the step of generating the dual SSM Matrix (D(S", S')) from the spike-based representation of the first sequence (S') and a spike based representation of the second sequence (S").

64. The method of claim 63, wherein the step of generating the dual SSM Matrix (D(S", S')) from the spike-based representation of the first sequence (S') and a spike based representation of the second sequence (S") comprises the steps of generating the dual SSM Matrix (D(S", S')) with exponential decay from the spike-based representation of the first sequence (S') and a spike based representation of the second sequence (S").

65. The method of claim 64, wherein the step of generating the dual SSM Matrix (D(S", S')) with exponential decay comprises the steps of increasing the histogram element h" at a time of occurrence of a spike of that channel in S", exponentially decreasing all elements of the histogram h" after the time of occurrence, and sampling the value of the histogram h" at the time of occurrence of a spike on a channel in S', and adding the sampled vector to the column of D(S", S') that corresponds to the channel in S' on which the spike occurred.

66. The method of claim 65, wherein the first time and the second time are synchronized.

67. The method of claim 65, wherein the first time and the second time are not synchronized.

68. The method of claim 56, wherein invariants exist between n different sequences, comprising the steps of forming a dual SSM Matrix for each of $n^2$ pairs of the n different sequences.

69. The method of claim 68, wherein the step of retrieving the dual SSM Matrix generated from the first sequence and a second sequence (D(S", S')) comprises the step of retrieving all of the dual SSM Matrices generated from the first sequence and each of the other n−1 sequences (D(S", S'), D(S'", S'), D(S"", S'), . . . , D(S", S')), and wherein the step of extracting the second sequence (S") from the dual SSM Matrix (D(S", S')) and a first histogram vector (h') of the first sequence (S') comprises the step of extracting each of the other n−1 sequences (S" . . . , S") from each of the n−1 dual SSM Matrices (D(S", S'), D(S'", S'), D(S"", S'), . . . , D(S ″ , S')) and a first histogram vector (h') of the first sequence (S').

70. The method of claim 69, further comprising the step of utilizing a separate processing unit to perform the steps of extracting each of the n−1 sequences (S" . . . S") from each of the n−1 dual SSM Matrices (D(S", S'), D(S'", S'), D(S'", S'), . . . , D(S", S')) and a first histogram vector (h') of the first sequence (S').

71. The method of claim 56, further comprising the cascaded steps of:

retrieving a dual SSM Matrix generated from the second sequence and a third sequence (D(S'", S"));

extracting the third sequence (S'") from the dual SSM Matrix (D(S'", S")) and a second histogram vector (h") of the second sequence (S").

72. The method of claim 71, further comprising the cascaded steps of:

retrieving a dual SSM Matrix generated from the third sequence and a fourth sequence (D(S"", S'"));

extracting the fourth sequence (S"") from the dual SSM Matrix (D(S"", S'")) and a third histogram vector (h'") of the third sequence (S'").

73. The method of claim 71, further comprising the steps of:

retrieving a dual SSM Matrix generated from the second sequence and a fourth sequence (D(S'"", S"));

extracting the fourth sequence (S"") from the dual SSM Matrix (D(S"", S")) and a second histogram vector (h") of the second sequence (S").

74. The method of claim 56, further comprising the steps of:

receiving an input sequence;

converting the input sequence to an input sequence SSM Matrix;

comparing the input sequence SSM Matrix to a plurality of known SSM Matrices representing a plurality of known sequences; and matching the input sequence to the known sequence based on the step of comparing; and wherein the known sequence from the step of matching is the first sequence (S').

75. The method of claim 56, adapted for analysis of biological sequences, wherein the step of receiving a first sequence (S') comprises the step of receiving a DNA sequence, and wherein the step of retrieving comprises the step of retrieving a dual SSM Matrix generated from the DNA sequence and an additional property that is associated with the DNA sequence (D(S", S')), and wherein the step of extracting comprises the step of extracting the additional property that matches the DNA sequence from the step of receiving.

76. The method of claim 56, adapted to robotic control, wherein the step of receiving comprises the step of receiving a feedback signal from at least one sensor or motor of a robot, converting the feedback signal to the first sequence (S').

77. The method of claim 56, wherein invariants exist between 3 different sequences, comprising the steps of forming a 3D SSM Matrices of open trigram counters for each of 27 groups of the 3 different sequences.

78. A method of increasing efficiency of sequence processing systems using HMMs, comprising the step of utilizing SSM Sequence Model (SSM) Matrices in place of the HMMs.

79. A system, comprising:

an input device for receiving an input sequence;

a processor coupled to the input device, the processor converting the input sequence to an input sequence SSM Sequence Model (SSM) Matrix;

a memory device configured to store a plurality of known SSM Matrices representing a plurality of known sequences; and wherein the processor compares the input sequence SSM Matrix to the plurality of known SSM Matrices in order to match the input sequence to the known sequence.

80. The system of claim 79, configured for spell checking, wherein the input device is one of a keyboard, touchscreen text entry device, or text file, wherein the input sequence is a misspelled word, wherein the plurality of known SSM Matrices representing a plurality of known sequences are derived from correctly spelled words, and wherein the processor suggests one of the correctly spelled words to replace the misspelled word.

81. The system of claim 79, configured for voice recognition, wherein the input device is one of a microphone or audio file, further comprising a signal analyzer coupled to the input device that is configured to convert an input audio signal into input Mel Frequency Cepstrum Coefficients, an analog to digital converter coupled to the signal analyzer to discretize each of the input Mel Frequency Cepstrum Coefficients to form an input Mel Frequency Cepstrum Coefficient sequence, and wherein the processor encodes each input Mel Frequency Cepstrum Coefficient sequence into an input Mel Frequency Cepstrum Coefficient SSM Matrix, and wherein each of the known sequence SSM Matrices stored in the memory are formed by known Mel Frequency Cepstrum Coefficient SSM Matrices for known words, and wherein the processor outputs a known word corresponding to the input audio signal.

82. The system of claim 79, configured for speech synthesis, further comprising an output speaker, wherein the input device is one of a keyboard, touchscreen text entry device, or text file, wherein the input sequence is a textual word, wherein the plurality of known SSM Matrices representing a plurality of known sequences are derived from audio files of spoken words, and wherein the processor drives the speaker with one of the audio files of the spoken words corresponding to the textual word.

83. The system of claim 79, configured for computer vision, wherein the input device is one of a visual scanner or visual image file, wherein the processor extracts visual features from an image of an object and assigns sequence elements to each visual feature to form the input sequece, wherein the plurality of known SSM Matrices representing a plurality of known sequences are derived from visual files of scanned images of known objects, and wherein the processor identifies the object as one of the known objects.

84. The system of claim 79, wherein the processor and the memory are configured on a single chip.

85. The system of claim 79, wherein the processor comprises a plurality of parallel processors.

86. The system of claim 79, wherein the processor is a GPU.

* * * * *